(12) United States Patent
Yahata et al.

(10) Patent No.: US 11,688,025 B2
(45) Date of Patent: *Jun. 27, 2023

(54) METHOD, INFORMATION TERMINAL, AND NON-TRANSITORY COMPUTER-READABLE RECORDING MEDIUM THAT CUSTOMIZE MENU INFORMATION BASED ON RELIGION INFORMATION

(71) Applicant: Panasonic Intellectual Property Management Co., Ltd., Osaka (JP)

(72) Inventors: Hiroshi Yahata, Osaka (JP); Takahiro Nishi, Nara (JP); Tadamasa Toma, Osaka (JP); Toshiyasu Sugio, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/485,583

(22) Filed: Sep. 27, 2021

(65) Prior Publication Data

US 2022/0012826 A1 Jan. 13, 2022

Related U.S. Application Data

(63) Continuation of application No. PCT/JP2020/014468, filed on Mar. 30, 2020.

(30) Foreign Application Priority Data

Mar. 3, 2020 (JP) .............................. JP2020-035960

(51) Int. Cl.
*G06Q 50/12* (2012.01)
*G16H 20/60* (2018.01)
(Continued)

(52) U.S. Cl.
CPC ............. *G06Q 50/12* (2013.01); *G06F 9/451* (2018.02); *G06Q 30/0627* (2013.01);
(Continued)

(58) Field of Classification Search
CPC ............... G06Q 50/12; G06Q 30/0627; G06Q 30/0635; G06Q 30/0641; G06F 9/451;
(Continued)

(56) References Cited

U.S. PATENT DOCUMENTS 6,301,564 B1 * 10/2001 Halverson ............... G06Q 50/12
705/15
6,370,513 B1 * 4/2002 Kolawa .................. G06Q 30/02
705/7.33
(Continued)

FOREIGN PATENT DOCUMENTS

CN 106022989 A 10/2016
JP 2005-222191 8/2005
(Continued)

OTHER PUBLICATIONS

E. Y. Daraghmi and S.-M. Yuan, "PMR: Personalized Mobile Restaurant system," 2013 5th International Conference on Computer Science and Information Technology, Amman, Jordan, 2013, pp. 275-282, doi: 10.1109/CSIT.2013.6588792. (Year: 2013).*
(Continued)

*Primary Examiner* — Ashford S Hayles
(74) *Attorney, Agent, or Firm* — Greenblum & Bernstein P.L.C.

(57) ABSTRACT

A method acquires, on a basis of a restaurant ID, menu information indicating one or more foods provided by a restaurant over a network from a second server associated with the restaurant corresponding to the restaurant ID, extracts one or more first foods compatible with religion information on a basis of the menu information and the
(Continued)

religion information, displays the one or more first foods through a second operation screen, corresponding to the second server, for accepting an order of a food to be provided by the restaurant and displayed on a display of the information terminal of a user, and transmits food order information indicating a food selected from among the one or more first foods and a seat ID to the second server.

19 Claims, 42 Drawing Sheets

(51) Int. Cl.
G06F 9/451 (2018.01)
G06Q 30/0601 (2023.01)

(52) U.S. Cl.
CPC ..... *G06Q 30/0635* (2013.01); *G06Q 30/0641* (2013.01); *G16H 20/60* (2018.01)

(58) Field of Classification Search
CPC ............ G06F 9/4451; G16H 20/60; A23V 2200/266; A23V 2200/26
See application file for complete search history.

(56) References Cited

U.S. PATENT DOCUMENTS

| | | | | |
|---|---|---|---|---|
| 6,980,999 B1* | 12/2005 | Grana | G06Q 30/02 | 600/300 |
| 7,953,873 B1* | 5/2011 | Madurzak | G06Q 30/02 | 709/229 |
| 8,732,101 B1* | 5/2014 | Wilson | G06Q 30/0269 | 706/15 |
| 2001/0021914 A1* | 9/2001 | Jacobi | G06Q 30/0641 | 705/26.1 |
| 2002/0004749 A1* | 1/2002 | Froseth | G06Q 50/00 | 705/16 |
| 2002/0029162 A1* | 3/2002 | Mascarenhas | G06Q 30/0203 | 707/E17.109 |
| 2003/0091964 A1* | 5/2003 | Yeager | G06Q 30/02 | 708/133 |
| 2003/0158465 A1* | 8/2003 | Galli | G16H 20/60 | 600/300 |
| 2003/0208409 A1* | 11/2003 | Mault | G06Q 30/0639 | 705/26.9 |
| 2005/0171800 A1* | 8/2005 | Yamaguchi | G06Q 50/12 | 715/811 |
| 2006/0026048 A1* | 2/2006 | Kolawa | G06Q 10/063 | 705/7.11 |
| 2009/0077007 A1* | 3/2009 | Schwarzberg | G06Q 30/02 | |
| 2010/0003647 A1* | 1/2010 | Brown | G09B 19/0092 | 434/127 |
| 2011/0208617 A1* | 8/2011 | Weiland | G06Q 30/0641 | 705/27.1 |
| 2011/0258058 A1* | 10/2011 | Carroll | G06Q 30/06 | 705/15 |
| 2011/0318717 A1* | 12/2011 | Adamowicz | G16H 20/60 | 434/127 |
| 2012/0094258 A1* | 4/2012 | Langheier | G16H 20/30 | 434/127 |
| 2012/0095863 A1* | 4/2012 | Schiff | G06Q 30/0282 | 705/26.7 |
| 2012/0226698 A1* | 9/2012 | Silvestre | G06Q 30/02 | 707/E17.084 |
| 2012/0233002 A1* | 9/2012 | Abujbara | G16H 20/60 | 705/15 |
| 2012/0259657 A1* | 10/2012 | Keynan | G16Z 99/00 | 705/2 |
| 2012/0303638 A1* | 11/2012 | Bousamra | G16H 20/60 | 707/751 |
| 2013/0030944 A1* | 1/2013 | Nicod | G06Q 30/0281 | 705/26.5 |
| 2013/0080438 A1* | 3/2013 | Tompkins | G06Q 30/0282 | 707/740 |
| 2013/0085345 A1* | 4/2013 | Geisner | G06Q 30/00 | 600/300 |
| 2013/0108993 A1* | 5/2013 | Katz | G09B 23/28 | 434/127 |
| 2013/0211948 A1* | 8/2013 | Lipscher | H04L 67/10 | 705/26.5 |
| 2013/0222406 A1* | 8/2013 | Wolfe | G06Q 30/0241 | 345/582 |
| 2013/0224694 A1* | 8/2013 | Moore | G09B 19/0092 | 434/127 |
| 2013/0325640 A1* | 12/2013 | Morgan | G06Q 50/12 | 705/15 |
| 2013/0339348 A1* | 12/2013 | Pickelsimer | G06Q 30/0631 | 707/723 |
| 2014/0012794 A1* | 1/2014 | Dillon | G06N 5/02 | 706/46 |
| 2014/0074650 A1* | 3/2014 | Elias | G06Q 30/0631 | 705/26.7 |
| 2014/0080102 A1* | 3/2014 | Krishna | G09B 19/0092 | 434/127 |
| 2014/0214534 A1* | 7/2014 | L'Heureux | G06Q 30/0252 | 705/14.64 |
| 2014/0214746 A1* | 7/2014 | Song | G06N 5/02 | 706/46 |
| 2014/0220516 A1* | 8/2014 | Marshall | G16H 20/60 | 434/127 |
| 2014/0229498 A1* | 8/2014 | Dillon | H04L 67/306 | 707/767 |
| 2014/0287384 A1* | 9/2014 | Boyes | G09B 5/02 | 434/127 |
| 2014/0310651 A1 | 10/2014 | Padgett et al. | | |
| 2014/0324624 A1* | 10/2014 | Ward | H04W 4/021 | 705/26.7 |
| 2014/0344953 A1* | 11/2014 | Roundtree | G06Q 30/0242 | 726/28 |
| 2015/0199776 A1* | 7/2015 | Gluck | G06Q 30/0261 | 705/15 |
| 2015/0199777 A1* | 7/2015 | Rodriguez | G06Q 50/12 | 705/15 |
| 2015/0276700 A1* | 10/2015 | Goel | G01N 33/02 | 73/865.7 |
| 2016/0012513 A1* | 1/2016 | Martinez | G06Q 50/12 | 705/15 |
| 2017/0301045 A1* | 10/2017 | Kubo | G06F 16/22 | |
| 2018/0089658 A1* | 3/2018 | Bell | G06F 3/04817 | |
| 2018/0165620 A1* | 6/2018 | Ross | G06F 3/0482 | |
| 2018/0189901 A1* | 7/2018 | Poisner | G06Q 50/12 | |
| 2018/0190375 A1* | 7/2018 | Chapela | A61B 5/486 | |
| 2018/0364887 A1* | 12/2018 | Bell | G06F 3/04817 | |
| 2019/0163710 A1* | 5/2019 | Haghighat Kashani | G06F 3/0482 | |
| 2019/0370916 A1* | 12/2019 | Surkin | H04L 67/53 | |
| 2020/0265508 A1* | 8/2020 | Fuellgraf | G06K 7/1417 | |
| 2020/0387985 A1* | 12/2020 | Khorakiwala | G06Q 50/12 | |

FOREIGN PATENT DOCUMENTS

| | | | | |
|---|---|---|---|---|
| JP | 2008-299821 | | 12/2008 | |
| JP | 2016-134002 | | 7/2016 | |
| JP | 2019-023829 | | 2/2019 | |
| KR | 101141204 B1 | * | 8/2007 | |
| KR | 20070084743 A | * | 5/2012 | |
| TW | 201734933 A | | 10/2017 | |
| WO | WO-2017168239 A1 | * | 10/2017 | ............ G06Q 10/10 |

OTHER PUBLICATIONS

Eugenio Roanes-Lozano, José Luis Galán-García, Gabriel Aguilera-Venegas, A prototype of a RBES for personalized menus generation, Applied Mathematics and Computation, vol. 315, 2017, pp. 615-624 (Year: 2017).*

International Search Report of PCT application No. PCT/JP2020/014468 dated Aug. 11, 2020.

(56) References Cited

OTHER PUBLICATIONS

English Translation of Chinese Search Report dated Mar. 30, 2023 for the related Chinese Patent Application No. 202080081367.4.

* cited by examiner

FIG. 22

| TYPE OF RELIGION | BEEF | PORK | CHICKEN | FISH | EGGS | DAIRY | ALCOHOL |
|---|---|---|---|---|---|---|---|
| ISLAM | | X | | Y | | Y | X |
| JUDAISM | | X | Y | Y | Y | Y | Y |
| HINDUISM | X | X | Y | X | Y | | |
| CHRISTIANITY | Y | Y | Y | Y | | | Y |
| BUDDHISM | Y | Y | Y | Y | | | |

| FIELD | VALUE |
|---|---|
| INFORMATION CATEGORY | FOOD |
| PUBLISHER | ABC MATCHING |
| PUBLICATION DATE | 2/7/2020 |
| DATA CLASS | RELIGION INFORMATION |
| DATA MEASUREMENT DATE | 2/7/2020 |
| RELIGION TYPE | BUDDHISM |
| BEEF | 1 |
| PORK | 1 |
| CHICKEN | 1 |
| FISH | 1 |
| EGGS | 3 |
| DAIRY | 5 |
| ALCOHOL | 5 |

FIG. 24

| FIELD | VALUE | |
|---|---|---|
| FOOD NAME | RAMEN B SET | 2401, 2400 |
| SHOYU RAMEN | 1 | |
| SOUP DUMPLING | 3 | |

| FIELD | VALUE | |
|---|---|---|
| FOOD NAME | SHOYU RAMEN | 2402, 2400 |
| FLOUR | 50 g | |
| SALT | 5 g | |
| STARCH | 1 g | |
| SOY SAUCE | 10 g | |
| OYSTER SAUCE | 1 g | |
| SESAME SEEDS | 0.5 g | |
| PORK CHAR SIU | 18 g | ← BAD |
| WATER | 400 g | |

| FIELD | VALUE | |
|---|---|---|
| FOOD NAME | SOUP DUMPLING | 2403, 2400 |
| FLOUR | 5 g | |
| GROUND PORK | 10 g | ← BAD |
| ONION | 5 g | |
| HONEY | 1 g | |
| CHICKEN STOCK | 10 g | ← BAD |
| SESAME SEEDS | 0.5 g | |

FIG. 25

| FIELD | VALUE |
|---|---|
| FOOD NAME | RAMEN AND VEGETABLE GYOZA |
| SHOYU RAMEN | 1 |
| VEGETABLE GYOZA | 3 |

2404, 2400

| FIELD | VALUE |
|---|---|
| FOOD NAME | SHOYU RAMEN |
| FLOUR | 50 g |
| SALT | 5 g |
| STARCH | 1 g |
| SOY SAUCE | 10 g |
| OYSTER SAUCE | 1 g |
| SESAME SEEDS | 0.5 g |
| BOK CHOY | 12 g |
| WATER | 400 g |

2405, 2400

| FIELD | VALUE |
|---|---|
| FOOD NAME | VEGETABLE GYOZA |
| FLOUR | 5 g |
| CHINESE LEEK | 10 g |
| ONION | 5 g |
| CABBAGE | 15 g |
| HONEY | 2 g |
| SESAME SEEDS | 0.5 g |

2406, 2400

METHOD, INFORMATION TERMINAL, AND NON-TRANSITORY COMPUTER-READABLE RECORDING MEDIUM THAT CUSTOMIZE MENU INFORMATION BASED ON RELIGION INFORMATION

BACKGROUND

1. Technical Field

The present disclosure relates to a method of controlling an information terminal and the like.

2. Description of the Related Art

Japanese Unexamined Patent Application Publication No. 2005-222191 discloses a technology that offers a menu compatible with personal data on the basis of personal data including user preference information, dangerous ingredient information expressing ingredients the user is prohibited from consuming, and health management information for managing intake.

Japanese Unexamined Patent Application Publication No. 2008-299821 discloses a restaurant order reception device, installed in a restaurant, for assisting service work by accepting the input of order information from a menu and the like. The restaurant order reception device in Japanese Unexamined Patent Application Publication No. 2008-299821 is provided with a means for causing a display device to display an order input screen on which menu order information is imputable. On the order input screen, menu order information is inputted for each individual seat set at a table.

SUMMARY

One non-limiting and exemplary embodiment provides further improvement over the related art.

In one general aspect, the techniques disclosed here feature a method of controlling an information terminal of a user that communicates over a network with a first server that manages religion information of the user corresponding to identification information that identifies the user, the method comprising: acquiring a restaurant ID corresponding to a restaurant and a seat ID indicating a seat of the user through a first operation screen displayed on a display of the information terminal of the user, wherein the first operation screen conforms to a common style designed by a matching app of the first server; acquiring, on a basis of the restaurant ID, menu information indicating one or more foods provided by the restaurant over a network from a second server associated with the restaurant corresponding to the restaurant ID; extracting one or more first foods corresponding to the religion information at the information terminal on a basis of the menu information and the religion information; displaying the one or more first foods through a second operation screen for accepting an order of a food to be provided by the restaurant, wherein the second operation screen is customized according to a style designated by the restaurant; and transmitting from the information terminal to the second server i) food order information indicating the food selected from among the one or more first foods using the second operation screen and ii) the seat ID.

According to the above aspect, further improvements may be achieved.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 22 is a table summarizing various religions and ingredients that users should avoid according to each religion;

FIG. 23 is a diagram illustrating an example of a data structure of information including user religion information returned from a first server to the matching app;

FIG. 24 is a diagram illustrating an example of a data structure of ingredient information forming menu information returned from a second server;

FIG. 25 is a diagram illustrating an example of ingredient information for ramen and vegetable gyoza;

Figure 1:
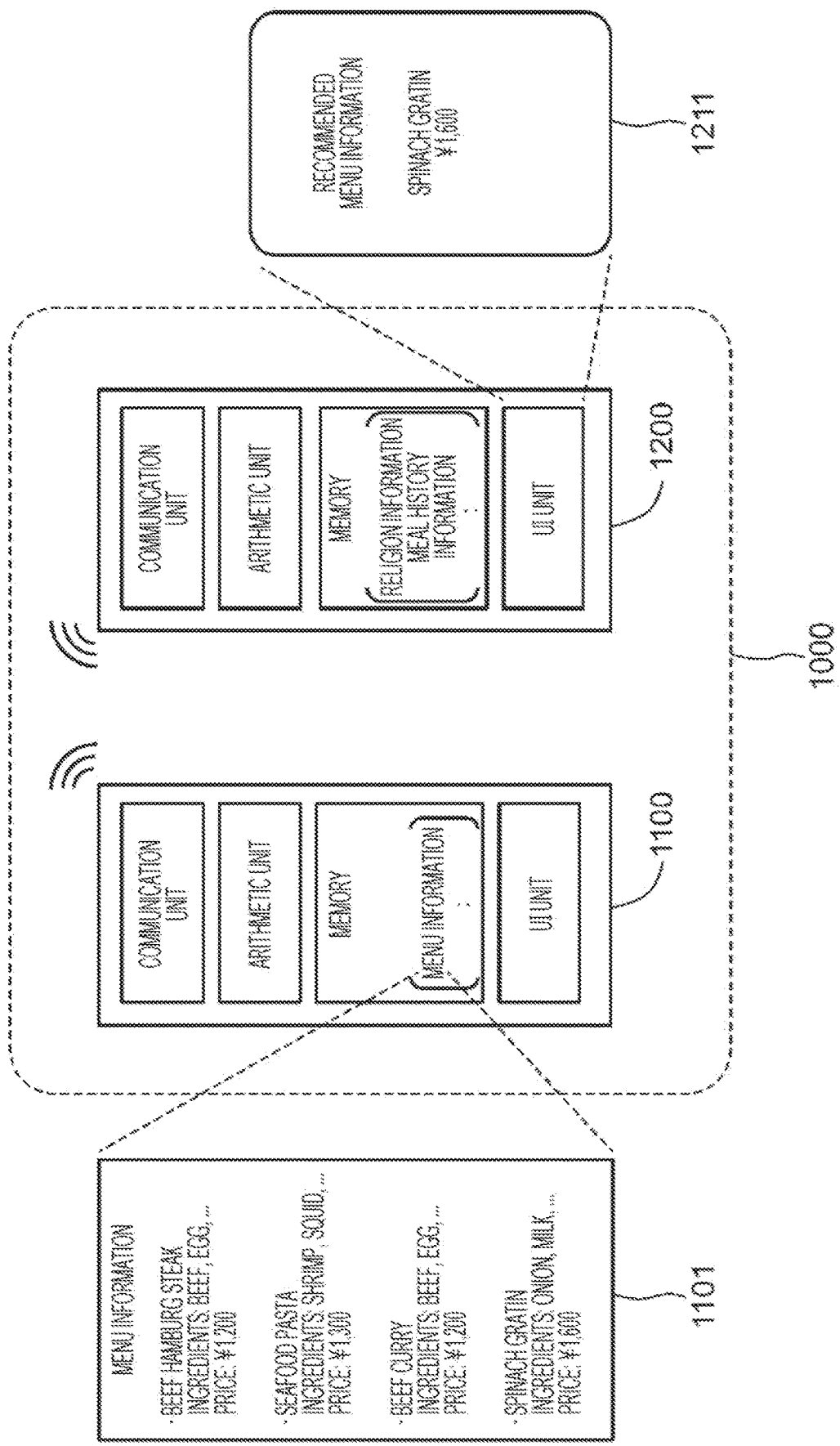
FIG. 1 is a diagram illustrating a configuration of a typical food ordering system.

DETAILED DESCRIPTION (Background Leading Up to the Present Disclosure)

In Japan, the effects of the tourism boom in recent years has led to an increase in visits by foreigners adhering to a variety of religions. Each religion has its own doctrine, and depending on the doctrine, ingredients that should be avoided are prescribed. In light of such circumstances, if a restaurant could offer a menu that mainly includes consumable foods with consideration for the customer's religion, customer satisfaction would be improved and the restaurant would be able to differentiate itself from other restaurants.

However, there are a variety of religions around the world, such as Islam, Christianity, Buddhism, Hinduism, and Judaism, and the ingredients that should be avoided are different for each religion. Furthermore, in some cases, the ingredients that should be avoided are different depending on the sect within the same religion. Consequently, it is not easy to offer an appropriate menu according to the religion and sect embraced by a customer.

In addition, if the food ordered by a certain customer is mistakenly served to the seat of another customer of a different religion sitting at the same table, and moreover if the food contains an ingredient that should be avoided by the other customer for religious reasons, the other customer will be discomforted. Furthermore, if the other customer eats the food without realizing what the food contains, there is a risk that the other customer's health may be impaired as a result of eating an ingredient that he or she is unaccustomed to eating. Consequently, it is necessary to avoid such serving mistakes.

Japanese Unexamined Patent Application Publication No. 2005-222191 described above discloses that a user is made to input a user ID and a password into a menu terminal provided at each table in a certain store, a store server acquires personal data about the user and store data about the store from a data center, the store server determines a menu from which problematic ingredients (dangerous ingredients and disliked ingredients) have been removed and a recommended menu (such as a menu containing many foods that the user likes) on the basis of the personal data and the store data, and the menu terminal displays the determined menu.

However, in Japanese Unexamined Patent Application Publication No. 2005-222191, as is apparent from how a unique table number if set for each table in the menu terminal, food orders are only considered in units of tables, and there is no consideration for food orders at the seat level. For this reason, with Japanese Unexamined Patent Application Publication No. 2005-222191, there is a possibility that a serving mistake will occur in which the food ordered by a certain customer is mistakenly served to another customer of a different religion sitting at the same table.

On the other hand, personal data such as preference information is sensitive information, and therefore it is inappropriate to provide such information to third parties without the user's consent.

However, in Japanese Unexamined Patent Application Publication No. 2005-222191, because personal data about the user is transmitted from the data center to the store server, there is also a problem of the personal data being provided to the store side without the user's consent.

Japanese Unexamined Patent Application Publication No. 2008-299821 discloses an order input screen on which it is possible to input and register, with an input device, food order information for each individual seat set at individual tables. The order input screen includes a seat position image including seat objects indicating a plurality of seats and a plurality of food-specifying images corresponding to each food item. For example, an employee touches the seat object of a desired seat from the seat position image, and then touches a food-specifying image corresponding to a desired food item. With this arrangement, the food item individually ordered by the customer sitting in the touched seat is selected.

Figure 38:
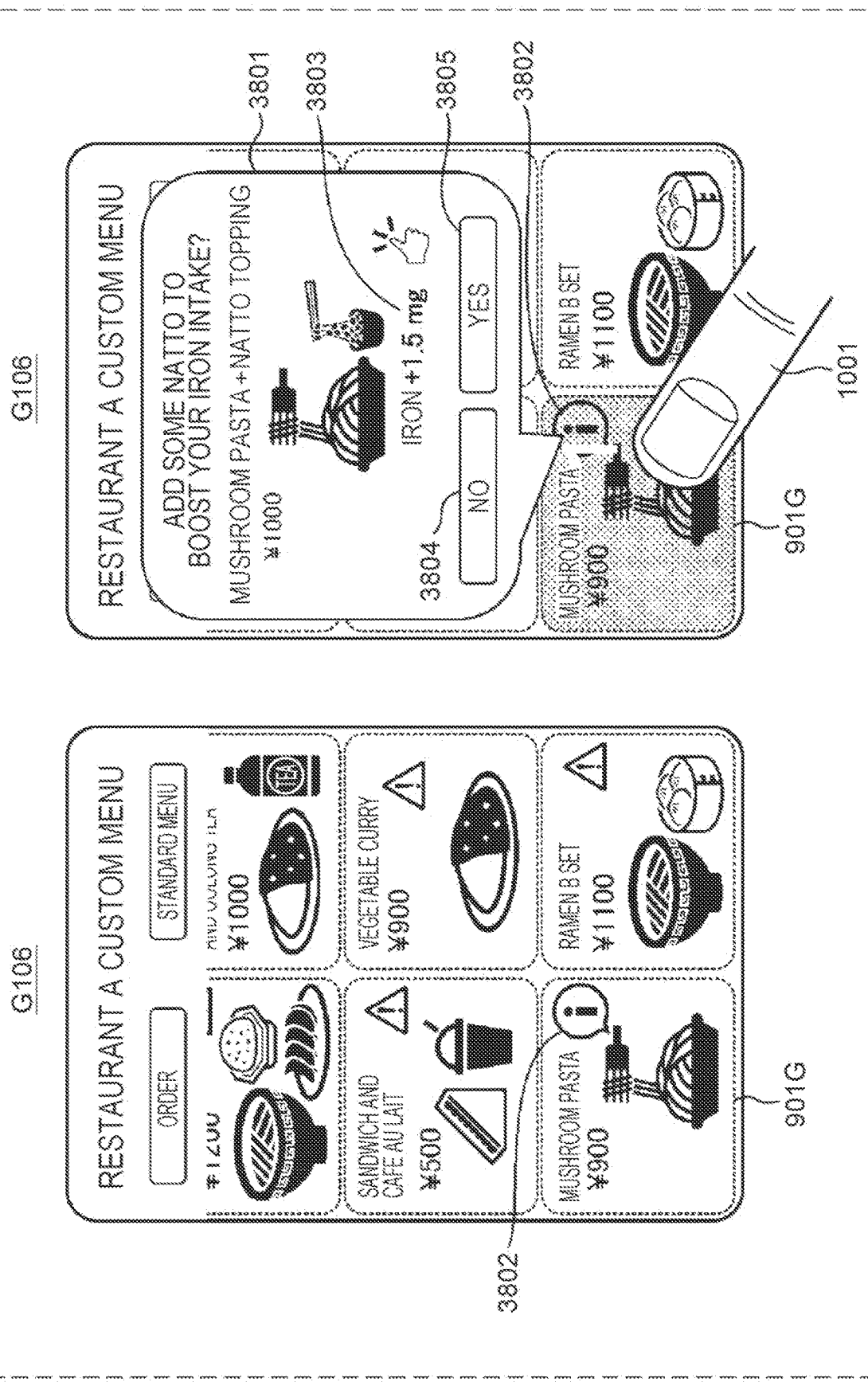
FIG. 38 is a diagram illustrating an example of an operation screen including a third variation of the personalized menu.

In this way, in Japanese Unexamined Patent Application Publication No. 2008-299821, a seat and a food item are associated by manual input by an employee through the order input screen. For this reason, there is a possibility of incorrect input occurring when associating a seat with a food item. In particular, such incorrect input occurs easily at times when the store is crowded. Furthermore, the order input screen in Japanese Unexamined Patent Application Publication No. 2008-299821 includes various information and objects besides the seat position image and the food-specifying images, as illustrated in FIG. 38 of Japanese Unexamined Patent Application Publication No. 2008-299821. The above also demonstrates that there is a high probability that such incorrect input may occur on the order input screen of Japanese Unexamined Patent Application Publication No. 2008-299821. For this reason, like Japanese Unexamined Patent Application Publication No. 2005-222191, Japanese Unexamined Patent Application Publication No. 2008-299821 is also unable to prevent the serving mistakes described above.

The present disclosure has been devised to address the issues described above, and a first objective thereof is to prevent food ordered by a certain customer from being served to another customer of a different religion.

Furthermore, a second objective of the present disclosure is to prevent sensitive information stored in a first server from being leaked outside the first server without the user's consent.

A control method according to an aspect of the present disclosure is a method of controlling an information terminal of a user that communicates over a network with a first server that manages religion information of the user corresponding to identification information that identifies the user, the method comprising: acquiring a restaurant ID corresponding to a restaurant and a seat ID indicating a seat of the user through a first operation screen conforming to a common style designated by a matching app displayed on a display of the information terminal of the user, wherein the first operation screen conforms to a common style designed by a matching app of first server; acquiring, on a basis of the restaurant ID, menu information indicating one or more foods provided by the restaurant over a network from a second server associated with the restaurant corresponding to the restaurant ID; extracting one or more first foods corresponding to the religion information at the information terminal on a basis of the menu information and the religion information; displaying the one or more first foods through a second operation screen for accepting an order of a food to be provided by the restaurant, wherein the second operation screen is customized according to a style designated by the restaurant; and transmitting ID from the information terminal to the second server i) food order information indicating the food selected from among the one or more first foods using the second operation screen and ii) the seat.

According to the above aspect, when ordering a food, a first operation screen is displayed on a display of a user's information terminal, and a restaurant ID indicating a restaurant compatible with a religion indicated by religion information corresponding to identification information and a seat ID indicating the user's seat are acquired through the first operation screen. On the basis of the acquired restaurant ID, menu information indicating one or more foods provided by the restaurant corresponding to the restaurant ID is acquired from a second server.

One or more first foods corresponding to the religion information are extracted on the basis of the acquired menu information and the religion information of the user. The one or more extracted first foods are displayed on the display of an information terminal through a second operation screen for receiving an order of food from the restaurant. A food is selected from among the one or more first foods displayed on the second operation screen, and food order information indicating the food is associated with the seat ID and transmitted to the second server.

In this way, in this aspect, the food order information indicating the food selected by the user from a personalized menu and the user's seat are associated automatically without manual intervention as part of the process by which the user orders the food. This arrangement makes it possible to prevent a serving mistake in which the food ordered by a certain user contains an ingredient that should be avoided for religious reasons by another user sitting at the same table, but the food is mistakenly served to other user, for example. As a result, it is possible to prevent discomfort to the other user. Furthermore, because such serving mistakes are prevented, it is possible to prevent an impairment to the health of the other user caused by the other user mistakenly eating the served food.

Furthermore, in this aspect, because the religion information is not transmitted to the second server, the religion information is prevented from being leaked to the restaurant side. Furthermore, in this aspect, because the food order information is transmitted in association with the seat ID rather than the identification information that specifies the user, the identification information is prevented from being leaked to the restaurant side.

Furthermore, in this aspect, because the first operation screen corresponds to the first server, the design of the first operation screen can be made to reflect the intentions of the manager of the first server. Meanwhile, because the second operation screen corresponds to the second server, the design of the second operation screen can be made to reflect the intentions of the manager of the second server.

In the above method, the one or more first foods may also be foods excluding a second food that is not compatible with the religion information.

According to this aspect, because the second operation screen excluding foods that are incompatible with the religion information is generated, the user is able to order a food smoothly.

In the above method, the one or more first foods may include a food with an added ingredient containing a nutrient that tends to be deficient in correspondence with the religion indicated by the religion information.

According to this aspect, because the one or more first foods include a food with an added ingredient containing a nutrient that tends to be deficient in correspondence with the religion indicated by the religion information, it is possible to suggest to the user a food capable of supplying a nutrient that tends to be deficient but is difficult to specify because specialized knowledge is demanded.

In the above method, the second operation screen may also include a display indicating a side menu for supplying a nutrient that tends to be deficient in correspondence with the religion indicated by the religion information.

According to this aspect, because a side menu for supplying a nutrient that tends to be deficient in correspondence with the religion indicated by the religion information is displayed on the second operation screen, it is possible to suggest to the user a combination of foods capable of supplying a nutrient that tends to be deficient but is difficult to specify because specialized knowledge is demanded.

In the above method, the one or more first foods may include a food with an added ingredient containing a nutrient in which the user has been deficient in past meals consumed by the user over a predetermined period.

According to this aspect, because the one or more first foods include a food with an added ingredient containing a nutrient in which the user has been deficient in past meals consumed by the user over a predetermined period, it is possible to suggest to the user a food capable of supplying a nutrient that has been deficient in the predetermined period but is difficult to specify because specialized knowledge is demanded.

In the above method, the second operation screen may also include a display indicating a side menu for supplying a nutrient in which the user has been deficient in past meals consumed by the user over a predetermined period.

According to this aspect, because the second operation screen includes a display indicating a side menu for supplying a nutrient in which the user has been deficient in past meals consumed by the user over a predetermined period, it is possible to suggest to the user a combination of foods capable of supplying a nutrient that has been deficient but is difficult to specify because specialized knowledge is demanded.

In the above method, the religion information of the user may include the religion of the user as well as level information indicating the degree to which to avoid an ingredient that should be avoided according to the religion.

According to this aspect, the religion information includes the religion of the user as well as level information indicating the degree to which to avoid an ingredient that should be avoided according to the religion indicated by the religion information. Consequently, the priority of each food included in the menu information can be determined finely and a personalized menu can be generated with consideration for the religion embraced by the user as well as the degree to which an ingredient should be avoided.

In the above method, foods containing an ingredient that the user should avoid as much as possible may also be included.

According to this aspect, because the personalized menu includes foods containing an ingredient that the user should avoid as much as possible, a personalized menu can be generated to meet the needs of users who do not strictly adhere to the doctrine of the religion.

In the above method, the identification information may also include a user ID.

According to this aspect, because the identification information includes a user ID, the religion information corresponding to the user can be acquired with certainty from the first server.

In the above method, the first server may also be distinct from the second server.

Sensitive information about the user, such as the religion information of the user, is stored in the first server. It is not preferable for such sensitive information to be provided outside the first server without the user's consent. In this aspect, the first server is configured as a distinct server from the second server. Consequently, sensitive information about the user is prevented from being leaked outside the first server.

In the above method, the restaurant ID and the seat ID may also be acquired through the first operation screen by reading an identification code prepared at a corresponding position at the table where the user sits.

According to this aspect, the restaurant ID and the seat ID are acquired by reading an identification code prepared at a corresponding position at the table where the user sits. With this arrangement, the restaurant ID and the seat ID can be acquired without being input manually by the user.

In the above method, the identification code may include a QR code.

According to this aspect, because the identification code is a QR code, the information can be acquired without being input manually by the user.

In the above method, the identification code may also be read using Near Field Communication (NFC).

According to this aspect, because the identification code is read using NFC, the information can be acquired without being input manually by the user.

In the above control method, the first server may also distributively manage the religion information, biometric information, preference information including product purchase history information or food order history information about the user, and activity history information including position information about the user.

According to this aspect, because the religion information, the biometric information, the purchase history information or preference information, and the activity history information is distributively managed, the first server is capable of acquiring personal information about the user as needed. As a result, this aspect makes it possible to preserve the freshness of the personal information stored in the first server, and thereby prevent a personalized menu from being created on the basis of outdated religion information.

A method according to another aspect of the present disclosure is a method of controlling an information terminal of a user that communicates over a network with a first server that manages religion information of the user corresponding to identification information that identifies the user, the method comprising: transmitting the identification information stored in the information terminal to the first server; acquiring, from the first server on a basis of position information and the identification information of the information terminal through a 1st first operation screen displayed on a display of the information terminal of the user, restaurant information expressing one or more restaurants which exist in an area including a point indicated by the position information and which are compatible with a religion indicated by religion information corresponding to the identification information, wherein the 1st first operation screen conforms to a common style designed by a matching app of the first server; acquiring a restaurant ID corresponding to one a restaurant from among the one or more restaurants and a seat ID indicating a seat of the user through a 2nd first operation screen displayed on the display of the information terminal of the user, wherein the 2nd first operation screen conforms to the common style designed by the matching app of the first server; acquiring, on a basis of the restaurant ID, menu information indicating one or more foods provided by the one restaurant over a network from a second server associated with the one restaurant corresponding to the restaurant ID; extracting one or more first foods corresponding to the religion information at the information terminal on a basis of the menu information and the religion information; displaying the one or more first foods through a second operation screen for accepting an order of a food to be provided by the restaurant, wherein the second operation screen is customized according to a style designated by the restaurant; and transmitting from the information terminal to the second server i) food order information indicating the food selected from among the one or more first foods using the second operation screen and ii) the seat ID.

According to this aspect, when ordering rood, a 1st first operation screen is displayed on the display of the user's information terminal. Through the 1st first operation screen, one or a plurality of restaurant information about restaurants which exist in an area including a point indicated by the position information about the information terminal and which are compatible with the religion indicated by the religion information corresponding to the identification information is acquired from the first server.

A 2nd first operation screen is displayed on the display of the information terminal. Through the 2nd first operation screen, a restaurant ID and a seat ID of one restaurant among the one or plurality of restaurant information are acquired. From the acquired restaurant ID, menu information indicating one or more foods provided by the restaurant corresponding to the restaurant ID is acquired from the second server.

A personalized menu for the user corresponding to the religion information is generated on the basis of the acquired menu information and the religion information of the user. The personalized menu is displayed on the display of the information terminal through the second operation screen. A food is selected from the displayed personalized menu, and food order information indicating the food is associated with the seat ID and transmitted to the second server.

In this way, in this aspect, the food order information indicating the food selected by the user from a personalized menu and the user's seat are associated automatically without manual intervention as part of the process by which the user orders the food. This arrangement makes it possible to prevent a serving mistake in which the food ordered by a certain user contains an ingredient that should be avoided for religious reasons by another user sitting at the same table, but the food is mistakenly served to other user, for example. As a result, it is possible to prevent discomfort to the other user. Furthermore, because such serving mistakes are prevented, it is possible to prevent an impairment to the health of the other user caused by the other user mistakenly eating the served food.

Furthermore, in this aspect, because the religion information is not transmitted to the second server, the religion information is prevented from being leaked to the restaurant side. Furthermore, in this aspect, because the food order information is transmitted in association with the seat ID rather than the identification information that specifies the user, the identification information is prevented from being leaked to the restaurant side.

Furthermore, in this aspect, because restaurant information about one or more restaurants near the user and compatible with the user's religion is acquired through the 1st first operation screen, the user is able to select a restaurant compatible with his or her own religion smoothly.

Furthermore, in this aspect, because the 1st first operation screen and the 2nd first operation screen correspond to the first server, the design of both operation screens can be made to reflect the intentions of the manager of the first server. Meanwhile, because the second operation screen corresponds to the second server, the design of the second operation screen can be made to reflect the intentions of the manager of the second server.

In the above method, the position information about the user's information terminal may also be acquired in the first server by using a GPS system.

According to this aspect, the position information about the user's information terminal can be acquired accurately.

The above method may also be executed in the information terminal. The above method may also be a program executed by a computer in the information terminal, or a recording medium storing the program.

According to these configurations, an information terminal and a program that execute the method described above can be provided.

In the above program, the identification information that specifies the user may also include a serial code for each information terminal assigned to the program.

According to this configuration, because a serial code for each information terminal assigned to the program is adopted, the identification information can be configured as information with a higher degree of anonymity.

Embodiment

The Internet is expected to become even more widespread in society in the future, with various types of sensors becoming commonplace. Accordingly, in society, information related to the states and activities of individuals as well as information about a city as a whole, including features such as buildings and traffic, is anticipated to become digitized and usable by computer systems. Digitized data related to individuals (personal information) is accumulated in the cloud through communication networks, managed in information banks as big data, and used for various purposes for individuals.

Such a highly information-oriented society is referred to as Society 5.0 in Japan. A highly information-oriented society is one in which economic advancement and the resolution of social issues are anticipated through an information infrastructure (cyber-physical system) that highly integrates real space (physical space) and virtual space (cyberspace).

In such a highly information-oriented society, when an individual makes decisions in various daily scenarios, big data including accumulated personal information is analyzed to enable the individual to know which choices are considered optimal for the individual according to the situation at the time.

Hereinafter, individual eating habits will be treated as a theme to describe a configuration that achieves improved economic efficiency and individual optimization (personalization) in a highly information-oriented society in which such a cyber-physical system operates.

As an example of a personalized food ordering system, it is conceivable to transmit menu information from a store terminal of a restaurant to an information terminal of an individual, and present a menu of foods that do not contain ingredients that should be avoided by the user for religious reasons on a mobile terminal as a recommended menu. First, a typical food ordering system expected to be constructed in a society before the highly information-oriented society described is proposed will be described.

FIG. 1 is a diagram illustrating a configuration of a typical food ordering system. The ordering system includes a store terminal 1100 and a mobile terminal 1200. The store terminal 1100 and the mobile terminal 1200 are installed inside a restaurant location (hereinafter referred to as a "store")

1000. The store terminal 1100 is a computer that transmits menu information. The store terminal 1100 includes a communication unit for communicating with external equipment, an arithmetic unit for performing arithmetic processing, a memory for storing data, and a UI unit for displaying and manipulating information. The memory stores menu information 1101. The menu information 1101 includes information related to foods that the restaurant provides. Specifically, the menu information 1101 includes the names of foods, the ingredients used in the foods, and the prices of the foods. In the example of FIG. 1, the menu information 1101 includes the four foods of beef Hamburg steak, seafood pasta, beef curry, and spinach gratin.

The mobile terminal 1200 is a mobile terminal such as a smartphone carried by a user visiting the store 1000. The mobile terminal 1200 includes a communication unit for communicating with external equipment, an arithmetic unit for performing arithmetic processing, a memory for storing data, and a UI unit for displaying and manipulating information. The memory stores information such as religion information and meal history information about the user corresponding to identification information of the user who carries the mobile terminal 1200. The religion information includes information related to ingredients that should be avoided by the user according to the religion embraced by the user.

When the user enters the store 1000, the store terminal 1100 and the mobile terminal 1200 initiate communication automatically or manually. The mobile terminal 1200 that has initiated communication acquires the menu information 1101 from the store terminal 1100. The mobile terminal 1200 acquiring the menu information 1101 cross-references the menu information with the religion information stored in the memory, and extracts foods that do not contain ingredients that should be avoided. The mobile terminal 1200 generates a recommended menu 1211 on the basis of the extracted foods, and displays the recommended menu 1211 on the UI unit. In the example of FIG. 1, beef is an ingredient that should be avoided by the user, and therefore the food that does not contain beef, namely spinach gratin, is displayed as the recommended menu 1211.

According to the above configuration, the user is able to select, from the displayed recommended menu, a food that does not contain an ingredient that should be avoided.

In Society 5.0, personal information such as religion information is anonymized such that an individual is not identified by a third party and managed exclusively by a server of a business referred to as an information bank that manages personal information. The personal information is continually updated under the management of the information bank, without depending on manual input from the user.

However, in the ordering system illustrated in FIG. 1, the religion information is managed by the mobile terminal 1200 and is not managed by a server. Consequently, in the ordering system illustrated in FIG. 1, updating the religion information is not easy. For example, updating the religion information involves requesting the user to manually input religion information into the mobile terminal 1200, which is burdensome for the user. Furthermore, because the religion information is not anonymized, there is also a possibility that the religion information may be leaked to the store terminal 1100. Consequently, further improvements are needed to make the ordering system illustrated in FIG. 1 compatible with the highly information-oriented society called for by Society 5.0. Accordingly, the present embodiment proposes an information processing system in accordance with Society 5.0. Hereinafter, the information processing system according to the embodiment of the present disclosure will be described with reference to the drawings.

Figure 2:
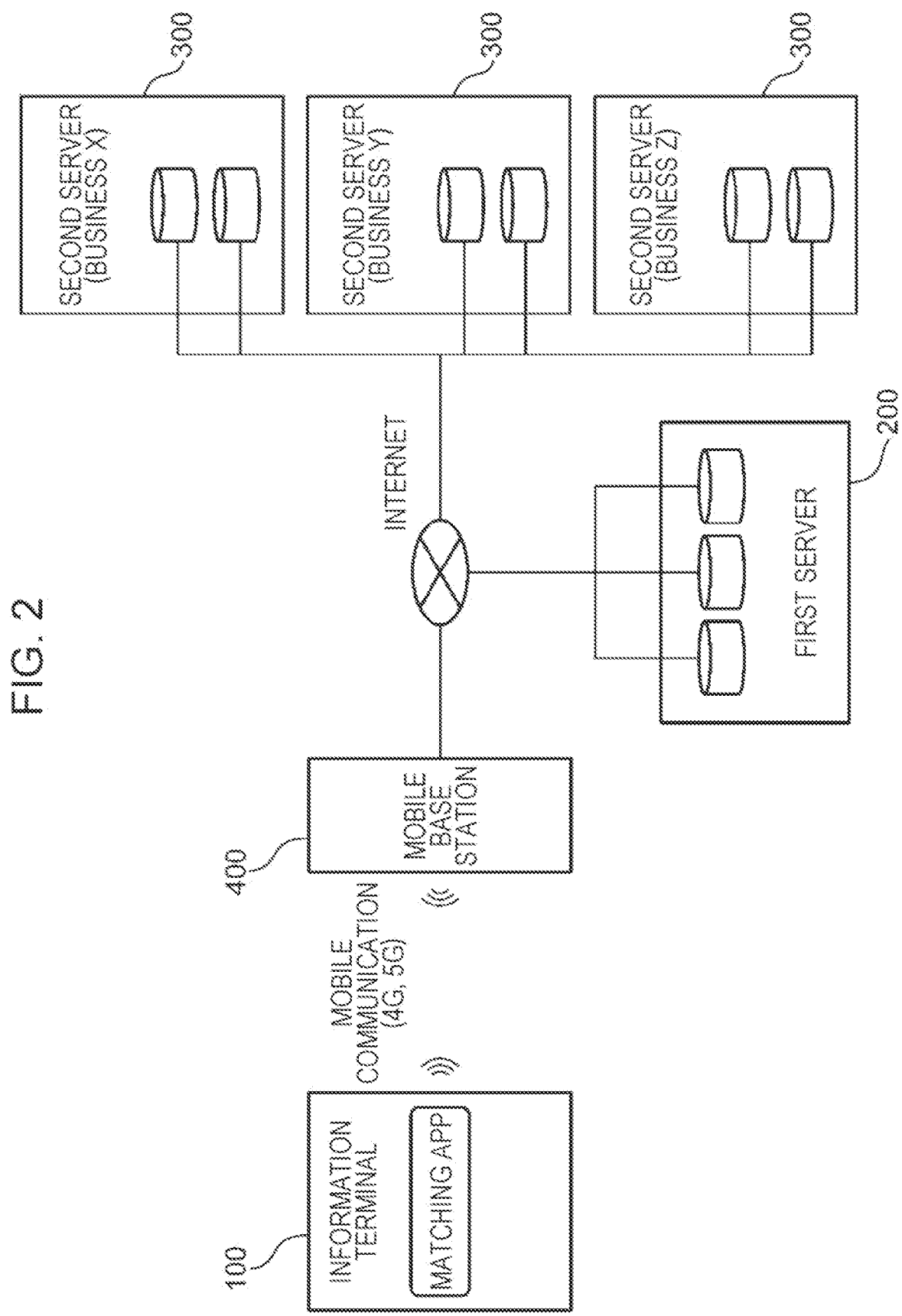
FIG. 2 is a diagram illustrating an example of an overall picture of the information infrastructure of an information processing system according to the present disclosure.

FIG. 2 is a diagram illustrating an example of an overall picture of the information infrastructure of the information processing system according to the present disclosure. The information processing system in FIG. 2 is a system configured in accordance with Society 5.0, and is a system that provides a selection assistance service that uses personal information to suggest a product or service suited to a user acting as a consumer, and thereby helps the user to select a product or service. The present embodiment mostly focuses on a service that assists with ordering a food as the selection assistance service, but before describing the service, FIG. 2 will be used to describe an overall picture of the information infrastructure for achieving the present embodiment. The information processing system is roughly divided into three equipment groups.

The first equipment group includes an information terminal 100 such as a smartphone carried by the user. A matching application is installed on the information terminal 100. The matching application (hereinafter referred to as the matching app) is an application for choosing or recommending a product or service suited to the user by using personal information about the user. The personal information referred to herein broadly encompasses publicly disclosed and non-publicly disclosed information related to an individual. For example, the personal information includes at least one of a name, a birth date, a home address, an annual income, owned property/real estate information, physical information such as height/weight, genetic information, religion information, medical information such as a medical history/medical records, activity information such as a number of steps/burned calories, meal history information, vital sign information such as heart rate/blood pressure, purchase information about purchases made at stores/EC sites or the like, keyword information used to perform searches through a Web search engine/AI speaker, text/audiovisual information transmitted or received through email/SNS, or movement history information. The information terminal 100 is connectible to the Internet through a mobile base station 400 by mobile communication referred to as 4G or 5G, for example.

The second equipment group includes a first server 200. The first server 200 is a personal information server in which the user's personal information is distributed among multiple locations, and the distributed personal information is additionally encrypted and stored. For example, the first server 200 manages the personal information by fragmenting and encrypting the user's personal information for storage on a plurality of storage devices in the cloud. With this arrangement, a high level of security is ensured, and the leakage or the like of the personal information is prevented. Furthermore, the first server 200 has a function of returning relevant data in response to a query from a third party, according to the consent of the user in question. Furthermore, the first server 200 has a function of securely sharing personal information for which the user has given consent with a business for which the user has given consent. In other words, the first server 200 functions as an information bank. In this case, the first server 200 distributively records a single piece of data in a plurality of storage devices, for example. An example of a single piece of data is a single file in which personal information is recorded.

In the present embodiment, the first server 200 shares specific personal information with a specific business on the basis of consent by the user. Furthermore, the first server 200 has a function for providing the selection assistance service described below.

The matching app described above is developed and/or distributed by the company that manages the first server 200, for example. The managing company uses the user's personal information to evaluate the user's compatibility with respect to a product or service that the user may possibly use. The company that manages the first server 200, the company that develops the matching app, and the company that distributes the matching app may be the same company or different companies. The information processing system illustrated in FIG. 2 uses the matching app described above to achieve the selection assistance service, but this is merely an example. For instance, the selection assistance service may also be achieved by using an app other than the matching app, a typical browser, or the like. To handle the user's personal information securely, it is preferable to provide the selection assistance service through a dedicated app such as the matching app. However, this is merely an example, and in the case of handling personal information with a low level of security, such as publicly disclosed personal information for example, or in the case where a function for ensuring security is provided, the selection assistance service may also be provided by a means other than the matching app.

The matching app only handles personal information internally in the information terminal 100. For example, the matching app presents products or services thought to be optimal for the user under given conditions such as the time, place, and circumstances. For example, the matching app provides an intermediary function for facilitating economic activity such as purchasing by the user.

The matching app that openly discloses recommendation functions that have hitherto been siloed for each service business. An example will be described in terms of an electronic transaction marketplace such as an EC site, which is one well-known example of a service business. Many products are listed on the websites of such a service business. If a user searches for or buys a specific product, other products correlated with the specific product (for example, products that are often purchased together) are recommended to the user. Such a recommendation function related to purchasing is only valid on the EC site of that service business. Consequently, the recommendation function does not exhibit any effect when the user buys a product on an EC site operated by another service business, orders food at a restaurant, or plans a family trip for the holidays.

In the future, it is expected that personal information will be aggregated in information banks, and a mechanism allowing anyone to access enormous and diverse personal information that is accurate over a long period under predetermined conditions will be established. In this case, it is possible to use a search or purchase history from an EC site of a certain service business as well as various personal information about the user to estimate the degree of compatibility with respect to all kinds of products and services, and not just the products offered by the service business. With this arrangement, it is possible to recommend products and services that are more valuable to the user from among various options.

To achieve a concept or function like the above, the first server 200 envisioned by the present embodiment is a general-purpose storage device provided in the cloud that distributes and encrypts personal information.

The third equipment group includes second servers 300 with which each business manages data specific to each business. In FIG. 2, three businesses referred to as Business X, Business Y, and Business Z each own or rent a second server 300 to manage and/or provide information related to each company's own products and/or each company's own services. The businesses are not limited to just dining businesses as described in detail in the present disclosure. For example, the businesses may also be home meal replacement businesses where prepared foods are available for takeout, such as caterers and fast food establishments. Furthermore, the businesses may also be home cooking-oriented businesses mainly focused on the preparation of food at home, such as supermarkets. Furthermore, the businesses may also be automobile manufacturers, real estate companies, hospitals and clinics, schools, tutoring schools for academic studies or sports, law offices, and businesses that provide products and/or services to general consumers.

One effect of the information processing system according to the present embodiment is that personal information is not handed over to a business. In an information bank, it is anticipated that the sharing of personal information with a specific business may be allowed on the basis of the consent of the person in question.

However, asking the user to make individual decisions about the management of personal information is highly burdensome. Even if the trustee decides on a data management policy, the user may be unable to specifically grasp which data is handed over to whom, and the user may feel a sense of uneasiness.

Accordingly, in the present embodiment, the business that manages the first server 200 is forbidden or restricted from using stored personal information, such as decrypting and interpreting personal information for example, unless the user gives consent.

Furthermore, in the case where an information bank or an information intermediary that manages personal information and provides the matching app under a strict privacy management policy enters the market, the user may enter into an agreement to receive services provided by the information bank or the information intermediary. This arrangement makes it possible to keep personal information from being handed over to another business.

The information processing system according to the present embodiment is one configuration of a management system for a next-generation information society capable of lowering the possibility that personal information including sensitive information may be divulged to a third party other than the person in question, and also using enormous amounts of ever-changing personal information to match the user with various services. Hereinafter, an information processing system will be described under the above assumptions.

Figure 3:
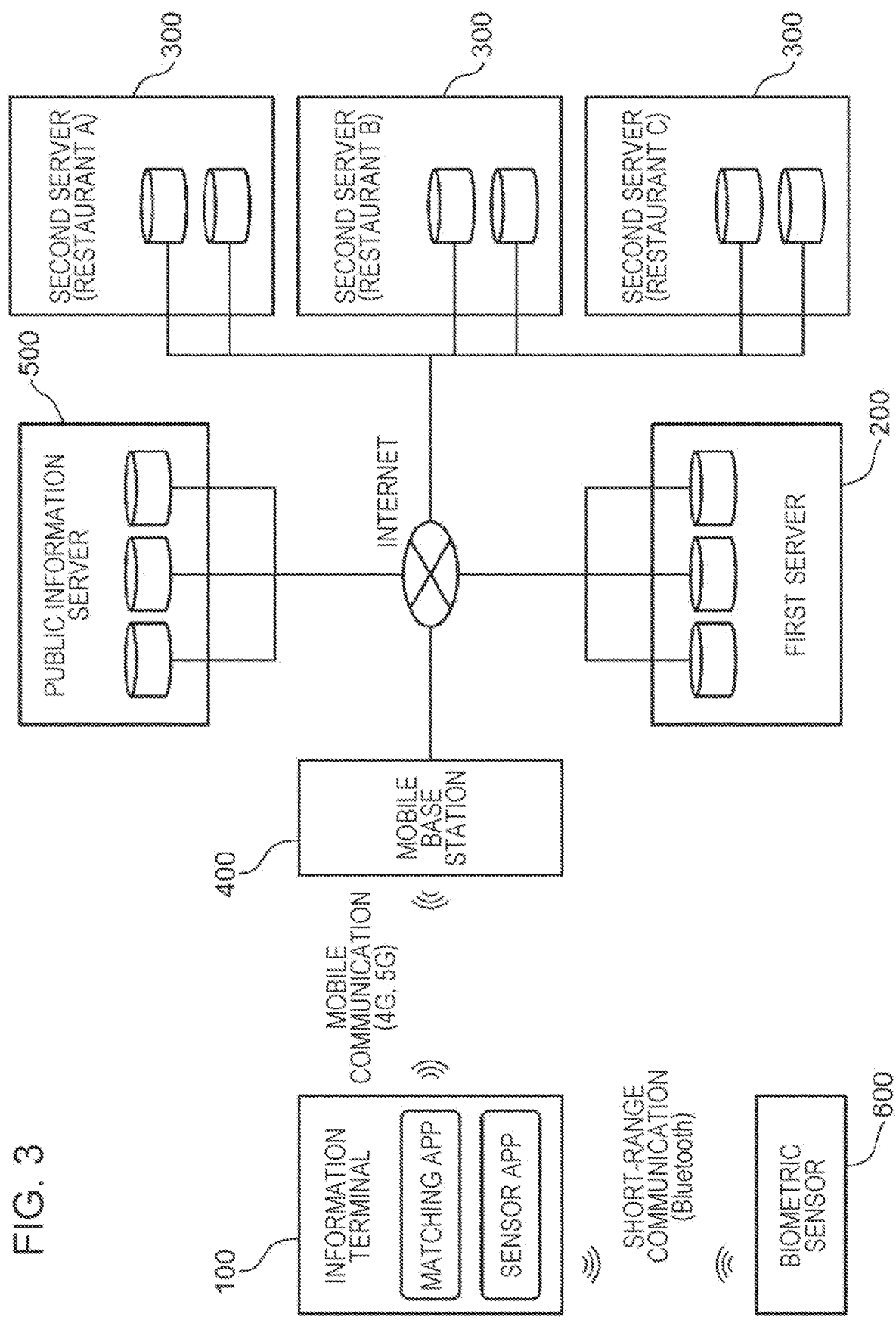
FIG. 3 is a diagram illustrating an overall picture of the information processing system according to the present embodiment in further detail.

FIG. 3 is a diagram illustrating an overall picture of the information processing system according to the present embodiment in further detail. The information processing system illustrated in FIG. 3 matches menu information that a user views to order a food when dining out with personal information about the user, and presents an optimal menu for the user. The information processing system illustrated in FIG. 3 includes the information processing system illustrated in FIG. 2 with the addition of a biometric sensor 600 and a public information server 500.

As the businesses on the service-providing side, companies in the dining industry referred to as Restaurant A, Restaurant B, and Restaurant C are assumed. Restaurant A, Restaurant B, and Restaurant C are respectively different companies. The information processing system illustrated in FIG. 3 includes a second server 300 managed by Restaurant A, a second server 300 managed by Restaurant B, and a second server 300 managed by Restaurant C. Menu information for each restaurant and information related to each store are managed by the second servers 300. The second servers 300 are cloud servers, for example.

The public information server 500 manages information related to restaurants and public information different from personal information. The public information server 500 is connected to the Internet. For example, the public information includes weather information and traffic information. The information is used appropriately when relevant to matching.

The biometric sensor 600 is a biometric sensor such as a smartwatch. The biometric sensor 600 is worn by the user carrying the information terminal 100. The biometric sensor 600 continually calculates vital sign information about the user. The various vital sign information calculated by the biometric sensor 600 is transmitted from the biometric sensor 600 to the information terminal 100 by short-range communication such as Bluetooth (registered trademark). The vital sign information is stored and/or managed by a sensor app installed in the information terminal 100. The sensor app uploads collected vital sign information and time information indicating the measurement time of the vital sign information to the first server 200 according to user account information. With this arrangement, the vital signal information is accumulated.

The sensor app may also grant access rights with respect to the data to be stored and/or managed to the matching app or an operating system (OS) of the information terminal 100. In this case, the vital sign information is uploaded to the first server 200 through the matching app or the OS. The sensor app may store the vital sign information in a memory of the information terminal 100, or upload the vital sign information to the first server 200 for storage.

Figure 4:
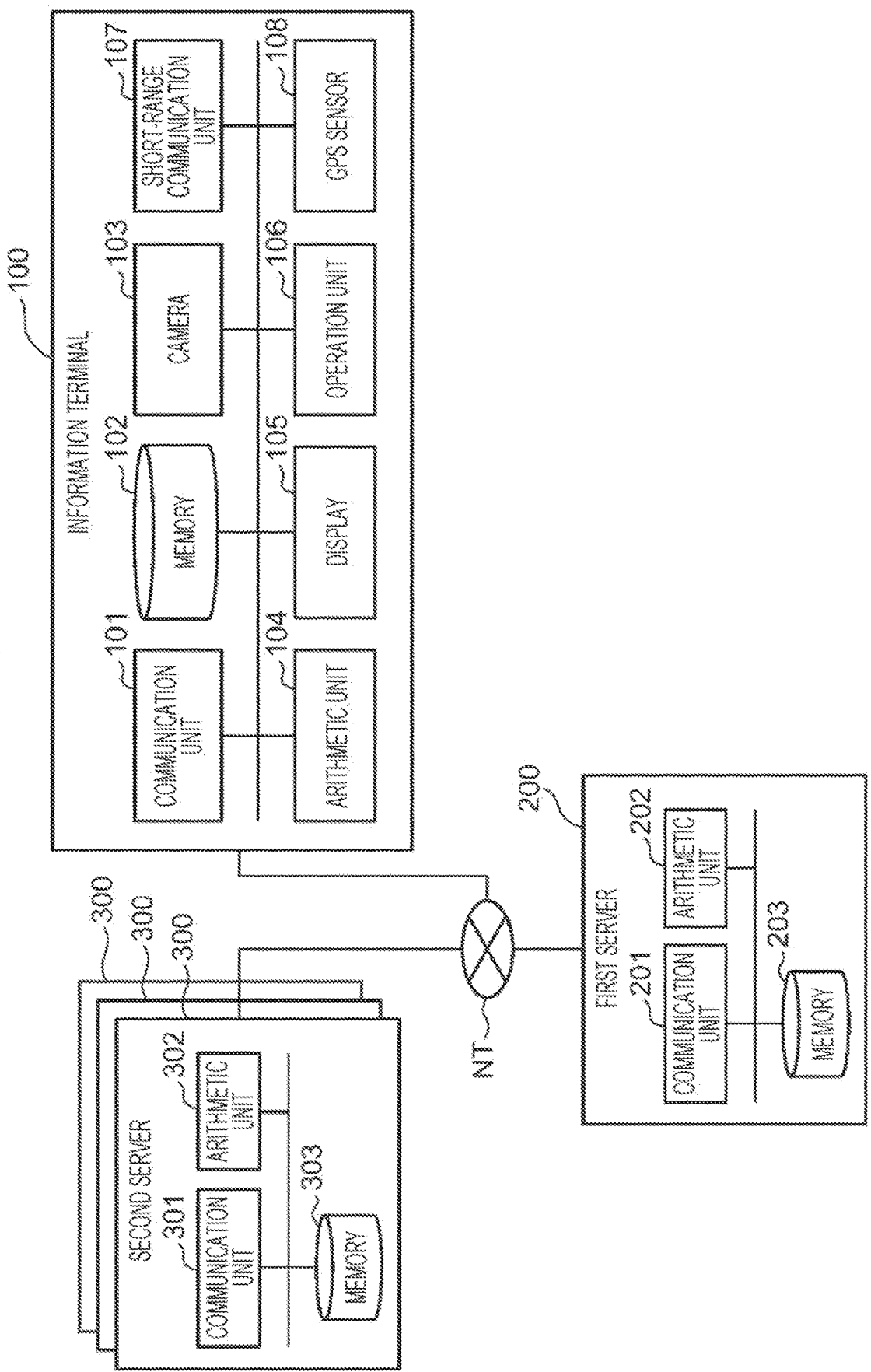
FIG. 4 is a diagram illustrating an example of a specific configuration of the information processing system according to the present embodiment.

FIG. 4 is a diagram illustrating an example of a specific configuration of the information processing system according to the present embodiment. The information processing system illustrated in FIG. 4 includes the information terminal 100, the first server 200, and the second servers 300 described with reference to FIGS. 2 and 3. Note that in FIG. 4, the mobile base station 400 and the biometric sensor 600 are omitted from illustration for convenience. The information terminal 100, the first server 200, and the second servers 300 are communicably interconnected through a network NT. The network NT is a wide area network, including a mobile phone communication network and the Internet.

The information terminal 100 is a portable information processing device such as a smartphone or tablet. In the present embodiment, the information terminal 100 is carried by a user who orders food at a restaurant location (that is, a store). The information terminal 100 includes a communication unit 101, a memory 102, a camera 103, an arithmetic unit 104, a display 105, an operation unit 106, a short-range communication unit 107, and a GPS sensor 108.

The communication unit 101 is a communication circuit that connects the information terminal 100 to the network NT. The communication unit 101 receives menu information described later that is transmitted from the second servers 300, and causes the received menu information to be stored in the memory 102. The arithmetic unit 104 performs a process of reading out the menu information stored in the memory 102. Additionally, the communication unit 101 receives religion information described later that is transmitted from the first server 200, and causes the received religion information to be stored in the memory 102. The arithmetic unit 104 performs a process of reading out the religion information stored in the memory 102. With this arrangement, the arithmetic unit 104 acquires the religion information and the menu information. Furthermore, under control by the arithmetic unit 104, the communication unit 101 transmits food order information described later and a seat ID described later in association with each other to one of the second servers 300.

The memory 102 is a non-volatile storage device such as flash memory. The memory 102 stores information 2300 including religion information as exemplified in FIG. 23 and ingredient information 2400 as exemplified in FIGS. 24 and 25. One set of ingredient information 2400 corresponds to one food, and is information related to the ingredients used in the food. The menu information contains one or more sets of ingredient information 2400. The information 2300 and the ingredient information 2400 will be described in detail later. Moreover, the memory 102 stores identification information that specifies the user. The identification information includes a user identifier (ID). The user ID is an identifier for the user.

The camera 103 is an imaging device including a CMOS sensor or the like. The camera 103 is used to capture a QR code attached to a seat at a restaurant location (that is, a store).

The arithmetic unit 104 is a processor such as a CPU. The arithmetic unit 104 executes software such as the OS of the information terminal 100, the matching app described above, a QR code reader, and a browser.

Figure 15:
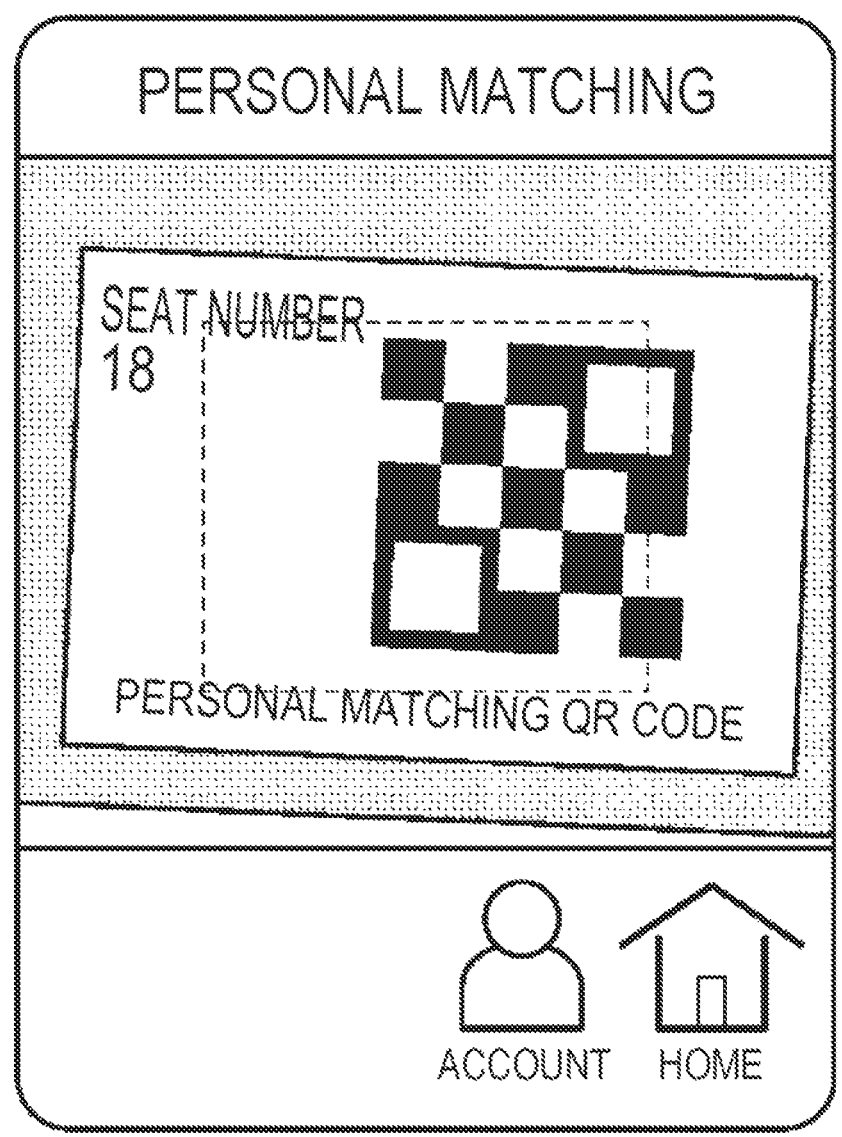
FIG. 15 is a diagram illustrating an example of an operation screen displayed on the information terminal in a case where the user who launched the matching app causes the information terminal to read a QR code corresponding to the user's seat.
Figure 16:
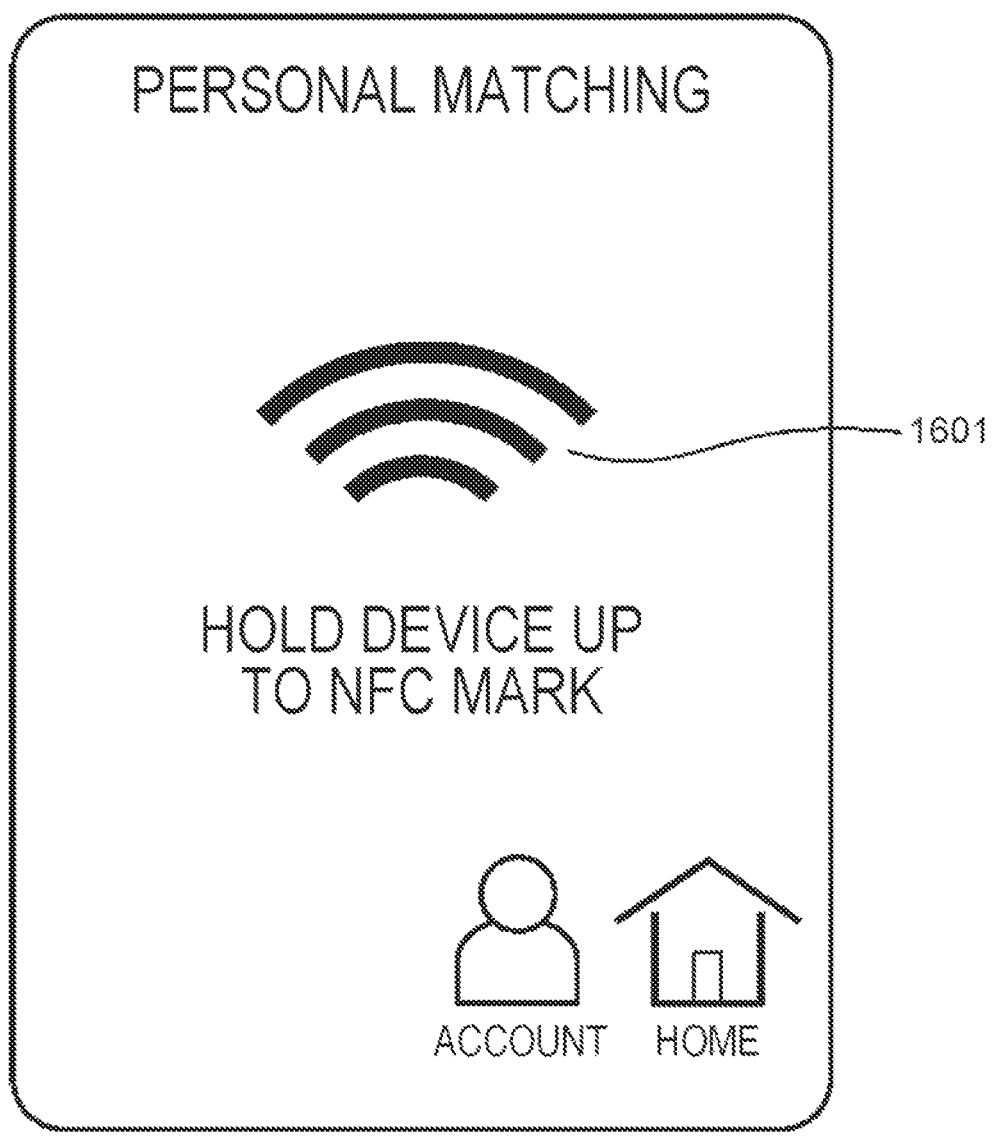
FIG. 16 is a diagram illustrating an example of an operation screen displayed on the information terminal in the case of acquiring a restaurant ID and a seat ID through NFC.

The arithmetic unit 104 acquires, through a first operation screen corresponding to the first server 200 and displayed on the display 105, a restaurant ID expressing a restaurant compatible with a religion indicated by the religion information corresponding to the identification information of the user and a seat ID indicating the user's seat. The first operation screen is an operation screen for reading a QR code provided by the matching app as illustrated in FIG. 15 or an operation screen for reading information by NFC as illustrated in FIG. 16, for example. The restaurant ID is an identifier for a restaurant. In the case where a restaurant has multiple locations (that is, stores), the restaurant ID may include an identifier for the restaurant and an identifier for the store. The seat ID is an identifier for a seat disposed in a store. The arithmetic unit 104 may acquire the restaurant ID and the seat ID by analyzing a QR code captured by the camera 103 when the user inputs a capture instruction into the operation unit 106. Alternatively, in the case where the information terminal 100 is brought close to an NFC IC chip disposed in each seat of a restaurant while the matching app is active, the arithmetic unit 104 may acquire the restaurant ID and the seat ID from the IC chip through the short-range communication unit 107.

The arithmetic unit 104 acquires menu information indicating one or more foods provided by the restaurant corresponding to the restaurant ID from the second server 300 associated with the restaurant over the network NT, and stores the acquired menu information in the memory 102. For example, in the case where the restaurant ID includes an identifier for Restaurant A, menu information is acquired from the second server 300 of Restaurant A.

The arithmetic unit 104 transmits the identification information stored in the memory 102 to the first server 200, acquires the religion information of the user from the first server 200 on the basis of the identification information, and stores the acquired religion information in the memory 102.

The arithmetic unit 104 extracts one or more first foods corresponding to the religion information on the basis of the acquired menu information and the acquired religion information. The arithmetic unit 104 displays the one or more extracted first foods through a second operation screen which corresponds to the second server 300 and which is for receiving an order of food from the restaurant displayed on the display 105.

On the second operation screen, the one or more first foods are generated such that a second food that is incompatible with the religion information, that is, a second food containing an ingredient that should be avoided, is excluded or grayed-out. With this arrangement, the user is able to smoothly order a food that does not contain an ingredient that should be avoided.

Figure 18:
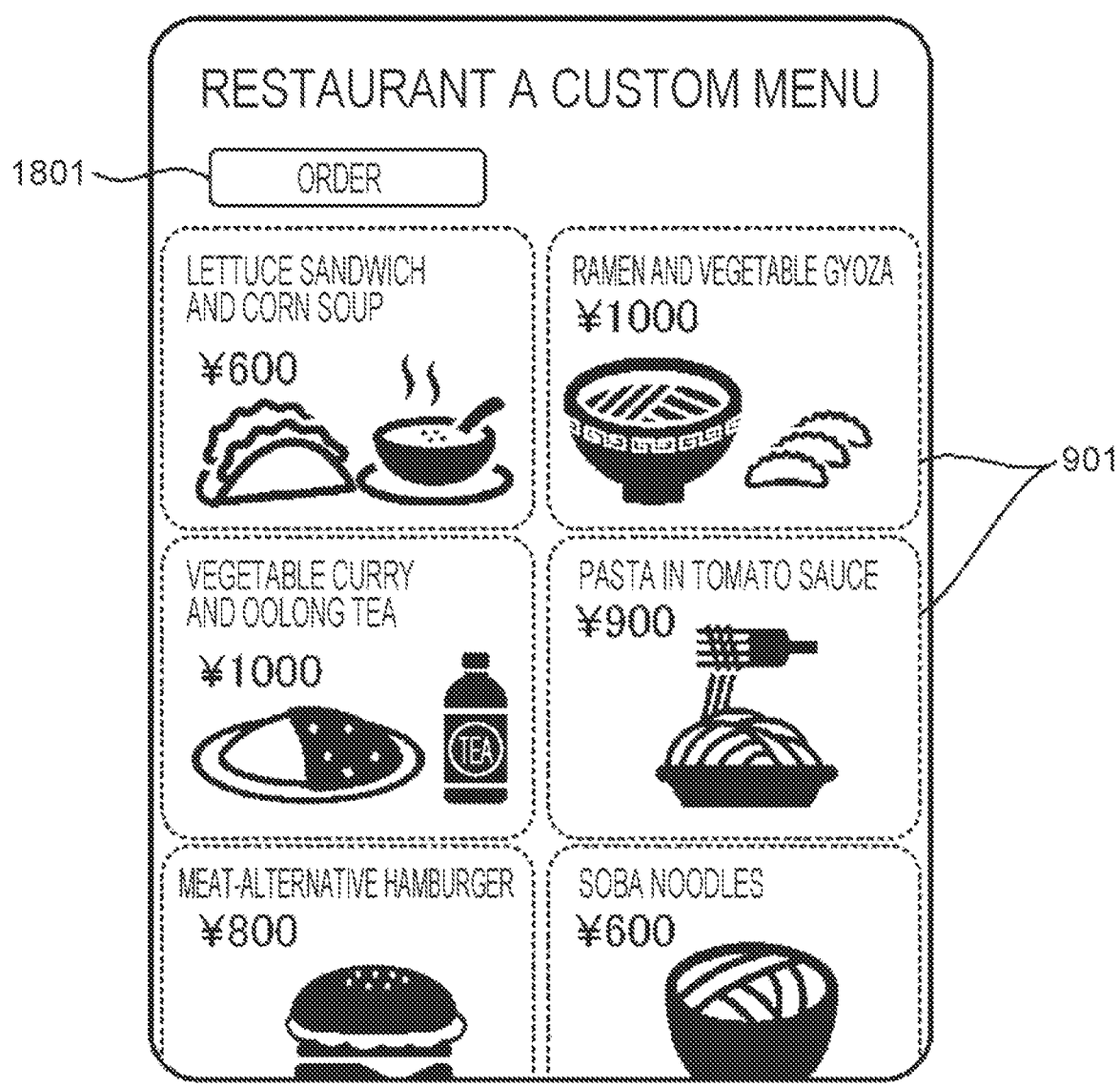
FIG. 18 is a diagram illustrating an example of an operation screen including a personalized menu.

The second operation screen is an operation screen by which the restaurant receives an order of food from the user as illustrated in FIG. 18 for example, and includes a personalized menu in which foods for individual users are arranged. The second operation screen is provided through the matching app on the basis of a design designated by the restaurant. The user orders a food by inputting an operation of selecting the desired food from the personalized menu displayed on the second operation screen.

The arithmetic unit 104 transmits food order information indicating the food selected from among the one or more first foods displayed on the second operation screen and the seat ID in association with each other to the second server 300 through the communication unit 101. The food order information and the seat ID transmitted to the second server 300 are displayed on a display installed in the restaurant location (that is, store) corresponding to the destination second server 300. An employee of the store prepares the food ordered by the user in accordance with the displayed content, and carries the prepared food to the user's seat. With this arrangement, the user is able to eat the ordered food.

The display 105 is a display panel such as a liquid crystal display (LCD) panel or an organic electroluminescence (OLED) panel for example, and displays various images. For example, the display 105 displays the first operation screen and the second operation screen described above.

The operation unit 106 is an input device such as a touch panel, for example. The operation unit 106 receives an instruction regarding the selection of a desired food by the user from the personalized menu.

The short-range communication unit 107 is a communication circuit provided with an NFC communication function, and is capable of reading information from an IC chip having a NFC communication function and also writing information to the IC chip.

The GPS sensor 108 receives radio waves transmitted from GPS satellites, and calculates position information indicating the current position of the information terminal 100 on the basis of the radio waves.

This concludes the description of the configuration of the information terminal 100.

Next, the configuration of the first server 200 will be described. The first server 200 includes a communication unit 201, an arithmetic unit 202, and a memory 203. The communication unit 201 is a communication circuit for connecting the first server 200 to the network NT. The communication unit 201 transmits the religion information to the information terminal 100 in response to a request from the information terminal 100. The arithmetic unit 202 is a processor such as a CPU. The arithmetic unit 202 processes personal information about the user stored in the memory 203.

The memory 203 is a plurality of non-volatile storage devices such as hard disk drives. The memory 203 stores personal information about one or more users. The personal information includes religion information about each user. The personal information is stored distributively in an encrypted form in the plurality of storage devices.

The personal information stored by the memory 203 may also include religion information, biometric information, purchase history information, preference information, and activity history information. The biometric information is information related to the user's body, such as heart rate. The biometric information includes information about the user's allergies or the like. The purchase history information is information indicating a purchase history of products (goods) or services purchased by each user. The preference information is information indicating the preferences of each user. The preference information includes order history information indicating an order history of foods ordered by each user. The activity history information is information indicating an activity history of each user. For example, the activity history information includes time series data in which user position information and time information are associated.

Next, the configuration of the second servers 300 will be described. One or a plurality of the second servers 300 exist in correspondence with each restaurant company. Each second server 300 includes a communication unit 301, an arithmetic unit 302, and a memory 303. The communication unit 301 is a communication circuit for connecting the second server 300 to the network NT. The communication unit 301 transmits the menu information to the information terminal 100 in response to a request from the information terminal 100. The arithmetic unit 302 is a processor such as a CPU. The arithmetic unit 302 processes menu information stored in the memory 303. The memory 303 is a non-volatile storage device such as a hard disk drive. The memory 303 stores the menu information.

Figure 5:
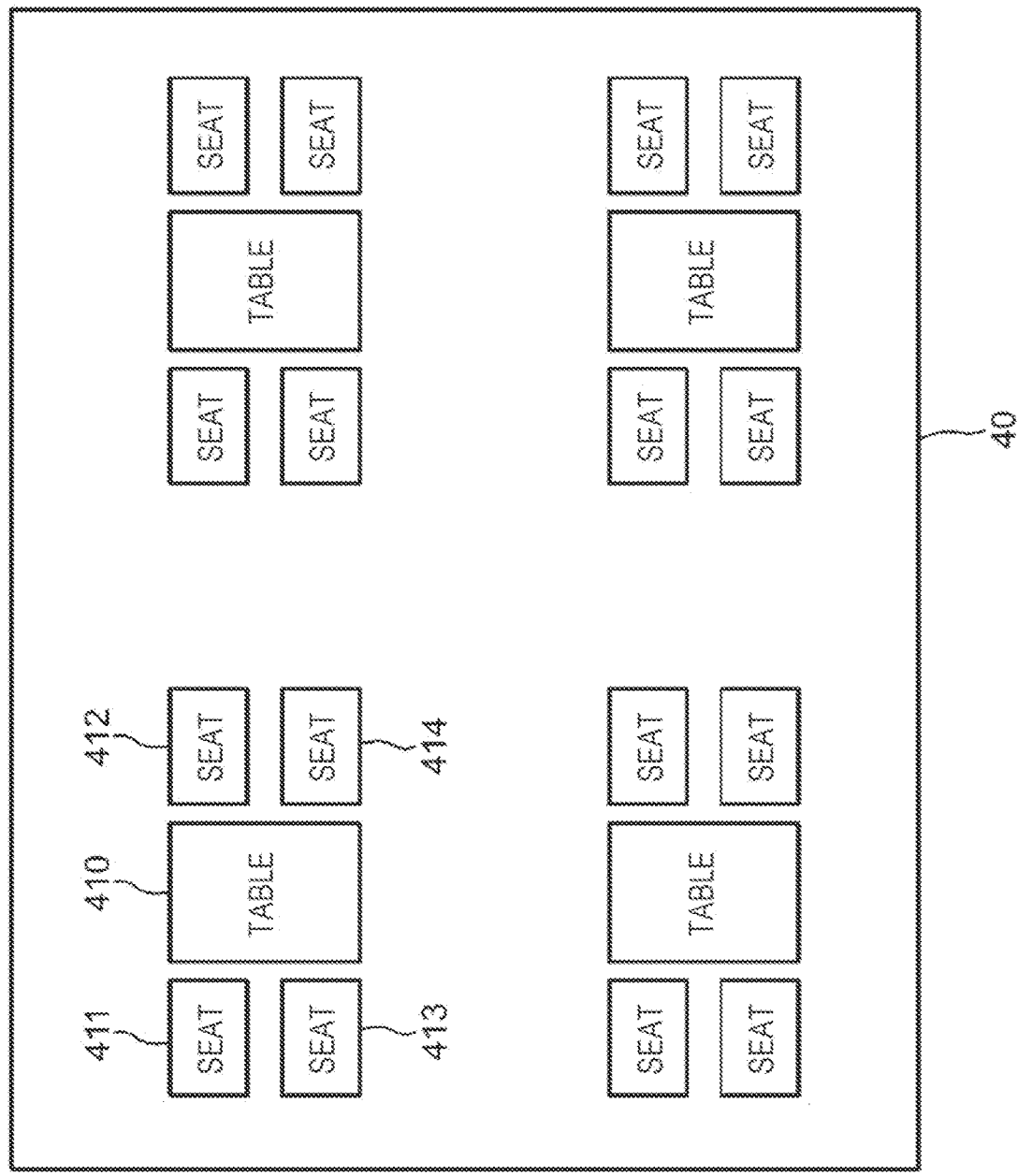
FIG. 5 is a diagram illustrating the layout of a certain restaurant location (that is, a store).

FIG. 5 is a diagram illustrating the layout of a certain restaurant location (that is, store). In the example of FIG. 5, the layout of a store 40 of Restaurant A is illustrated. Four tables 410 are installed in the store 40. At each table 410, four chairs 411, 412, 413, and 414 are installed.

In some cases, two or more users of different religions may sit down at a single table 410. In such cases, it is imperative to avoid mistakenly serving a food ordered by a certain user to another user of a different religion, and furthermore, the food must not contain an ingredient that should be avoided by the user. This is because if such a serving mistake occurs, there is a possibility of discomforting the user, and furthermore, if the user eats the mistakenly served food, there is a possibility that the user's health may be impaired as a result of eating an ingredient that he or she is unaccustomed to eating.

To avoid such mistakes, an appropriate mechanism for associating a user with a food ordered by the user is necessary. However, the solutions for avoiding such mistakes are limited at present. In particular, a solution applicable to the store of a typical restaurant as illustrated in FIG. 5 does not exist. Currently, in small-scale stores where a counter with individually numbered seats is installed, such association has been attempted, but because the association is made manually using an order slip or an order input terminal, serving mistakes are not fully addressed.

The present embodiment provides a mechanism for associating and managing a user and a food ordered by the user more reliably. Hereinafter, a specific example for achieving the mechanism will be described. In the present embodiment, a QR code is installed with respect to each seat in the store 40. FIGS. 6A, 6B, 6C, and 6D are diagrams illustrating examples of installing a QR code 601 with respect to a seat.

Figure 6A:
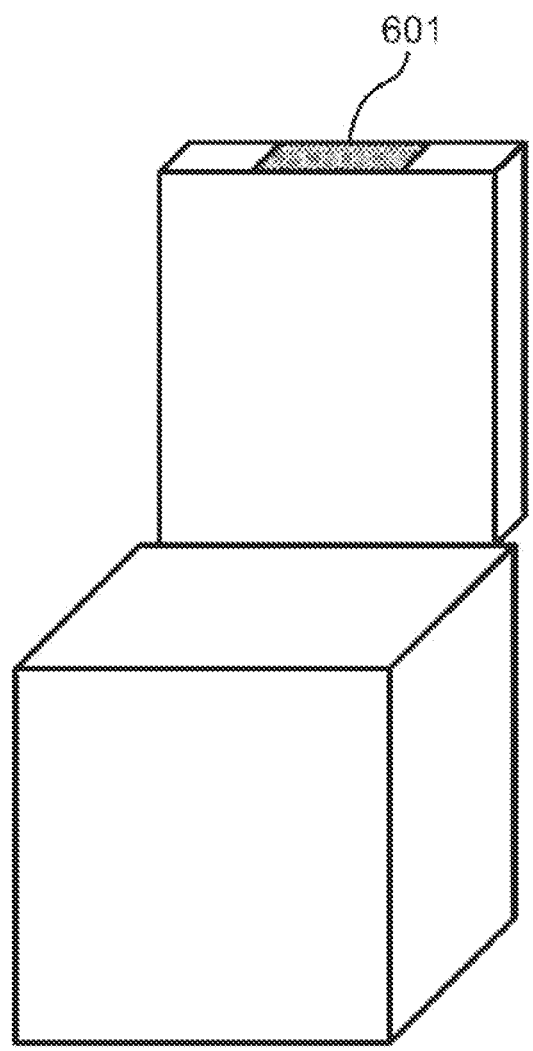
FIG. 6A is a diagram illustrating an example of the installation of a QR code (registered trademark; the same applies hereinafter) with respect to a seat.

In the example of FIG. 6A, the QR code 601 is placed on the upper surface of the backrest of each chair in the store. The QR code 601 contains the restaurant ID and the seat ID of each seat as described above. Here, a QR code is used, but this is merely an example, and any type of information may be adopted insofar as the information can be used to identify the restaurant ID and the seat ID, such as a barcode.

Figure 6B:
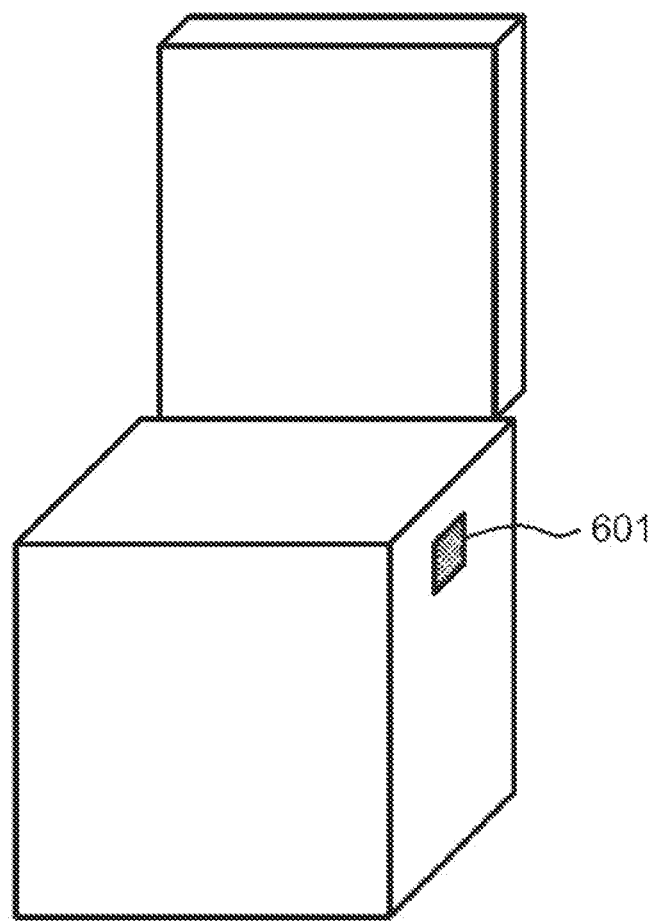
FIG. 6B is a diagram illustrating an example of the installation of a QR code with respect to a seat.

In the example of FIG. 6B, the QR code 601 is placed on a side surface of the seat portion of each chair. By placing the QR code 601 on the side surface of the seat portion, the user operation performed when reading the QR code 601 is easy to perform.

Figure 6C:
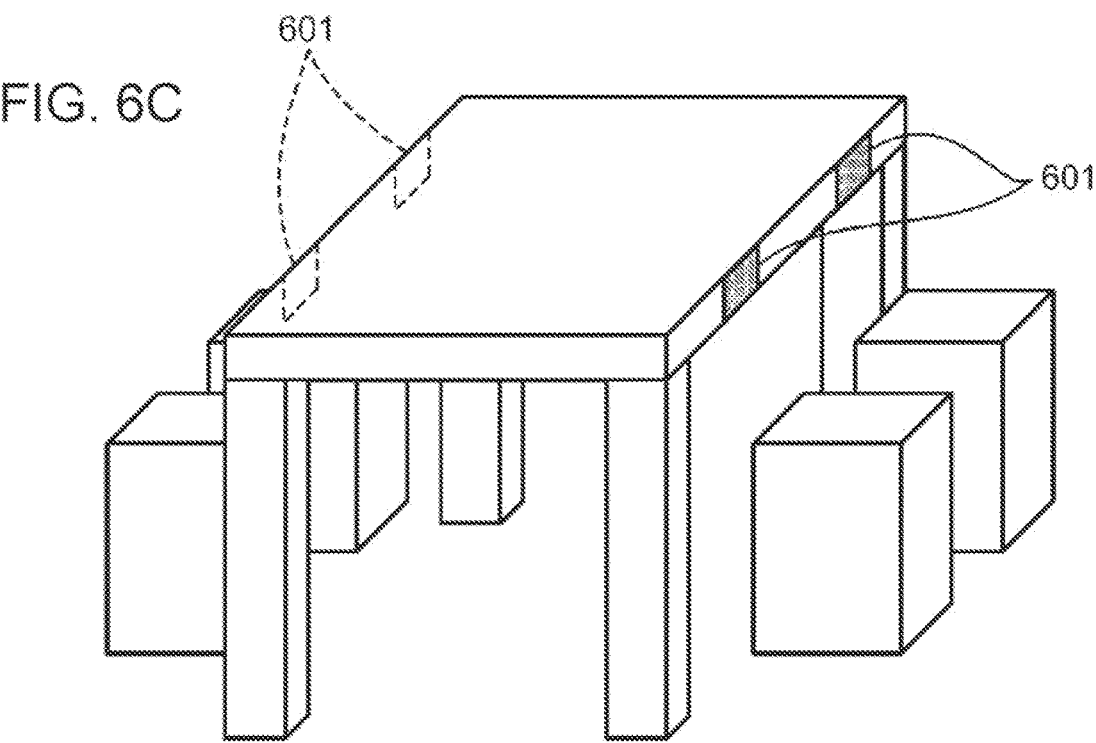
FIG. 6C is a diagram illustrating an example of the installation of QR codes with respect to seats.

In the example of FIG. 6C, the QR code 601 is placed on the sides of the table (for example, the surfaces facing the chairs) rather than on the chairs. In this example, the table seats four people, and therefore four QR codes 601 corresponding to each seat are placed on the sides of the table.

Figure 6D:
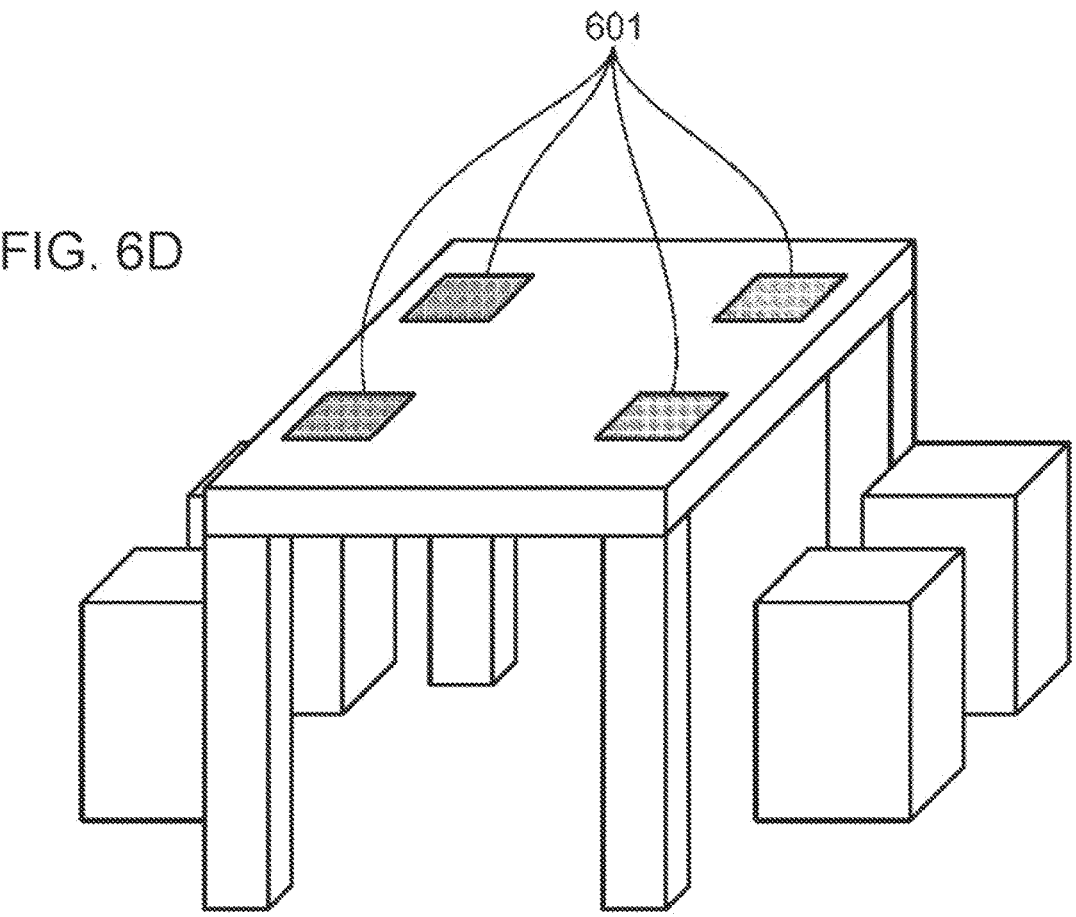
FIG. 6D is a diagram illustrating an example of the installation of QR codes with respect to seats.

In the example of FIG. 6D, the QR code 601 is placed on the surface of the tabletop. In this example, the table seats four people, and therefore four QR codes 601 corresponding to each seat are placed on the surface of the tabletop. By placing the QR code 601 on the surface of the tabletop, the user is able to notice the existence of the QR code 601 easily.

The QR code prepared for each seat is used by the information terminal 100 of the user ordering a food to acquire the menu information of the store. Hereinafter, a method of ordering a food using the QR code and the information terminal 100 will be described sequentially in detail. In the present embodiment, ordering a food includes the case of ordering from a standard menu and the case of ordering from a personalized menu.

Note that in FIG. 6, the QR code 601 is placed with respect to each seat, but in the case of adopting a configuration that acquires the restaurant ID and the seat ID by NFC, an IC chip including an NFC communication function is adopted instead of the QR code 601.

(Ordering from Standard Menu)

The standard menu is used in the case where a user who does not embrace any particular religion or a user who embraces a religion whose doctrine does not include any particular eating restrictions orders a food. The standard menu is a menu that includes typical foods provided to users at the store. Hereinafter, the process of ordering a food from the standard menu will be described using various screens displayed on the information terminal 100.

Figure 27:
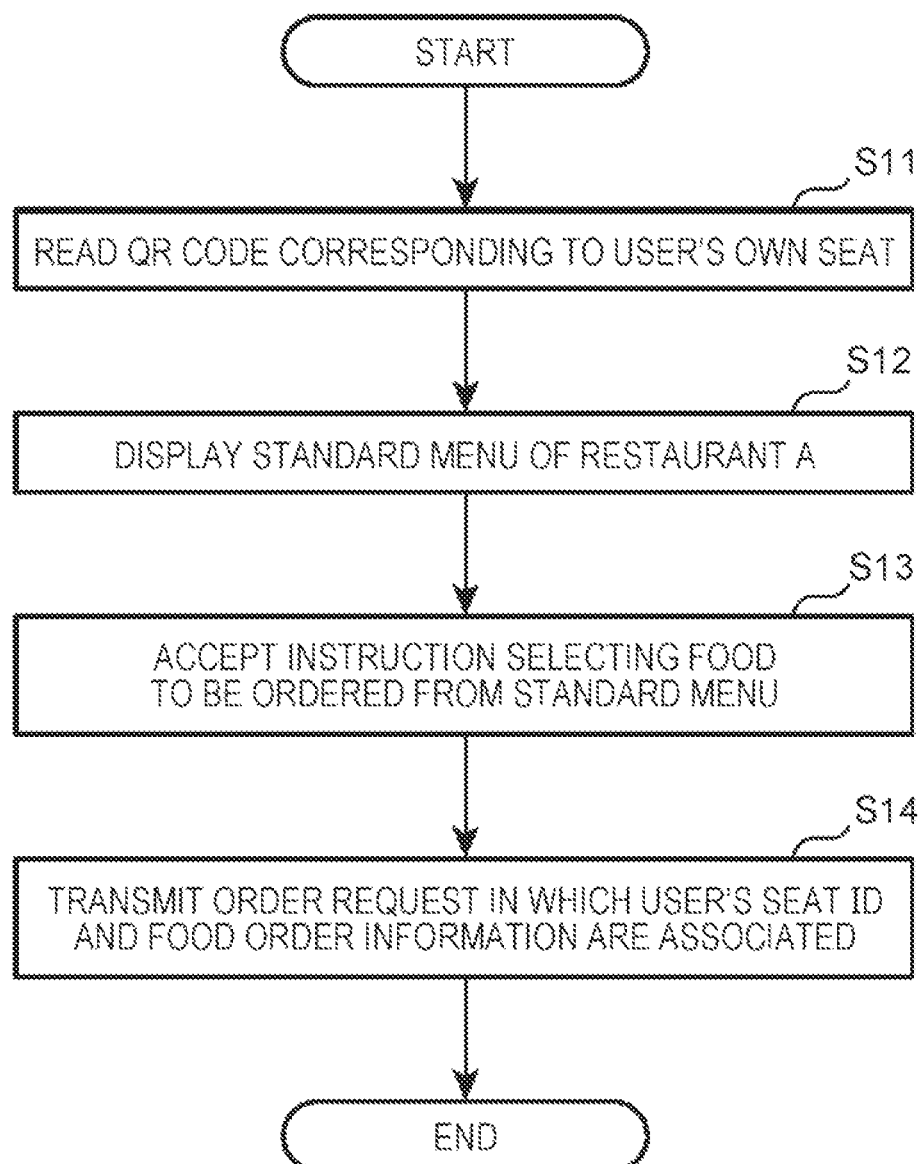
FIG. 27 is a flowchart illustrating an example of a process by the information terminal in a case where a food is ordered from the standard menu.

The process of ordering from the standard menu corresponds to the flowchart in FIG. 27, and accordingly the following description makes reference to the flowchart in FIG. 27 when appropriate. First, a QR code reader is launched, and the QR code reader reads the QR code corresponding to the seat where the user is sitting. This process corresponds to step S11 of FIG. 27.

Figure 7:
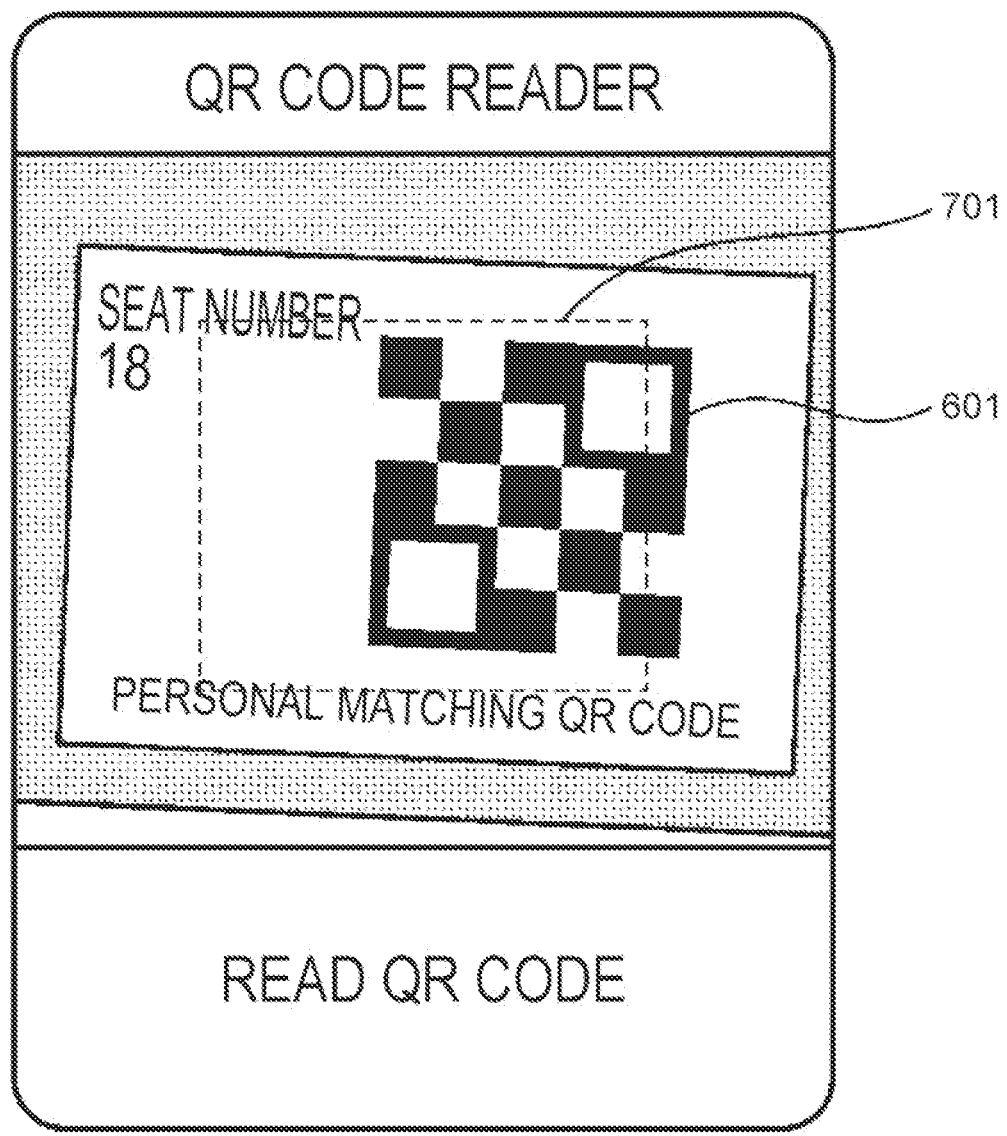
FIG. 7 is a diagram illustrating an example of an operation screen displayed on an information terminal in a case where a user causes the information terminal to read a QR code.

FIG. 7 is a diagram illustrating an example of an operation screen G1 displayed on the information terminal 100 in the case where the user causes the information terminal 100 to read the QR code. The operation screen G1 is displayed in a situation where a user who has entered the store of a restaurant and sat down causes the information terminal 100 to read the QR code corresponding to the seat (the user's seat) where the user sat down. The QR code corresponding to the user's seat is placed in one of the configurations illustrated in FIGS. 6A to 6D. The seated user takes out the information terminal 100 and causes the information terminal 100 to read the QR code corresponding to the user's seat to acquire the standard menu of the store of the restaurant. The reading of the QR code is achieved using a preinstalled general-purpose QR code reading app referred to as a "QR code reader". FIG. 7 illustrates the operation screen G1 while the user is in the middle of performing an operation of aligning the focus information terminal 100 with the QR code corresponding to the user's seat. The user adjusts the direction and position of the information terminal 100 such that the QR code 601 is contained inside guide lines 701 (the dashed-line square in the drawing) of the QR code reader. Near the QR code 601 placed for each seat, the information "Seat Number 18" used by the user or the staff of the store to specify the seat and an explanation of the purpose of the QR code 601 (in the drawing, "Personal Matching QR Code" are also placed. Consequently, an image expressing "Seat Number 18" and an image expressing "Personal Matching QR Code" are also displayed on the operation screen G1.

Next, the menu information of Restaurant A is acquired from the QR code read by the QR code reader, and a standard menu is generated on the basis of the menu information and displayed on the information terminal 100.

Figure 8:
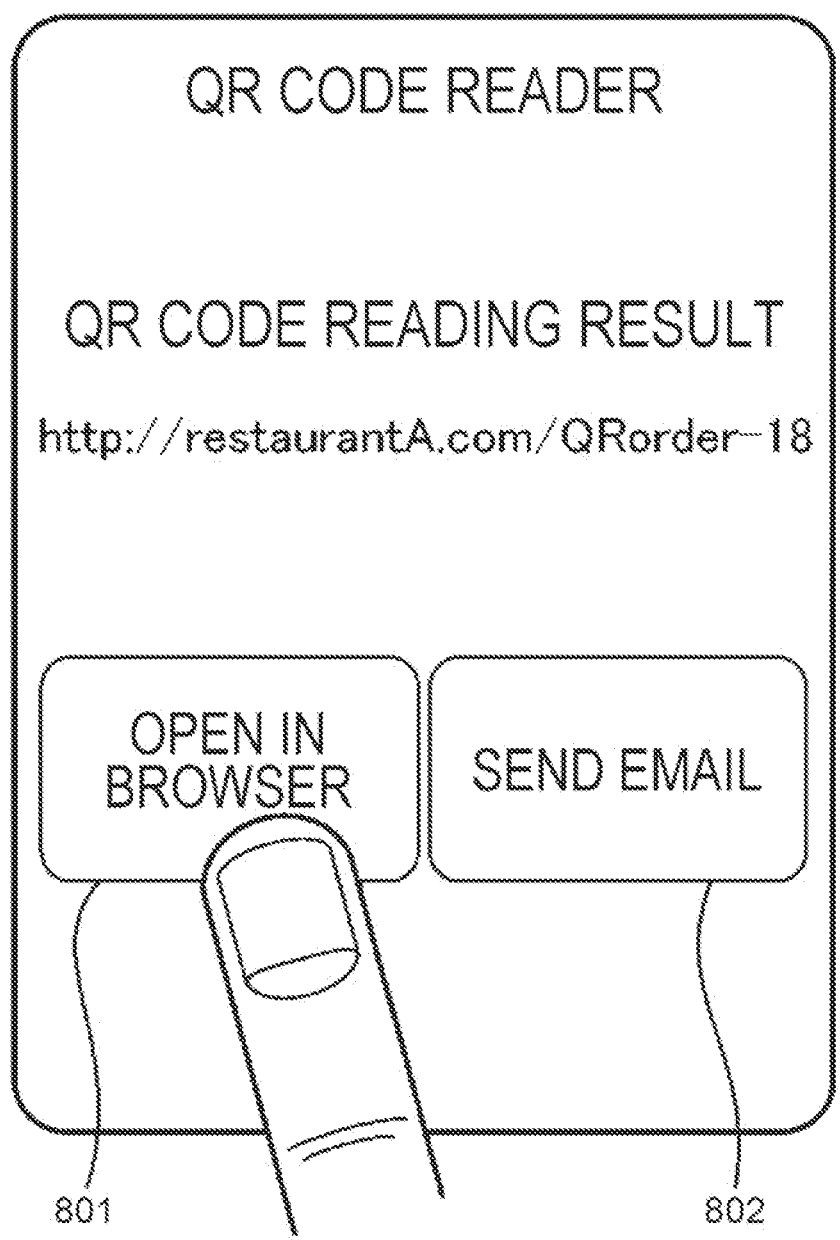
FIG. 8 is a diagram illustrating an example of an operation screen displayed on the information terminal immediately after a QR code reader reads a QR code.

This process corresponds to step S12 of FIG. 27. FIG. 8 is a diagram illustrating an example of an operation screen G2 displayed on the information terminal 100 immediately after the QR code reader reads the QR code. On the operation screen G2, a character string obtained as a result of the QR code reader successfully reading the QR code is displayed. In this example, the character string "http://restaurantA.com/QRorder-18" is obtained as the result of reading the QR code. The operation screen G2 includes a button 801 labeled "Open in Browser" and a button 802 labeled "Send Email". The button 801 is a button selected in the case where the user interprets the character string obtained as the result of reading the QR code to be a URL. When the button 801 is touched, an Internet browser is launched and a web page indicated by the URL is displayed on the information terminal 100.

The button 802 is a button selected in the case where the user interprets the character string obtained as the result of reading the QR code to be an email address. When the button 802 is touched, an email app is launched. Here, the button 801 is touched to view the standard menu.

When ordering a food from the standard menu, it is not necessary to install a specific app on the information terminal 100, and the QR code reader and the browser are sufficient. Consequently, ordering a food using the standard menu is easy for many users.

From destination information (for example, the portion of the domain name "restaurantA.com") included in the character string (for example, a URL) read by the QR code reader, the browser can specify that the destination is Restaurant A, or in other words specify the restaurant ID. Because the numeral at the end of the requested URL is 18, the second server 300 can specify that the request is coming from the browser of the information terminal 100 that read the QR code of the seat with the seat number "18". The character string illustrated in FIG. 8 does not include the store ID of the store 40, but the store 40 (Store-A) may also be explicitly included. In this case, the character string signified by the QR code is expressed as "http://restaurantA.com/Store-A/QRorder-18", for example. The browser of the information terminal 100 acquires destination information requested in this way.

Figure 9:
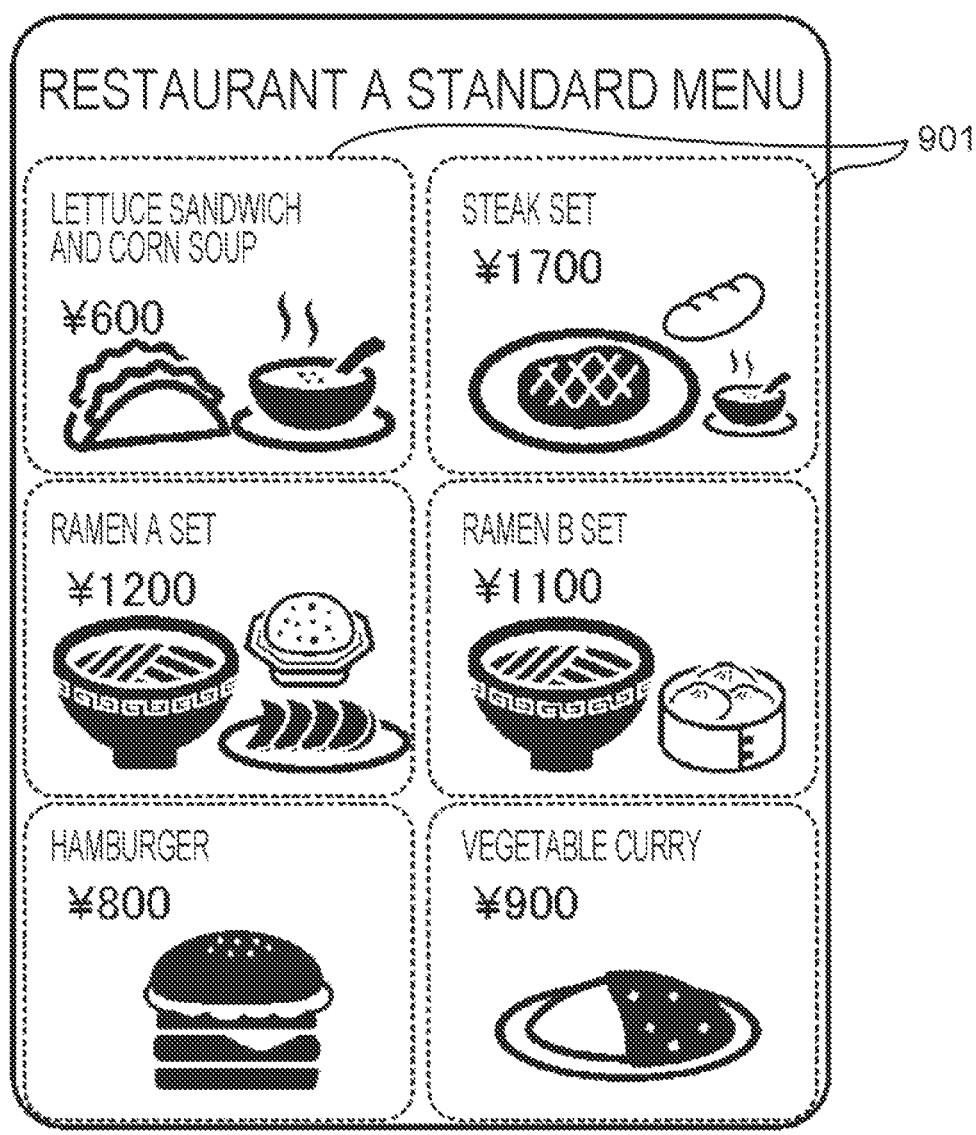
FIG. 9 is a diagram illustrating an example of an operation screen including a standard menu of Restaurant A.

FIG. 9 is a diagram illustrating an example of an operation screen G3 including a standard menu of Restaurant A. The operation screen G3 is displayed in the case where menu information is received by the information terminal 100. The standard menu includes the food included in the menu information as-is, and does not correspond to the user's religion information. The menu information may be the same information as the menu information used when generating a personalized information, or different information.

On the operation screen G3, a plurality of tile objects 901 are arranged in a matrix. The standard menu is formed by the plurality of tile objects 901. One tile object 901 corresponds to one food included on the standard menu. Each tile object 901 includes the name of the food, the price of the food, and an image of the food. On the operation screen G3, the standard menu scrolls in response to a scrolling operation performed by the user. With this arrangement, other foods that could not be displayed all at once on the operation screen G3 are displayed. In this way, by performing a scrolling operation, the user is able to view all of the foods included on the standard menu.

The operation screen G3 is displayed by having the browser connect to the URL (for example, http://restaurantA.com/QRorder-18) indicated by the character string obtained as the result of reading the QR code, and by having the browser receive the menu information from the second server 300 of Restaurant A.

For example, the browser of the information terminal 100 connects to the above URL and transmits an HTTP requests for an HTML file for drawing the standard menu of Restaurant A, receives an HTTP response from the second server 300 of Restaurant A, and draws the operation screen G3 including the standard menu according to the received HTTP response. However, the embodiment is merely an example, and the drawing of the operation screen G3 may also be achieved by another technical means.

Next, a food is selected by the user from the displayed standard menu. This process corresponds to step S13 of FIG. 27.

Figure 10:
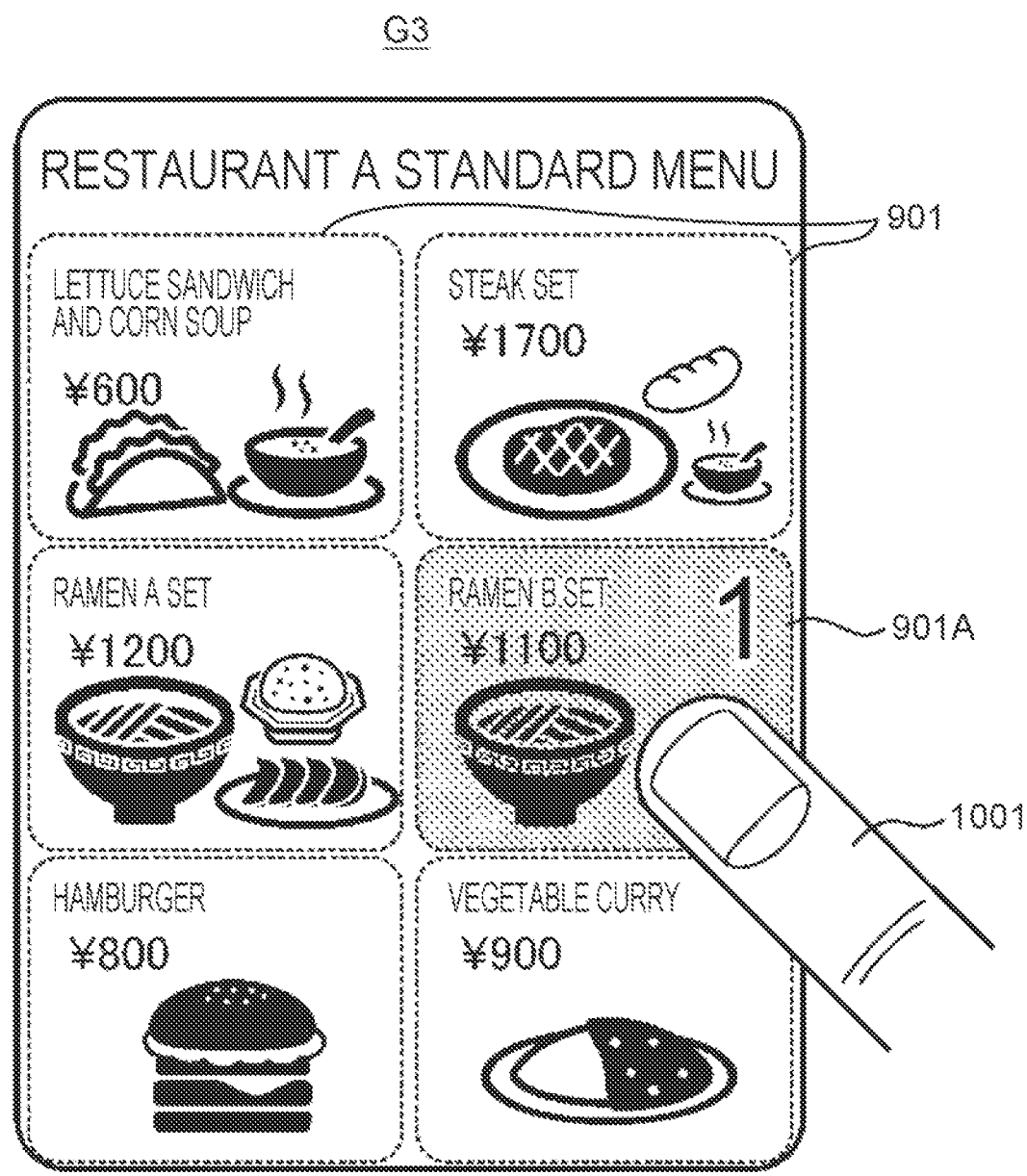
FIG. 10 is a diagram illustrating an example of a scenario in which a user operates the operation screen to order a food from the standard menu.

FIG. 10 is a diagram illustrating an example of a scenario in which a user operates the operation screen G3 to order a food from the standard menu. As the drawing indicates, the user can decide on a food to order by performing a touch operation using a pointing object 1001 such as a finger. For example, if the information terminal 100 detects that a tile object 901A corresponding to the food "Ramen B Set" has been touched once, the color of the tile object 901A changes from a default first color to a second color indicating that the tile object 901A has been selected. At this time, the information terminal 100 displays "1" indicating the quantity of the "Ramen B Set" to be ordered in the upper-right corner of the tile object 901A, for example. The above therefore demonstrates that the food "Ramen B Set" has been selected from the standard menu in this example. Because the user is able to order a food by touching the tile object 901 corresponding to each food, the user is able to order a food intuitively and easily with a familiar sense of operation.

Note that although the color of the tile object 901 is changed when the user selects a food to be ordered, the configuration is not limited thereto. For example, a pattern of the tile object 901 may be changed from a first pattern to a second pattern when the tile object 901 is selected by the user. Alternatively, the color and the pattern of the tile object 901 may be changed from a first color and pattern to a second color and pattern when the tile object 901 is selected by the user.

Figure 11:
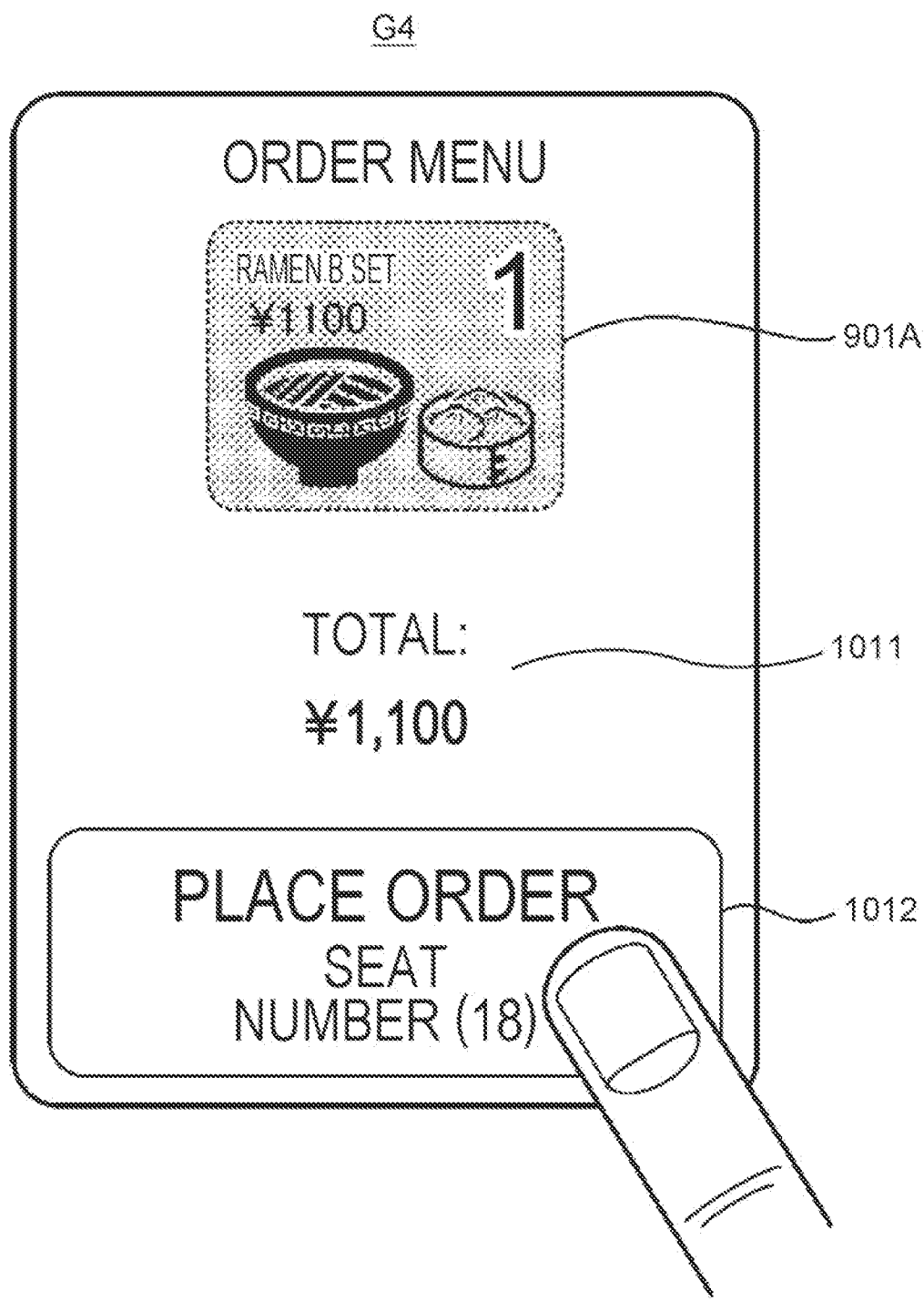
FIG. 11 is a diagram illustrating an example of an operation screen displayed when making a final confirmation of the food to order from the standard menu.

FIG. 11 is a diagram illustrating an example of an operation screen G4 displayed when making a final confirmation of the food to order from the standard menu. The operation screen G4 is displayed in the case where an Order button (not illustrated in FIG. 9) is touched by the user who has decided which food to order on the operation screen G3. The operation screen G4 includes a tile object 901A corresponding to the food selected on the operation screen G3, a total amount field 1011 indicating the total amount (for example 1,100 yen) of the ordered food, and an Order button 1012 for confirming the order. In this way, because a list of the food to be ordered, the quantity of each food, and the total amount of the food to be ordered are displayed on the operation screen G4, the user is able to check the order content efficiently on a single screen. After checking the order content and finding no problems, the user touches the Order button 1012 near the bottom of the operation screen G4. With this arrangement, the order of food is confirmed. Furthermore, because the seat number "18" is indicated on the Order button, the user is able to order the food with confirmation that the food will be served to the user's seat. When the Order button 1012 is touched, the information terminal 100 transmits an order request in which the seat ID (in the example of FIG. 11, the seat number "18") read from the QR code is associated with food order information indicating the selected food to the second server 300 of Restaurant A. With the above, the process of ordering from the standard menu is completed. This process corresponds to step S14 of FIG. 27.

The process of ordering from the standard menu for general customers is performed as described above. In this process of ordering, the user who orders a food causes the information terminal 100 to read a QR code and display the standard menu of Restaurant A in a browser, and orders a food through the standard menu. Consequently, the time and effort of pre-installing a specific app in the information terminal 100, such as an app distributed by Restaurant A, is saved. Therefore, the user is able to enjoy the service immediately using the information terminal 100, and the service is used by many users. In addition, the user is able to select and order a desired food easily from the standard menu with an intuitive operation. Furthermore, the zoom level of the operation screen G3 is adjusted by a pinch operation. Consequently, even a vision-impaired user is able to check the foods included on the standard menu easily. Furthermore, the user is also able to view more information at the same time by reducing the display scale of the operation screen G3. Furthermore, because the order request is an HTTP request in which the food order information is associated with the seat ID (for example, the seat number "18"), the second server 300 of Restaurant A can recognize the food ordered by the user at the seat number "18" through the HTTP request, and display the recognized seat number "18" and the ordered food on a display inside the store.

With this arrangement, a restaurant employee is able to server the ordered food to the seat number "18" without making a mistake. Furthermore, because the standard menu is not a paper medium, Restaurant A can save the time and effort involved in updating or managing the standard menu in the case of adopting a standard menu on a paper medium. As a result, it is possible to attain a reduction in the human resources for taking orders, a reduction in the risk of complaints about mistakes made when receiving orders, lowered costs, and increased business efficiency.

(Ordering from Personalized Menu)

Next, ordering a food from a personalized menu will be described. Whereas the standard menu is a menu provided by a restaurant for general customers, the personalized menu is a menu including foods that are compatible with the religion information of the user. The process of ordering a food from the personalized menu is illustrated by the flowchart in FIG. 26 described later. Hereinafter, the process of ordering a food from the personalized menu will be described while referring to the flowchart in FIG. 26 when appropriate.

Figure 12:
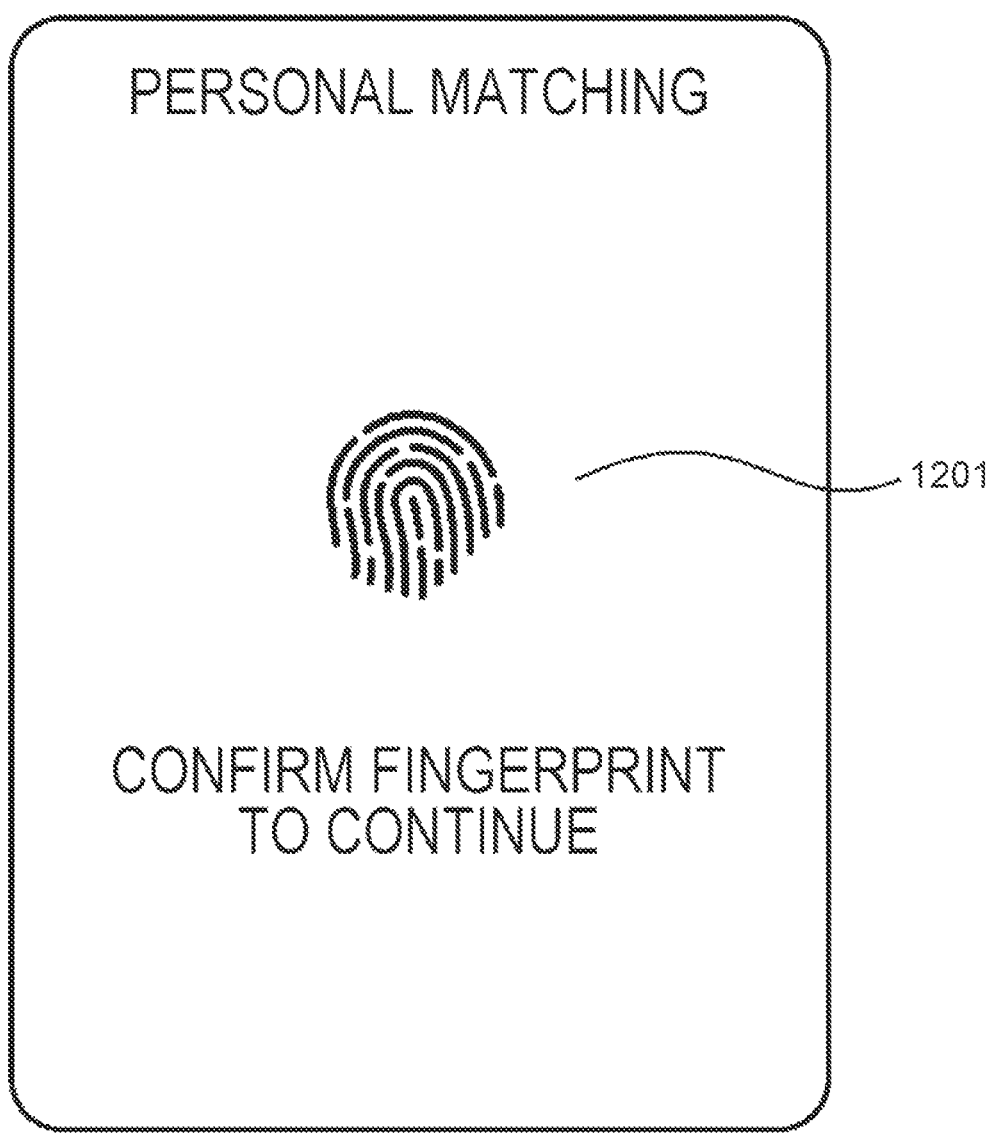
FIG. 12 is a diagram illustrating an example of an authentication screen displayed on the information terminal immediately after the user ordering a food launches a matching app.

The ordering of a food through the personalized menu is initiated when triggered by the launching of the matching app. FIG. 12 is a diagram illustrating an example of an authentication screen G101 displayed on the information terminal 100 immediately after the user ordering a food launches the matching app. The authentication screen G101 is a screen for performing user authentication through fingerprint authentication. On the authentication screen G101, a fingerprint image 1201 illustrating a representation of a fingerprint in the center is displayed, and the message "Confirm fingerprint to continue" is displayed below the fingerprint image 1201. With the above, the authentication screen G101 prompts the user to perform fingerprint authentication. "Personal Matching" is displayed near the top of the authentication screen G101. With this arrangement, the user is made to recognize that the authentication screen G101 is a screen of the matching app. The same applies to FIGS. 13 to 17 described later.

Figure 13:
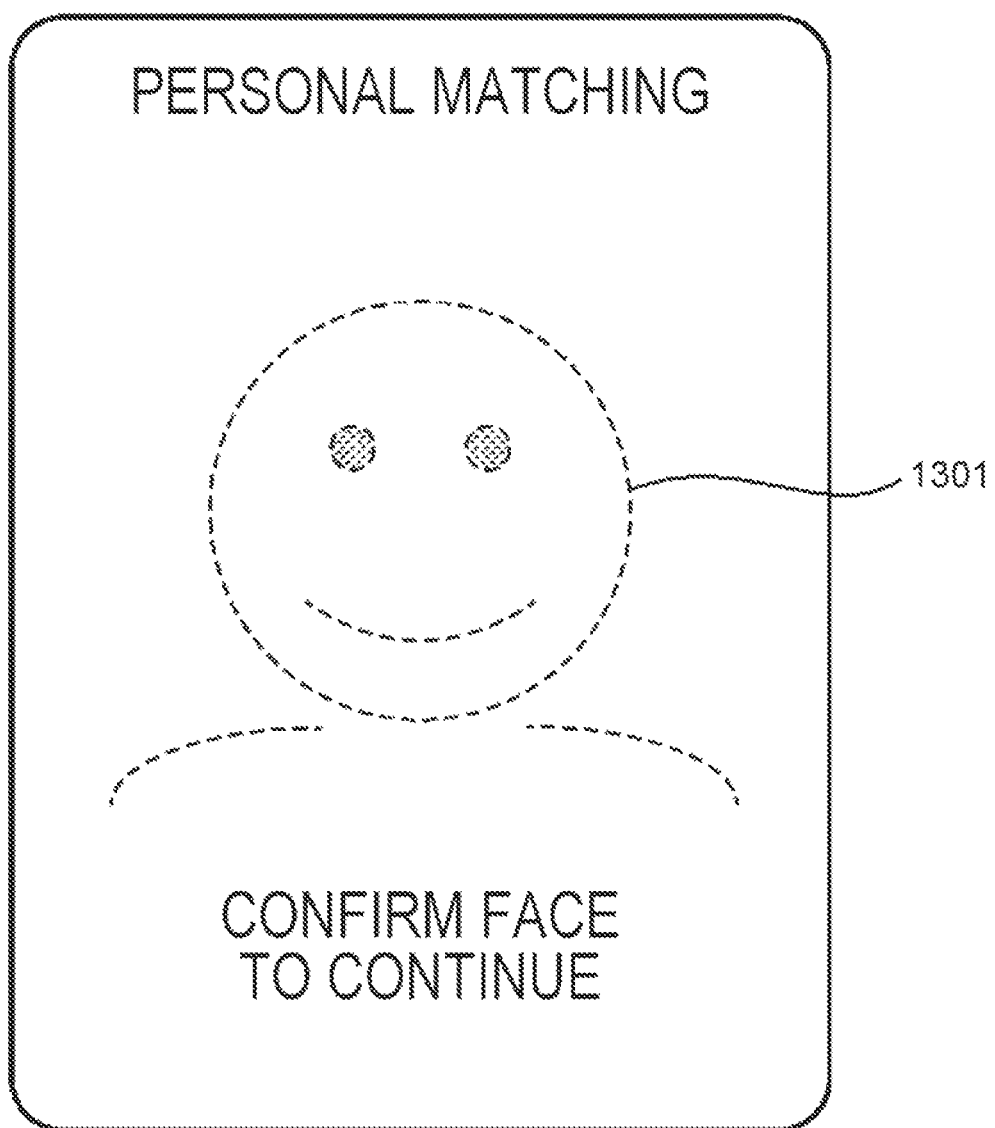
FIG. 13 is a diagram illustrating another example of the authentication screen.

FIG. 13 is a diagram illustrating an example of another authentication screen G102. The authentication screen G102 is an example of a screen for performing user authentication through face authentication. On the authentication screen G102, a dashed line 1301 illustrating a representational outline of a face is displayed in the center, such that an image of the user's face from the front will be captured at a suitable size by the information terminal 100. The user adjusts the direction and position of the information terminal 100 such that the user's own face from the front is displayed so as to be contained within the dashed line 1301.

If another method of user authentication capable of sufficient authentication accuracy with a lower user burden compared to the user authentication methods described above is available, the other method may also be adopted. As the method of user authentication, two-factor authentication which is generally considered to be highly secure may be adopted, or a method of inputting a user ID and a password may also be adopted.

Figure 14:
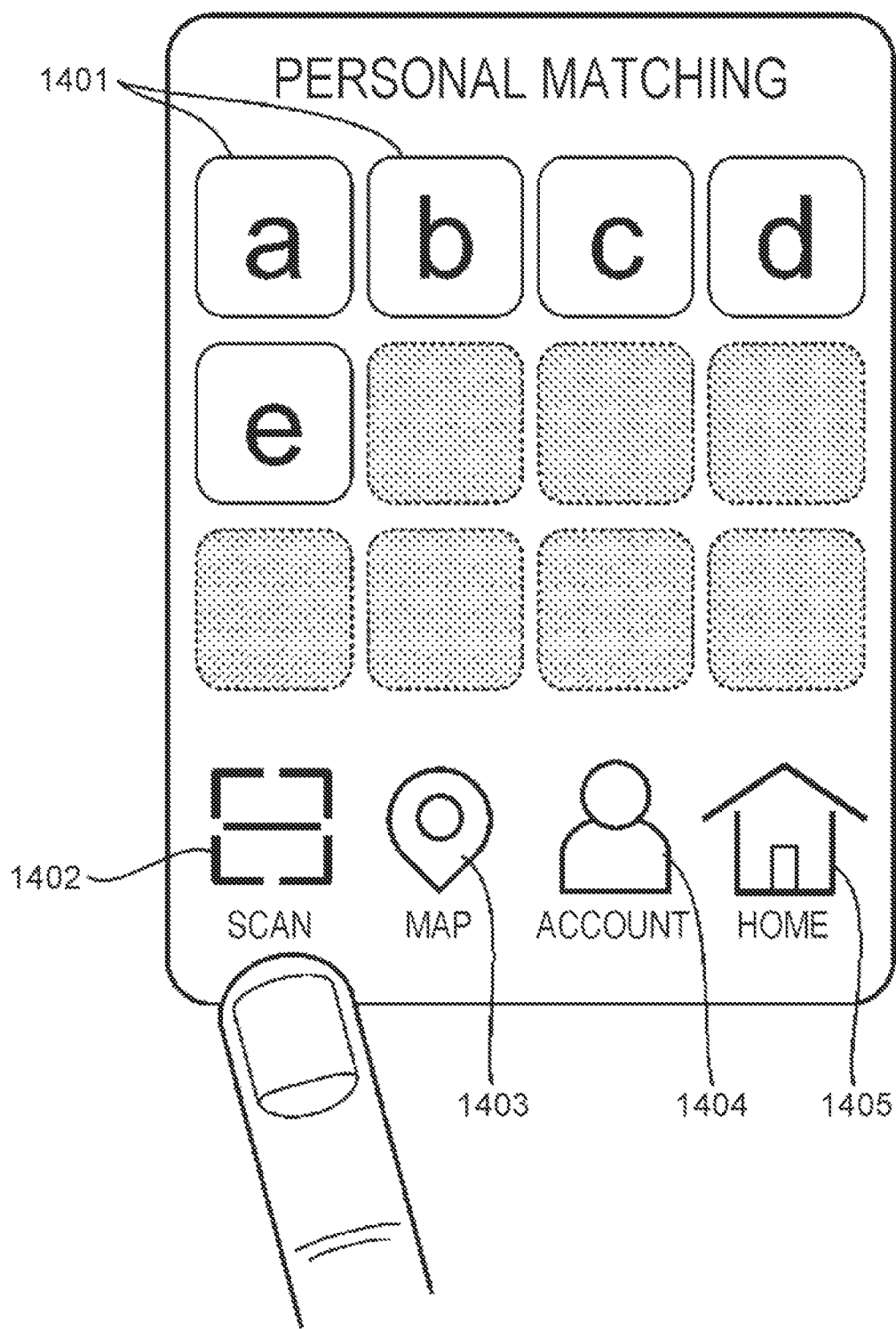
FIG. 14 is a diagram illustrating an example of a home screen displayed immediately after user authentication by the matching app ends.

FIG. 14 is a diagram illustrating an example of a home screen G103 displayed immediately after user authentication by the matching app ends. On the home screen G103, the app title "Personal Matching" is displayed in an upper row, and a plurality of tile objects 1401 are displayed in a matrix in a middle row. Each of the tile objects 1401 is associated with a linked function built into the matching app or a separate app. A separate app is an app launched from inside the matching app, for example. In this case, five tile objects 1401 labeled "a", "b", "c", "d", and "e" are displayed. The tile objects 1401 are associated with dedicated functions for matching with internal company products or internal company services (for example, an app within the matching app) linked to the matching app. With this arrangement, the user is able to use five types of linked functions indicated by "a", "b", "c", "d", and "e". The grayed-out tile objects 1401 are empty tile objects for which a linked function has not been installed. On a lower row of the home screen, a Scan button 1402, a Map button 1403, an Account button 1404, and a Home button 1405 are displayed in order from the left. The four buttons are static buttons. The Scan button 1402 is a button used in the case of reading a QR code or the like linked to a service provided by a business such as the restaurant described above. The Map button 1403 is a button for using a map screen to display stores supporting the matching app in the current vicinity of the information terminal 100. The Account button 1404 is a button for registering and editing the account information about the user. Registering and editing account information includes actions such as setting a personal authentication and setting a linked function with the first server 200, for example. The Home button 1405 is a button for returning the screen display to the home screen G103 illustrated in the diagram.

On the home screen G103, the tile objects 1401 for linking to a linked function, a different app, or a service from another business are arranged together in the middle row. The display or non-display as well as the arrangement of these tile objects 1401 are settable according to user preference. Consequently, the user is able to use a single matching app to acquire products and/or services suited to the user on the basis of the personal information from among the products or services provided by a large number of businesses (such as home appliance retailers, DVD/Blu-ray (registered trademark) rental shops, bookstores, coffee shops, and taxis, for example).

FIG. 15 is a diagram illustrating an example of an operation screen G104 displayed on the information terminal 100 in the case where the user, having launched the matching app, causes the information terminal 100 to read the QR code corresponding to the user's seat. The operation screen G104 (an example of the first operation screen) is mostly similar to the operation screen G1 in FIG. 7. The operation screen G104 differs from the operation screen G1 in that the app title display on the upper row is "Personal Matching" on the operation screen G104.

From destination information (for example, the domain name "restaurantA.com") included in the character string (for example, a URL) read by the QR code reader, the matching app can specify that the destination is Restaurant A. Because the numeral at the end of the URL requested by the matching app is "18", the second server 300 receiving the request can recognize that the request was transmitted from the information terminal 100 that read the QR code of the seat with the seat number "18". The present embodiment illustrates an example where the user sitting in the seat with the seat number "18" of the store 40 of Restaurant A orders a food from the store 40. In the request, the matching app may also specify the store 40 (Store-A) explicitly. In this case, the character string signified by the QR code is set to "http://restaurantA.com/Store-A/QRorder-18", for example. In this way, the matching app can acquire information (for example, the restaurant ID) specifying the destination.

The process of launching the matching app, performing user authentication, and reading the QR code described above corresponds to step S1 of FIG. 28.

In the case of adopting a configuration in which the restaurant ID and the seat ID are acquired by NFC instead of a QR code, the following first operation screen is used. FIG. 16 is a diagram illustrating an example of an operation screen G1011 displayed on the information terminal 100 in the case of acquiring a restaurant ID and a seat ID through NFC. Like the operation screen G104, the operation screen G1011 is also displayed in the case where the Scan button 1402 is touched on the home screen G103.

On the operation screen G1011, "Personal Matching" is displayed near the top to indicate that the screen is a screen of the matching app. In the center of the screen, an NFC mark 1601 symbolically representing NFC and a message (for example, "Hold device up to NFC mark") prompting the user to bring the information terminal 100 close to an object with the NFC mark 1601 attached are displayed.

In the case where the restaurant ID and the seat ID are acquired by NFC, each seat in the restaurant is provided with an IC chip including a memory that stores the restaurant ID and the seat ID and an NFC communication function. The NFC mark 1601 is displayed on the IC chip. With this arrangement, the user seeing the NFC mark 1601 on the operation screen G1011 can easily understand that he or she bring the information terminal 100 close to the IC chip disposed on the user's seat. As described above with regard to the QR code, it is sufficient if the memory of the IC chip stores a restaurant URL from which the restaurant ID and the seat ID are specifiable.

Next, the process by which the matching app accesses the second server 300 of Restaurant A and acquires the menu information will be described. This process corresponds to step S2 of FIG. 28.

Figure 17:
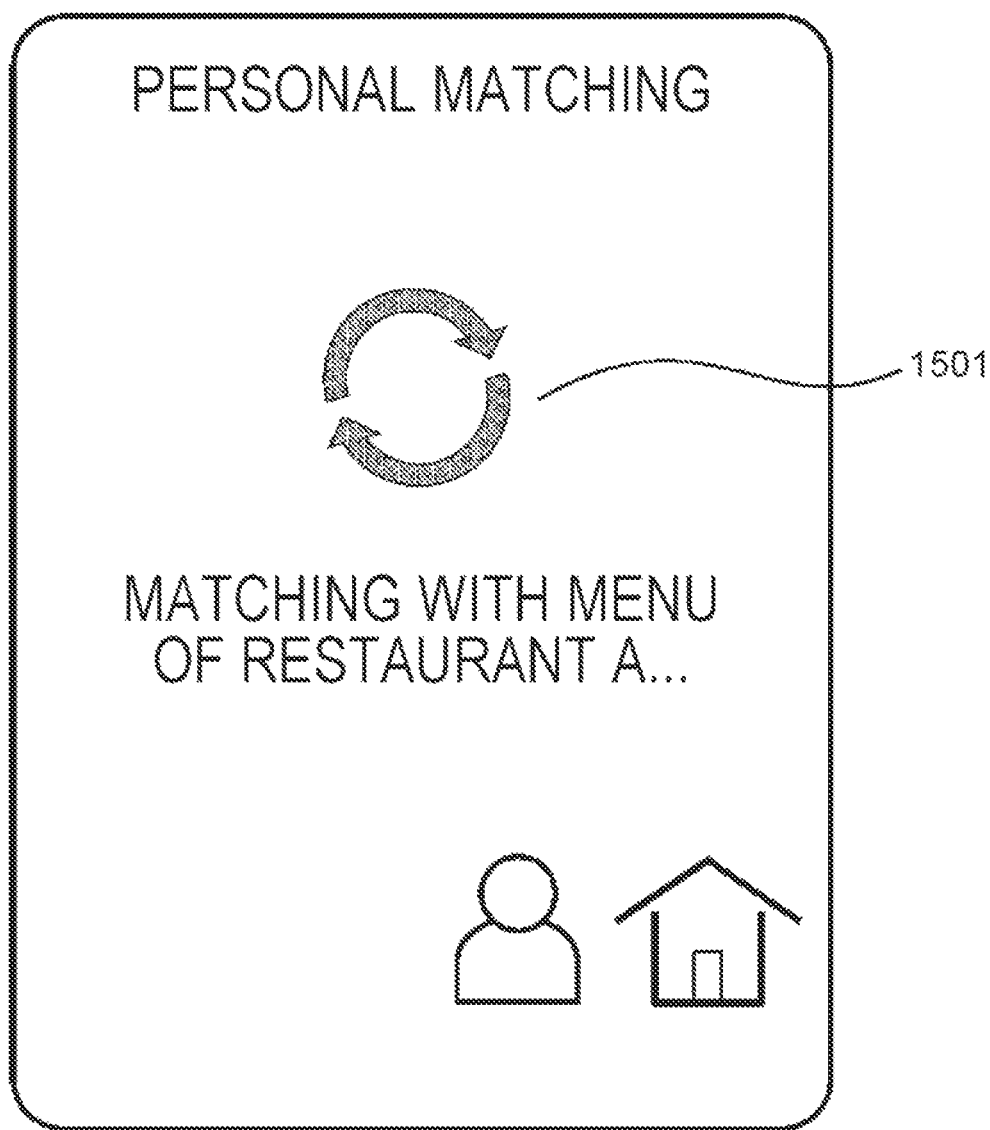
FIG. 17 is a diagram illustrating an example of a display screen displayed on the information terminal when the matching app is generating a personalized menu.

FIG. 17 is a diagram illustrating an example of a display screen G105 displayed on the information terminal 100 when the matching app is generating a personalized menu. On the display screen G105, a rotating circular arrow object 1501 is displayed. Additionally, "Matching with menu of Restaurant A . . . " is displayed below the arrow object 1501. With this arrangement, the user can recognize that the matching app is busy.

While the display screen G105 is being displayed, the matching app of the information terminal 100 cooperates with the second server 300 of Restaurant A and the first server 200 to generate a personalized menu. Specifically, the matching app accesses the second server 300 of Restaurant A on the basis of the URL read through the QR code 601 or NFC, and acquires the menu information. Having acquired the menu information, the matching app detects a data attribute of the menu information. Because the menu information is food-related information, the data attribute detected at this point is a food attribute.

The menu information is an HTML file, for example. In the menu information, the data attribute are described as being the food attribute in a predetermined format, for example. It is sufficient for the matching app to detect that the data attribute of the menu information is the food attribute on the basis of the format. Alternatively, the matching app may also detect that the data attribute of the menu information is the food attribute from the domain name of the URL indicated by the QR code, for example. Here, because the domain name "restaurantA.com" indicates Restaurant A, the data attribute of the menu information is determined to be the food attribute. Alternatively, the matching app may analyze the acquired menu information, and in the case of obtaining an analysis result indicating food-related data, the matching app may determine that the data attribute of the menu information is the food attribute. Alternatively, the matching app may acquire supplemental information indicating the data attribute of the menu information from the second server 300, and thereby detect that the data attribute of the menu information is the food attribute. Another method may also be adopted as the implementation for detecting the data attribute of the menu information, insofar as the method can be used to identify the data attribute.

Next, the process by which the matching app acquires religion information from the second server 300 will be described. This process corresponds to step S3 of FIG. 28.

Having determined that the data attribute of the menu information is the food attribute, the matching app requests the first server 200 to acquire the most recent religion information treated as a dietary restriction of the user classified under the food attribute. The request includes the user ID. The first server 200 receives the request and extracts the most recent religion information from the distributively encrypted personal information on the basis of the user ID. The extracted religion information is transmitted from the first server 200 to the information terminal 100. With this arrangement, the matching app acquires the religion information. Details about the religion information will be described later using FIG. 23.

Having acquired the religion information, the information terminal 100 executes a process of cross-referencing the menu information of Restaurant A with the religion information and generating a personalized menu. This process corresponds to step S4 of FIG. 28. At this time, the display screen G105 illustrated in FIG. 17 is still being displayed on the information terminal 100, but the matching app is executing the process of cross-referencing the menu information with the religion information and generating a personalized menu corresponding to the religion information.

Here, the method of generating a personalized menu to be included on the second operation screen has the following variations.

In the first variation, the arithmetic unit 104 generates, on the basis of the menu information and the religion information, a personalized menu in which foods (second foods) not compatible with the religion information, or in other words foods containing an ingredient that should be avoided from among the foods included in the menu information are excluded or grayed out. As an example, assume that beef is an ingredient that the user should avoid, and beef curry is included in the menu information. In this case, the tile object 901 indicating beef curry is excluded from the personalized menu or grayed out. Graying out refers to a display method in which the tile object 901 for beef curry is displayed semi-transparently with a gray color, for example. Note that because the religion information includes information related to ingredients that should be avoided as described later using FIG. 23, the arithmetic unit 104 can specify which ingredients should be avoided from the religion information.

In the second variation, the arithmetic unit 104 generates a personalized menu including a food with an added ingredient containing a nutrient that tends to be deficient in correspondence with the religion indicated by the religion information. As illustrated in FIG. 22, religions such as Islam, Judaism, Hinduism, Christianity, and Buddhism exist, and ingredients that should be avoided are stipulated by the doctrine of each religion. Consequently, nutrients that tend to be deficient for the followers of each religion can be roughly estimated. Accordingly, the arithmetic unit 104 may cause the memory 102 to store nutrients that tend to be deficient in correspondence with a religion in advance, and include foods containing the nutrients on the personalized menu. Here, "a food" refers to a certain single food. For example, people who embrace Hinduism are forbidden from consuming animal-based ingredients, and consequently tend to be deficient in protein, vitamins, calcium, iron, and zinc. For this reason, foods containing these ingredients are added to the personalized menu for users who embrace Hinduism.

In the third variation, the arithmetic unit 104 generates a personalized menu including a display indicating a combination of foods for supplementing a nutrient that tends to be deficient in correspondence with the religion indicated by the religion information. For example, followers of Hinduism tend to be deficient in iron. Boiled Japanese mustard spinach and natto are rich in iron. Consequently, in one example of this variation, a food set including a side dish of boiled Japanese mustard spinach or natto may be included on the personalized menu. As another example, as described later using FIG. 38, if the user selects a certain food from the personalized menu, a screen encouraging the user to order a food containing a deficient nutrient in addition to the certain food may be displayed on the display 105. In this case, the arithmetic unit 104 may determine a food containing a deficient nutrient predetermined for each food as the food to recommend to the user.

Another example of a combination of foods for supplementing a nutrient that tends to be deficient is a food set in which a food rich in Vitamin C, which works to increase iron absorption, is paired with a food containing iron.

Furthermore, the method of preparing the food may also be changed to supplement an nutrient that tends to be deficient. For example, the arithmetic unit 104 may also instruct the second server 300 of the corresponding restaurant to change the method of preparing the food to reduce the heating temperature and the heating time of the food and thereby increase the level of vitamin absorption.

In the fourth variation, the arithmetic unit 104 generates a personalized menu including a food with an added ingredient containing a nutrient in which the user has been deficient in past meals consumed by the user over a predetermined period. The predetermined period refers to a period going back a week or a month from the present, for example. Nutrients that tend to be deficient for the followers of each religion can be roughly estimated according to each religion, as described above in the second variation. The estimation is also similarly applicable to estimating nutrients that tend to be deficient in the predetermined period. Consequently, the arithmetic unit 104 may cause the memory 102 to store nutrients that tend to be deficient over a predetermined period according to each religion in advance, and include foods containing the nutrients on the personalized menu.

Alternatively, the arithmetic unit 104 may acquire food order history information for the predetermined period from the first server 200, and specify a nutrient that the user is deficient in from the order history information. For example, the order history information includes information related to foods that the user ordered in the past. The information related to foods includes a food name in addition to the ingredients and quantities thereof used in each food, for example. If the ingredients and ingredient quantities are known, each nutrient included in the ingredients and the quantity of each nutrient can be specified. Accordingly, the arithmetic unit 104 specifies nutrients and the quantity of each nutrient consumed by the user for each food included in the order history information, and calculates the cumulative value of the quantity of each specified nutrient over the predetermined period. Next, the arithmetic unit 104 determines whether or not the cumulative value falls below a predetermined threshold for each nutrient, and specifies a nutrient with a quantity determined to fall below the threshold as a deficient nutrient.

In the fifth variation, the arithmetic unit 104 generates a personalized menu including a display indicating a combination of foods for supplementing a nutrient in which the user has been deficient in past meals consumed by the user over a predetermined period. In this variation, the technique described in the fourth variation is used to specify a nutrient in which the user has been deficient over a predetermined period. Additionally, the technique indicated in the third variation is used to display a combination of foods for supplementing the deficient nutrient.

These five variations may also be combined appropriately.

Having generating the personalized menu, the matching app uses the browser to display the personalized menu on the information terminal 100 in the same way as when ordering from the standard menu. The foods listed on the personalized menu all account for the most recent religion information. Consequently, the user is able to order a food smoothly.

FIG. 18 is a diagram illustrating an example of an operation screen including a personalized menu. On an operation screen G106 (an example of a second operation screen), a plurality of tile objects 901 are arranged in a matrix, similarly to the operation screen G3. On the operation screen G106, the personalized menu is configured to scroll in response to a scrolling operation performed by the user. The personalized menu is formed by the plurality of tile objects 901. In the personalized menu on the operation screen G106, the tile objects 901 indicating meat-containing foods such as "Steak Set", "Ramen A Set", "Ramen B Set", and "Hamburger" that were included on the standard menu in FIG. 8 have been changed to tile objects 901 indicating foods that the user is able to eat, such as "Ramen and Vegetable Gyoza", "Vegetable Curry and Oolong Tea", "Pasta in Tomato Sauce", and "Meat-alternative Hamburger". Note that the example in FIG. 18 corresponds to a configuration combining the first variation (excluding foods containing an ingredient that should be avoided) and the second variation (adding an ingredient containing a nutrient that tends to be deficient) described above.

"Restaurant A Custom Menu" is displayed near the top of the operation screen G106, thereby clearly indicating that the personalized menu presented on the operation screen G106 is a menu customized to the user. This arrangement appeals to the user by indicating that the personalized menu included on the operation screen G106 is a menu of foods that user can eat with assurance.

On the operation screen G106, an Order button 1801 is displayed above the tile objects 901. The Order button 1801 switches the screen display to the operation screen G107 illustrated in FIG. 20 after a tile object 901 is selected.

Figure 19:
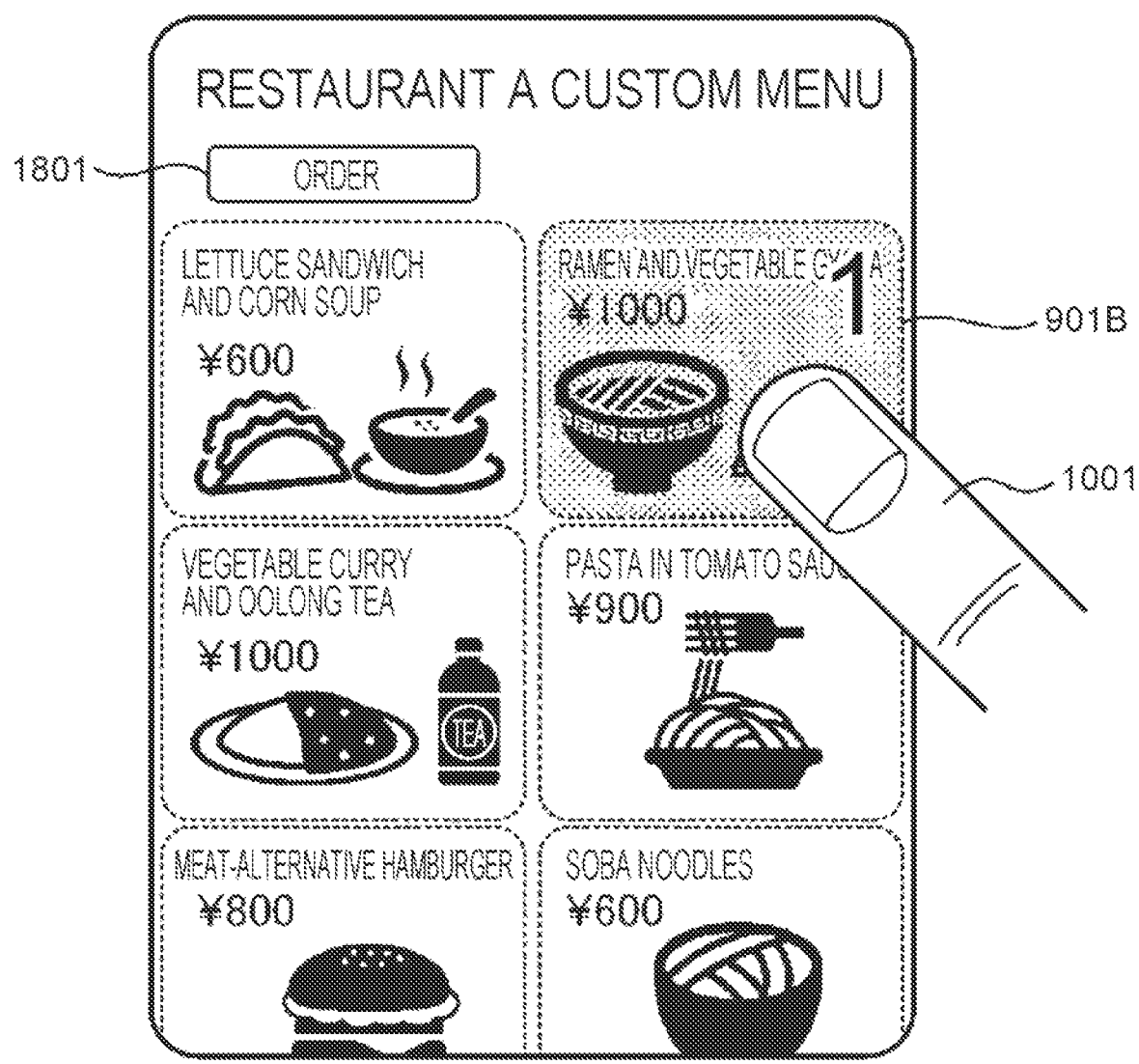
FIG. 19 is a diagram illustrating a scenario in which the user operates the operation screen to order a food from the personalized menu.

The matching app displaying the personalized menu executes a process of receiving the selection of a food to be ordered from the user. This process corresponds to step S5 of FIG. 28. FIG. 19 is a diagram illustrating an example of a scenario in which the user operates the operation screen G106 to order a food from the personalized menu.

In the example of the operation screen G106, a tile object 901B of the food "Ramen and Vegetable Gyoza" has been touched once from the personalized menu. Consequently, the color of the tile object 901B is changed from a first color to a second color, and the order quantity "1" is also displayed in the upper-right corner. In this way, the user can order a food easily and intuitively with a touch operation using a pointing object 1001 such as a finger.

Note that although the color of the tile object 901 is changed when the user selects a food to be ordered, the configuration is not limited thereto. For example, a pattern of the tile object 901 may be changed from a first pattern to a second pattern when the tile object 901 is selected by the user. Alternatively, the color and the pattern of the tile object 901 may be changed from a first color and pattern to a second color and pattern when the tile object 901 is selected by the user.

Figure 20:
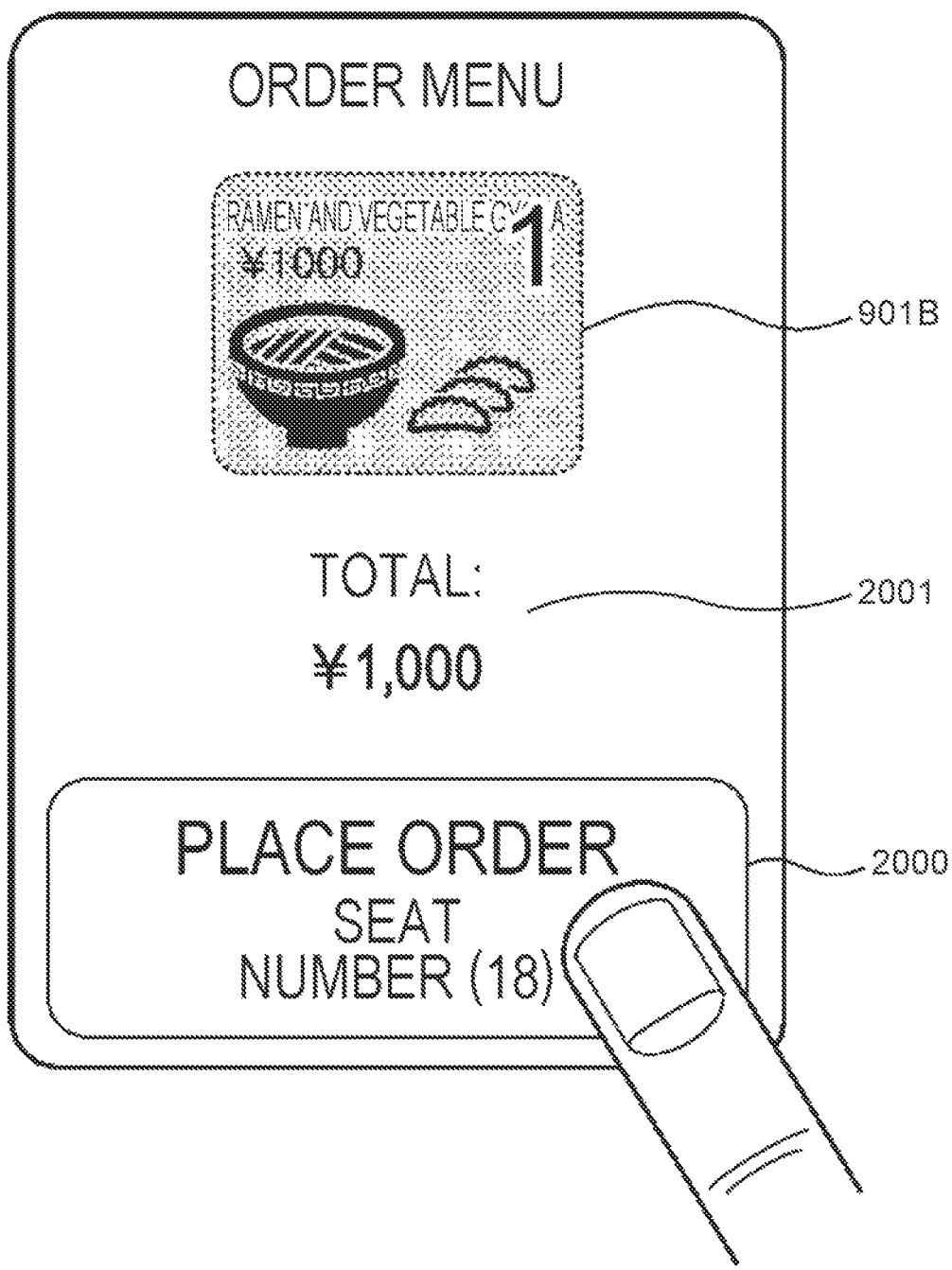
FIG. 20 is a diagram illustrating an example of an operation screen displayed when making a final confirmation of the food to order from the personalized menu.

Having receiving an order of a food through the operation screen G106, the matching app transmits an order request in which the food order information and the seat ID are associated to the second server 300. FIG. 20 is a diagram illustrating an example of an operation screen G107 displayed when making a final confirmation of the food to order from the personalized menu. The operation screen G107 is displayed in the case where the Order button 1801 is touched on the operation screen G106.

On the operation screen G107, the tile object 901B corresponding to the food selected on the operation screen G106 and a total amount 2001 indicating the total (¥1,000) of the ordered food (ramen and vegetable gyoza) are displayed. In addition, an Order button 2000 is included on the operation screen G107. The content of the operation screen G107 is the same as the operation screen G4 for the standard menu. When the Order button 2000 is touched, an order request in which the food order information and the seat ID are associated is transmitted to the second server 300 of Restaurant A. The order request is displayed on a display installed in the store of Restaurant A. With this arrangement, a restaurant staff member can grasp the order content from the displayed seat number "18" and the food order information, start cooking, and serve the ordered food to the seat number "18".

Figure 21:
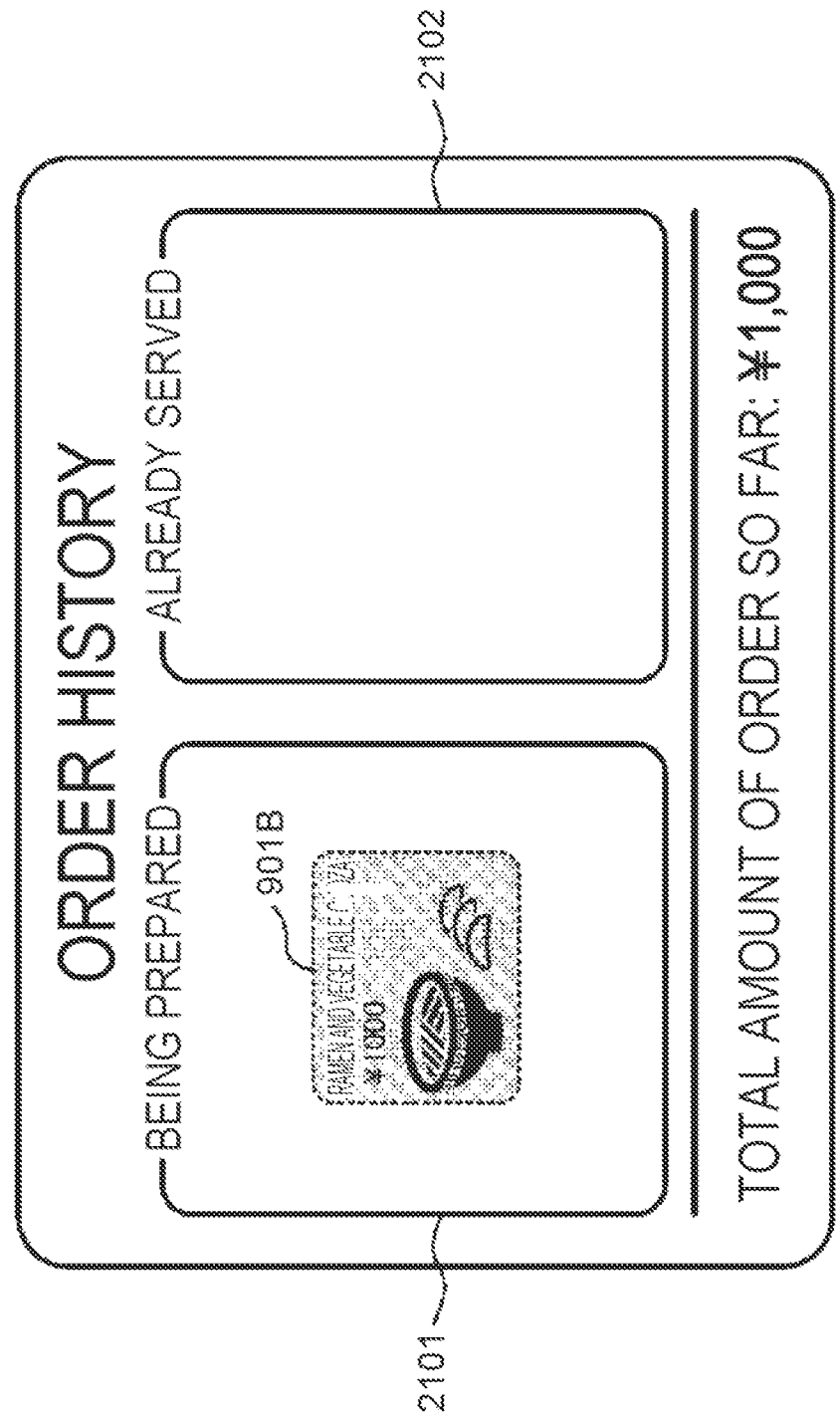
FIG. 21 is a diagram illustrating an example of an order history screen displayed when the user checks the order history so far.

FIG. 21 is a diagram illustrating an example of an order history screen displayed when the user checks the order history so far. The order history screen G108 includes a Being Prepared frame 2101 provided on the left side of the screen and an Already Served frame 2102 provided on the right side of the screen. The tile object 901B is disposed inside the Being Prepared frame 2101 to indicate that the order has been received and the food is currently being prepared. A tile object 901 is disposed inside the Already Served frame 2102 to indicate that the food has been served. In the example of FIG. 20, no foods have been served yet, and therefore no tile object 901 is disposed inside the Already Served frame 2102. Currently, the "Ramen and Vegetable Gyoza" tile object 901B is disposed in the Being Prepared frame 2101. Near the bottom of the order history screen G108, the total (¥1,000) of the food ordered so far through the matching app is displayed in an easily understandable way. By checking the order history screen G108, the user is able to see at a glance the quantity and price of the food ordered so far. Note that an "Order History" button (not illustrated) may also be provided on the operation screen G106, and the order history screen G108 may be displayed when the "Order History" button is touched.

The process of ordering a food from the personalized menu for Restaurant A is performed as above. The user who orders food uses the matching app distributed by the first server 200, and by simply causing the information terminal 100 to read the QR code of the user's seat at the restaurant, the user is able to acquire a personalized menu that accounts for the user's own religion information, and order a food from the personalized menu. This is an unprecedented method of ordering personalized foods conveniently and mistake-free. To execute the method, the user simply installs the matching app in the information terminal 100 in advance.

(Religions)

Next, religions will be described. FIG. 22 is a table summarizing various religions and ingredients that users should avoid according to each religion. In this example of a table, the religions are classified into "Islam", "Judaism", "Hinduism", "Christianity", and "Buddhism". In the table, "X" indicates an ingredient that should be avoided as a general rule according to the corresponding religion. Also, "Y" indicates an ingredient that is preferably avoided according to the corresponding religion, or an ingredient that is stipulated as an ingredient that should be avoided according to certain sects. Hereinafter, an ingredient marked with "X" is referred to as an "ingredient that should be avoided in general", an ingredient marked with "Y" is referred to as an "ingredient that should be avoided if necessary", and both are collectively referred to as an "ingredient that should be avoided".

Islam has food that is permitted to be eaten in accordance with its doctrine (halal food). According to Islam, pork and alcohol are ingredients that should be avoided in general, while fish and dairy are ingredients that should be avoided if necessary.

Judaism has strict dietary laws in accordance with its doctrine (kashrut), and food that is permitted to be eaten (kosher). According to Judaism, pork in particular is an ingredient that should be avoided in general, while chicken, fish, eggs, and dairy are ingredients that should be avoided if necessary.

Hinduism has dietary laws in accordance with its doctrine, in which beef, pork, and fish are ingredients that should be avoided in general, while chicken and eggs are ingredients that should be avoided if necessary.

Christianity has little to no restrictions on eating. However, some sects impose various restrictions related to eating and drinking.

Every religion and sect includes some people who obey dietary laws strictly, and others who do not. Furthermore, people who follow vegetarianism irrespectively of religion have further dietary restrictions. In the present embodiment, it is possible to generate a personalized menu suited to each user with consideration for such circumstances of each user.

For example, the followers of Hinduism, certain sects of Christianity, and certain sects of Buddhism are forbidden or discouraged from consuming animal-based food products. Such followers tend to be deficient in protein, vitamins, calcium, iron, and zinc. People who strictly obey the dietary restrictions of a specific religion refrain from consuming specific ingredients over a long period of time, and consequently tend to have chronic deficiencies in specific nutrients or minerals necessary for maintaining health. To absorb such nutrients that tend to be deficient from limited food products, it is desirable to use ingredients which are allowed to be eaten and which are rich in the nutrients that tend to be deficient in correspondence with the religion or sect to add an ingredient to a food, changing the method of preparing a food, or combine with another food such that a good balance of necessary nutrients is absorbed.

For example, plant-based ingredients rich in vitamin B12 include seaweeds (dried nori, seasoned nori, and toasted nori). Plant-based ingredients rich in vitamin D include mushrooms such as dried shiitake and wood ear. Plant-based ingredients rich in zinc include seaweeds (toasted nori, wakame), vegetables (dried strips of daikon radish, edamame), beans (soybean flour, natto), and the like. Plant-based ingredients rich in calcium include vegetables (Japanese mustard spinach, dried hijiki, bok choy), beans (tofu, natto), and the like. Plant-based ingredients rich in iron include vegetables (Japanese mustard spinach, spinach), beans (natto, deep-fried tofu), and the like. Consequently, it is desirable for users deficient in these nutrients to consume the above ingredients and thereby supplement the deficient nutrients.

Because a user who follows a specific religion needs knowledge like the above to choose foods with consideration for the nutrients that tend to be deficient, and because the practice is burdensome, long-term compliance is thought to be difficult.

Accordingly, in the present embodiment, as described in the second to fifth variations above, the information terminal 100 automatically suggests foods with an added ingredient containing a nutrient that tends to be deficient, foods in which the preparation method has been modified such that a nutrient that tends to be deficient is not destroyed, and combinations of foods capable of supplying a nutrient that tends to be deficient to the user through the personalized menu.

(Data Structure)

Next, the data structure of the religion information and the ingredient information 2400 will be described. FIG. 23 is a diagram illustrating an example of a data structure of information 2300 including user religion information returned from the first server 200 to the matching app. The information 2300 is written as fields and values associated with each other to enable easy processing by an arithmetic device. For example, the information 2300 is contained in a single file in the JavaScript® Object Notation (JSON) format.

An "information category" field indicates what type of personal information is included in the information 2300. The information 2300 includes data related to food, and therefore "food" is written as the value paired with the "information category" field. The "information category" field is written at the beginning of the information 2300.

A "publisher" field is for identifying the corporation that acquired the information 2300 by asking the user through the matching app. Here, questions are asked by ABC Matching Co., Ltd. to acquire the information 2300, and therefore ABC Matching is written as the value corresponding to the "publisher" field.

A "publication date" field indicates the publication date of the information 2300 by the publisher. Here, 2/7/2020 is written as the value corresponding to the "publication date" field. The value may also include a time in addition to the publication date. Also, time zone information may be included in the value.

A "data class" field specifically designates the content of the information 2300. Here, "religion information" for example is written as the value corresponding to the "data class" field. This arrangement indicates that the data written in the subsequent fields is religion information about the relevant user.

Note that it is sufficient for the information terminal 100 to interpret that religion information is included in the information 2300 on the basis of the written content of the values respectively corresponding to the "information category" field and the "data class" field. Alternatively, the information terminal 100 may interpret that religion information is included in the information 2300 on the basis of information related to the information 2300 (for example, the file name of the information 2300).

A "data measurement date" field indicates date information about when the value "religion information" corresponding to the preceding "data class" field was measured. Here, 2/7/2020 is written as the value corresponding to the "data measurement date" field. The value may also include a time in addition to the measurement date. Also, time zone information may be included in the value. Note that in the case where a plurality of religion information is stored for the relevant user in the first server 200, the information 2300 with the most recent date written in the "data measurement date" field is used.

"Religion type" indicates the religion embraced by the user. The various religions listed in FIG. 22 may be adopted as the "religion type". Alternatively, the religion type may include information indicating a sect in addition to information indicating a religion. Here, because the relevant user is Buddhist, "Buddhism" is written as the value corresponding to "religion type".

After the "religion type" field, resistance values indicating the degree of resistance the user feels against eating each of the ingredients of beef, pork, chicken, fish, eggs, dairy, and alcohol are written. The resistance value is expressed in six levels from 0 to 5, for example, with a larger numerical value indicating a lower level of resistance. For example, an ingredient with a resistance value of "0" is an ingredient that should be avoided absolutely, whereas an ingredient with a resistance value of "5" is an ingredient for which the user feels no resistance against eating.

Because the "religion type" of the user is Buddhism, beef, pork, chicken, and fish are ingredients that should be avoided if necessary, and consequently the resistance values of these ingredients are set to "1". On the other hand, eggs, diary, and alcohol are ingredients that the user is allowed to eat, and consequently the resistance values of these ingredients are set to "3", "5", and "5". The reason why the resistance value of eggs is "3" is that the user feels some resistance against eating eggs. As illustrated by the table in FIG. 22, the ingredients that should be avoided are predetermined according to religion. For this reason, the resistance value of each ingredient is set by default to "0" for ingredients that should be avoided in general, "1" for ingredients that should be avoided if necessary, and "5" for ingredients that are allowed to be eaten. However, the user is able to input a resistance value less than "5" through the matching app with respect to ingredients that the user is allowed to eat, but for which the user feels resistance against eating. Also, even if an ingredient is an ingredient that should be avoided in general, a user who does not strictly adhere to the doctrine of the religion is able to input a resistance value greater than "0" through the matching app with respect to ingredients that should be avoided in general. In addition, the user is also able to input a resistance value greater than "1" with respect to ingredients that should be avoided if necessary.

The resistance values are an example of level information indicating the degree to which to avoid an ingredient that should be avoided according to the religion of the user.

On the other hand, unless ingredient information for each food is described in the menu information acquired from the second server 300 of Restaurant A, the information terminal 100 is unable to specify which foods contain ingredients that should be avoided by each user. FIG. 24 is a diagram illustrating an example of a data structure of the ingredient information 2400 forming the menu information returned from the second server 300. In FIG. 24, ingredient information 2401 for the Ramen B Set is illustrated. The Ramen B Set includes shoyu ramen and soup dumplings. Consequently, when determining whether or not the Ramen B Set contains ingredients that should be avoided by the user, the information terminal 100 references ingredient information 2402 for shoyu ramen and ingredient information 2403 for soup dumplings.

The ingredient information 2400 is written as fields and values associated with each other to enable easy processing by an arithmetic device. The ingredient information 2400 is embedded together with tags indicating the ingredient information in menu information in HTML file format for example that is acquired from the second server 300 of each restaurant. However, this is merely an example, and the ingredient information 2400 may also be structured in JSON format and contained in a separate file prepared for each food.

The "food name" field indicates the food to which the ingredient information relates. The Ramen B Set is written as the value corresponding to the "food name" field in the example of the ingredient information 2401, shoyu ramen is written as the value corresponding to the "food name" field in the example of the ingredient information 2402, and soup dumplings is written as the value corresponding to the "food name" field in the example of the ingredient information 2403.

A list of the ingredients used is written in the fields and values following the "food name" field. For example, because the Ramen B Set includes a bowl of shoyu ramen and three soup dumplings, the ingredient information 2401 includes a "shoyu ramen" field and a "soup dumpling" field, in which "1" is written as the value corresponding to shoyu ramen and "3" is written as the value corresponding to soup dumpling. Because the ingredient information 2401 is ingredient information 2400 for a food set, field and values related to the ingredients contained in the foods are not provided.

The ingredient information 2402 is ingredient information 2400 for shoyu ramen as a single dish, and therefore each ingredient and the quantity of each ingredient contained in shoyu ramen, such as "50 g" of "flour" and "5 g" of "salt", are written in association with each other. Like the ingredient information 2402, the ingredient information 2403 is also ingredient information 2400 for soup dumplings as a single dish, and therefore each ingredient and the quantity of each ingredient contained in a soup dumpling are written in association with each other.

As indicated by the ingredient information 2402 and the ingredient information 2403, the Ramen B Set contains "pork char siu", "ground pork", and "chicken stock" as ingredients. However, in the information 2300 about the user, the resistance value is set to "1" for each of pork and chicken, indicating that "ground pork" and "chicken stock" are ingredients that should be avoided if necessary for the user. Consequently, it is desirable for the user not to eat the Ramen B Set. Accordingly, the arithmetic unit 104 of the information terminal 100 suggests the food set of ramen and vegetable gyoza illustrated in FIG. 25 instead of the Ramen B Set for example to the user through the personalized menu.

FIG. 25 is a diagram illustrating an example of ingredient information 2404 for ramen and vegetable gyoza. As indicated by the ingredient information 2405 and the ingredient information 2406, in the ramen and vegetable gyoza, bok choy is used instead of pork char siu, Chinese leek is used instead of ground pork, and cabbage is used instead of chicken stock. With this arrangement, "ramen and vegetable gyoza" that the user is allowed to eat is displayed on the personalized menu, and the user is able to order a food that he or she is allowed to eat smoothly from the personalized menu.

When substituting foods, the information terminal 100 cross-references the ingredient information 2402 and the ingredient information 2403 illustrated in FIG. 24 with the religion information included in the information 2300 about the user, and extracts ingredients to be replaced from among the ingredient information 2402 and the ingredient information 2403. For example, ingredients with a resistance value of "0" or "1" in the information 2300 are extracted as ingredients to be replaced in the ingredient information 2402 and the ingredient information 2403. The ingredients extracted as the ingredients to be replaced are labeled "Bad" in the ingredient information 2402 and the ingredient information 2403. Additionally, the information terminal 100 substitutes the ingredient information 2402 and the ingredient information 2403 by replacing the ingredients to be replaced and their quantities with alternative ingredients and alternative quantities predetermined for each food with respect to the extracted ingredients to be replaced. Furthermore, the information terminal 100 substitutes the food name in the ingredient information with a predetermined food name according to the replaced ingredients. With this arrangement, the ingredient information 2400 illustrated in FIG. 25 is obtained. It is sufficient for the information terminal 100 to substitute foods by applying the above process to each food included in the acquired menu information.

Alternatively, if an alternative food is predetermined according to religion for a food containing an ingredient to be replaced, the information terminal 100 may substitute the food containing the ingredient to be replaced with an alternative food.

(Overall Picture of Process)

Figure 26:
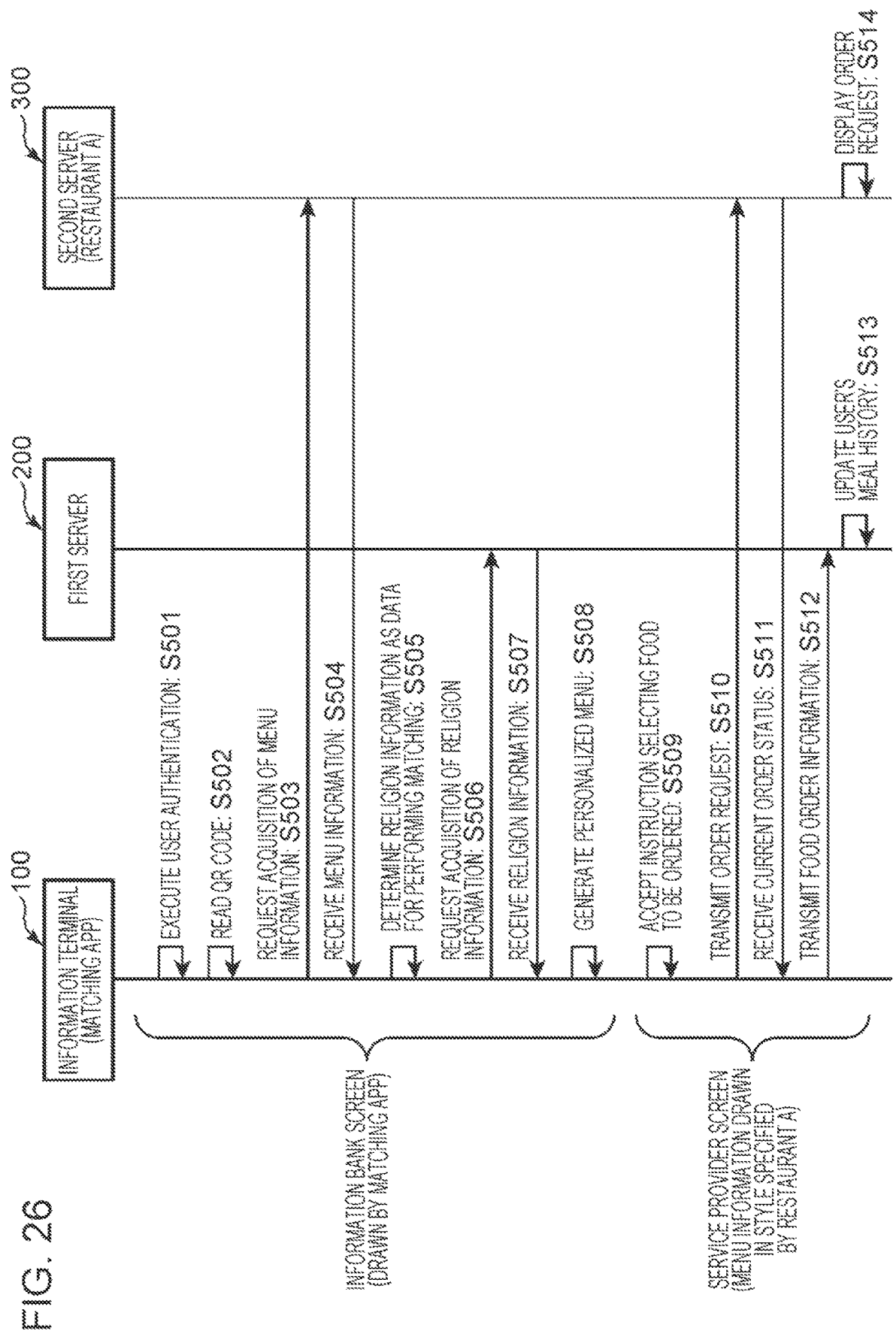
FIG. 26 is a sequence diagram illustrating an example of an overall picture of a process by the information processing system according to the present embodiment.

Next, an overall picture of a process by the information processing system according to the present embodiment will be described. FIG. 26 is a sequence diagram illustrating an example of an overall picture of a process by the information processing system according to the present embodiment.

The matching app, launched by the information terminal 100 in accordance with an operation performed by the user who enters and takes a seat in Restaurant A, executes user authentication (step S501). If user authentication is successful, the matching app displays the home screen G103 (see FIG. 14).

If the Scan button 1402 is touched by the user on the home screen G103, the matching app launches a scan function and acquires the QR code corresponding to the user's seat (step S502). With this arrangement, the matching app acquires the URL of the second server 300 (HTTP server) of Restaurant A treated as the destination.

Having acquired the URL, the matching app transmits a request (for example, an HTTP request) for acquiring menu information to the second server 300 of the Restaurant A on the basis of the URL (step S503). At this point, the matching app may also transmit the seat ID included in the QR code as described above to the second server 300.

The second server 300 receiving the request uses an HTTP server function to transmit an HTTP response containing the menu information. With this arrangement, the matching app receives the menu information of Restaurant A (step S504).

The matching app receiving the menu information analyzes the received menu information and detects that the data attribute of the received menu information is the food attribute. In this case, it is sufficient if the matching app detects the food attribute through internal analysis of the menu information. Alternatively, the matching app may detect the food attribute from supplemental information transmitted separately from the menu information. Thereafter, because the data attribute of the received menu information is the food attribute, the matching app determines religion information as the data for performing matching (step S505).

Next, the matching app transmits an HTTP request for acquiring the religion information of the user to the first server 200 on the basis of the user ID of the authenticated user (step S506). The first server 200 receives the HTTP request using an HTTP server function, extracts the religion information of the user from the memory 203 on the basis of the user ID, and transmits an HTTP response containing the extracted religion information to the matching app. With this arrangement, the matching app receives the religion information of the user (step S507).

The matching app receiving the religion information uses one of the methods indicated by the five variations described above to generate a personalized menu corresponding to the religion information of the user from the received menu information and the received religion information (step S508).

The matching app generates the style (user interface (UI) design) of the various screens displayed in the process from step S501 to step S508 according to the style of the matching app, but generates the style (for example, UI design) of the various screens from the personalized menu to order completion according to a style provided by Restaurant A. In other words, each business (for example, each restaurant) that acts as a service provider is able to communicate with users (for example, customers) in a style (for example, UI design) preferred by each business while also remaining within the matching app developed by another company (for example, the information bank or an information intermediary). This means that each of the standard menu and the personalized menu described above can be expressed in a style (for example, UI design) designated by Restaurant A, and furthermore, the menus can be given a uniform appearance.

Having generated the personalized menu, the matching app displays the operation screen G106 including the generated personalized menu in a style designated by Restaurant A, and accepts an instruction selecting a food to be ordered by the user from the personalized menu (step S509).

Having accepting the selection instruction, the matching app transmits an order request in which the user's seat ID and food order information indicating the food to be ordered are associated to the second server 300 of Restaurant A (step S510). The second server 300 receiving the order request replies to the matching app with an acknowledgment (ACK) indicating that the order has been received, and with the current order status (for example, information related to the order history screen G108) as necessary. With this arrangement, the matching app receives the current order status (step S511).

The matching app also sends the food order information with respect to the second server 300 of Restaurant A to the first server 200 in association with the user ID (step S512), and requests an addition or update to the user's meal history information. The first server 200 receiving the food order information updates the user's meal history information according to the received food order information (step S513). In this case, a time stamp indicating the order time of the food indicated by the food order information is also added to the meal history information.

The second server 300 of Restaurant A receiving the order request displays the order request on a display inside the store (step S514). With this arrangement, an employee in the store is able to serve the ordered food to the seat of the ordering user without making a mistake.

In this way, detailed and accurate meal history information is accumulated chronologically in the first server 200 as a portion of the personal information about the user. With this arrangement, such big data is utilized the next time the user places an order, and food choices that are highly compatible with the user are presented to the user more precisely.

According to the control method illustrated in FIG. 26, it is possible to lower the risk of a user who has ordered a food being mistakenly served a food which is different from the order and which contains an ingredient that should be avoided by the user for religious reasons. Furthermore, according to the control method illustrated in FIG. 26, even if a user has strict requirements regarding ingredients that should be avoided, the preparation method, and the like, the user is able to order a food without having to confirm such requirements with the restaurant, and furthermore, the restaurant is also able to accommodate an orders of a food from such a user easily. Also, according to the control method illustrated in FIG. 26, user unease about communicating personal information concerning the user's privacy such as religion information to the restaurant staff and user unease about personal information concerning the user's privacy being accumulated in a store terminal are reduced.

Furthermore, according to the control method illustrated in FIG. 26, accurate and chronologically continuous personal information including religion information, meal history information (for example, order history information), activity level, vital sign information, and the like can be managed efficiently and securely. Moreover, according to the control method illustrated in FIG. 26, personal information is prevented from being leaked to an entity other than a business that has obtained the user's consent.

(Flowchart of Process of Ordering)

Next, a process by the information terminal 100 according to the present embodiment will be described. FIG. 27 is a flowchart illustrating an example of a process by the information terminal 100 in a case where a food is ordered from the standard menu. The flowchart is initiated when triggered by the launching of the QR code reader by the user on the information terminal 100.

In step S11, the QR code reader reads a QR code and passes the read character string (for example, an URL) to the browser. In this process, the QR code is read using the operation screen G1 illustrated in FIG. 7, and the result of reading the QR code is displayed on the operation screen G2 illustrated in FIG. 8.

In step S12, the browser accesses the second server 300 of Restaurant A according to the URL, acquires menu information, and displays the standard menu on the display 105 of the information terminal 100. In this process, the operation screen G3 including the standard menu illustrated in FIG. 9 is displayed.

In step S13, the browser accepts, from the user, an instruction of selecting a food to be ordered from the standard menu. In this process, the standard menu included on the operation screen G3 illustrated in FIG. 10 is operated by the user to select the food to be ordered.

In step S14, the browser transmits an order request in which the user's seat ID and food order information indicating the food ordered by the user are associated to the second server 300 of Restaurant A. With the above, the process of ordering from the standard menu is completed.

In this way, a user who wants to order from an appropriate menu with consideration for the user's own religion information at a restaurant uses the matching app to display a personalized menu from which to order a food. On the other hand, a user who wants to select a food from the standard menu of the restaurant without consideration for the user's own religion information uses a general-purpose QR code reader to display the standard menu from which to order a food.

In either case, because the seat ID read from the QR code corresponding to the seat where the user is sitting is transmitted in association with the food order information to the second server 300, the ordered food is served mistake-free.

Figure 28:
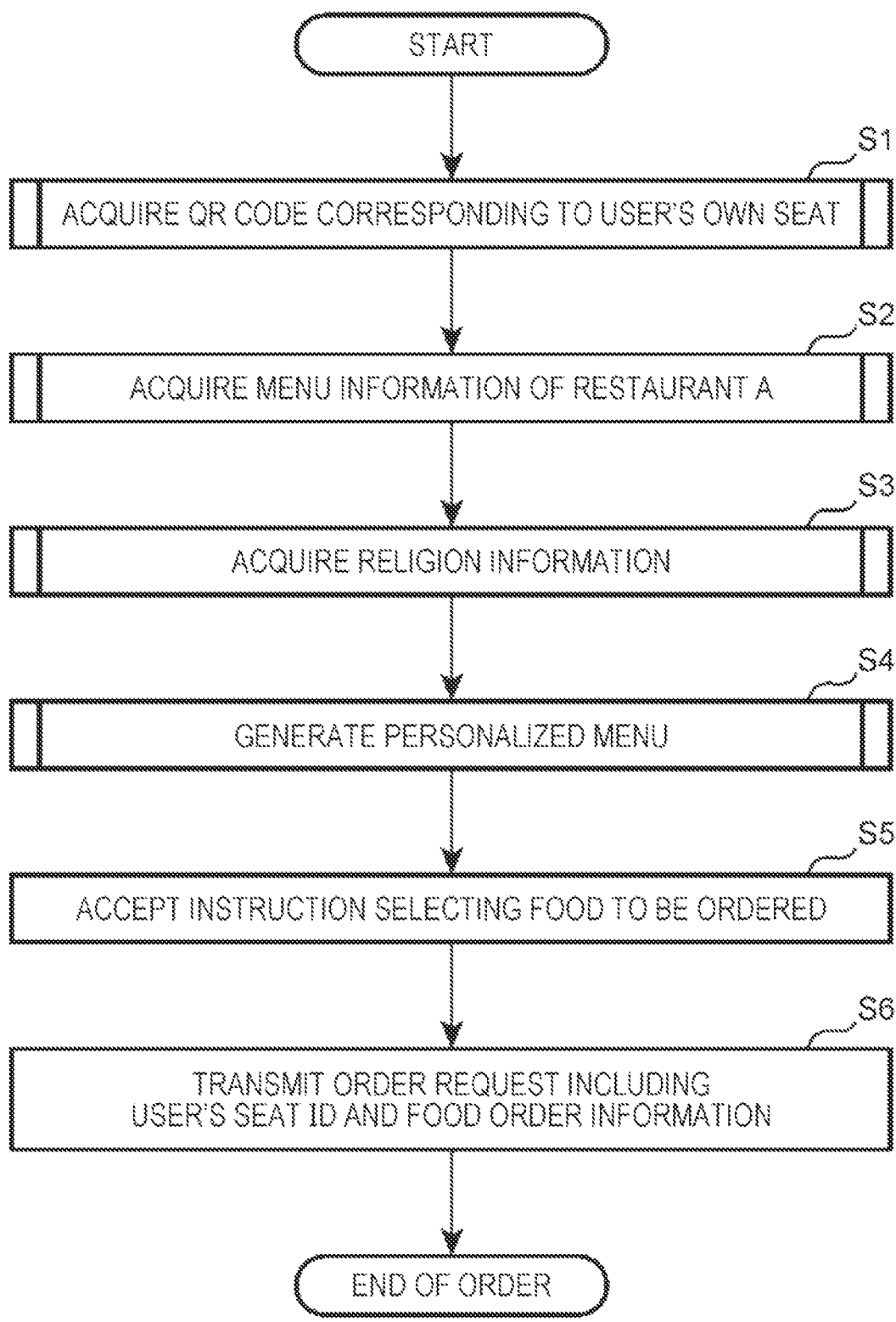
FIG. 28 is a flowchart illustrating an example of a process by the information terminal in a case where a food is ordered from the personalized menu.

FIG. 28 is a flowchart illustrating an example of a process by the information terminal 100 in a case where a food is ordered from the personalized menu. The flowchart is initiated when triggered by the launching of the matching app by the user who enters a restaurant to order a food.

In step S1, the matching app executes a process of acquiring the QR code corresponding to the user's seat. Details of this process will be described later using FIG. 29. In this process, the QR code is read through the operation screen G104 illustrated in FIG. 15, and the seat ID and the restaurant ID are acquired. This process corresponds to steps S501 and S502 of FIG. 26.

In step S2, the matching app executes a process of using a browser function to access the URL indicated by the acquired QR code and acquiring the menu information of Restaurant A from the second server 300 of Restaurant A. Details of this process will be described later using FIG. 30. In this process, the data attribute of the menu information is also detected to be the food attribute. In this process, the display screen G105 illustrated in FIG. 17 is displayed on the information terminal 100. This process corresponds to steps S503 and S504 of FIG. 26.

In step S3, the matching app executes a process of acquiring personal information related to the food attribute, namely religion information, from among the personal information of the user from the first server 200. Details of this process will be described later using FIG. 31. According to this process, the religion information of the user sitting in the seat indicated by the seat ID acquired in step S1 is acquired. This process corresponds to steps S505, S506, and S507 of FIG. 26.

In step S4, the matching app executes a process of cross-referencing the menu information of Restaurant A with the religion information of the user and generating a personalized menu including foods compatible with the religion. Through this process, the operation screen G106 including the personalized menu is displayed. This process corresponds to step S508 of FIG. 26.

In step S5, the matching app accepts an instruction of selecting a food to be ordered by the user viewing the personalized menu. In this case, the food is selected as illustrated by the operation screen G106 in FIG. 19. This process corresponds to step S509 of FIG. 26.

In step S6, the matching app transmits an order request in which food order information indicating the food selected in step S5 is associated with the seat ID acquired in step S1 to the second server 300 of Restaurant A. This process corresponds to step S510 of FIG. 26.

Figure 29:
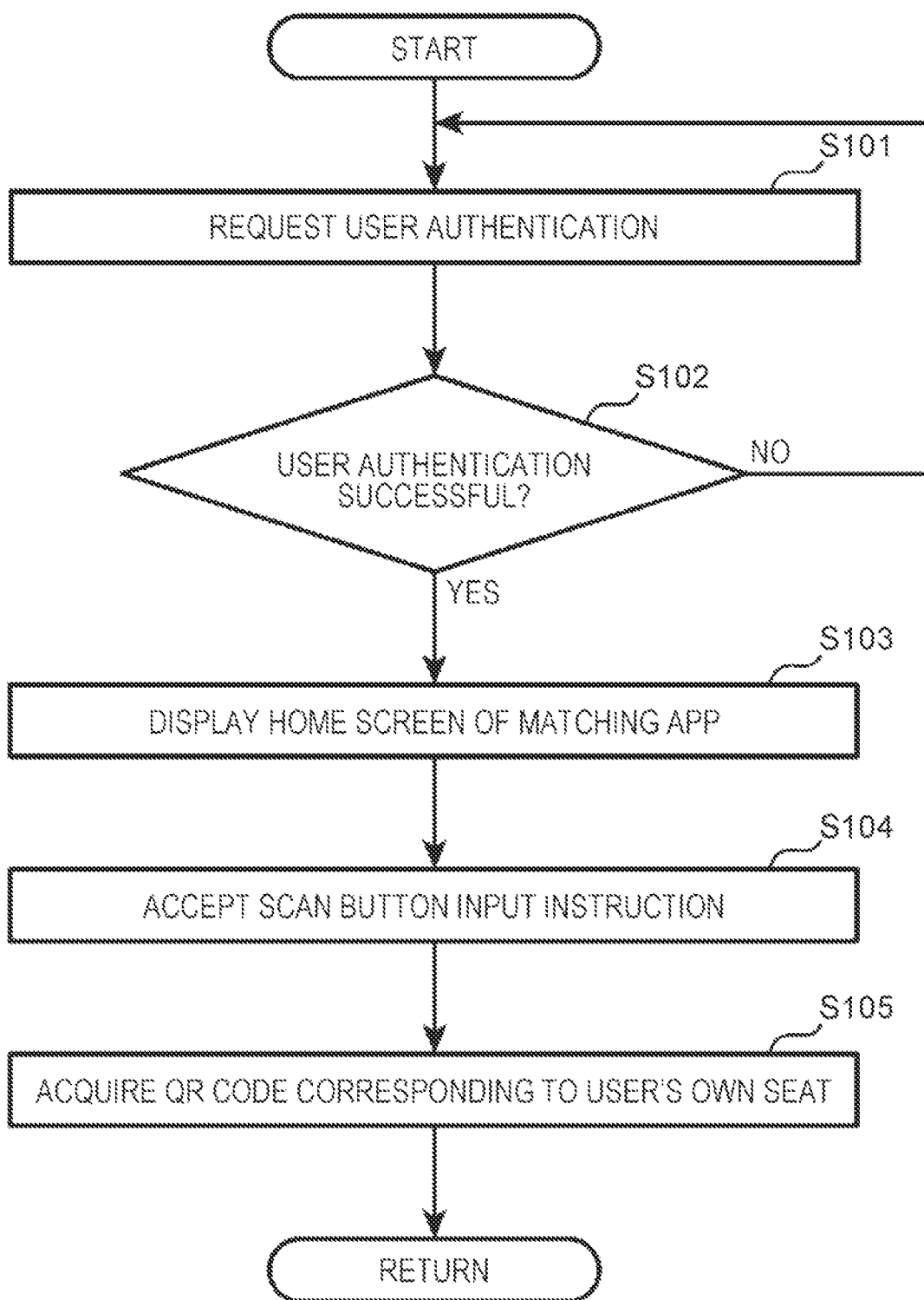
FIG. 29 is a flowchart illustrating details of the process in step S1 of FIG. 28.

Hereinafter, details of the case where a food is ordered from the personalized menu will be described. FIG. 29 is a flowchart illustrating details of the process in step S1 of FIG. 28. In step S101, the matching app launched by the user requests the user to perform user authentication. In this case, user authentication using the authentication screen G101 illustrated in FIG. 12 or the authentication screen G102 illustrated in FIG. 13 is performed.

In step S102, the matching app determines whether or not the user authentication is successful. At this point, if user authentication is unsuccessful (step S102, NO), the process returns to step S101. If user authentication is successful (step S102, YES), the process proceeds to step S103. In step S103, the matching app displays the home screen G103 of the matching app illustrated in FIG. 14.

In step S104, the matching app accepts a user operation of touching the Scan button 1402 on the home screen G103, and launches a QR code reading function. With this arrangement, the operation screen G104 illustrated in FIG. 15 is displayed. Note that in the case of adopting a configuration that reads the restaurant ID and the seat ID through NFC, the operation screen G1011 illustrated in FIG. 16 is displayed.

In step S105, the direction and position of the information terminal 100 are adjusted by the user, and the matching app reads the QR code corresponding to the seat where the user is sitting.

Figure 30:
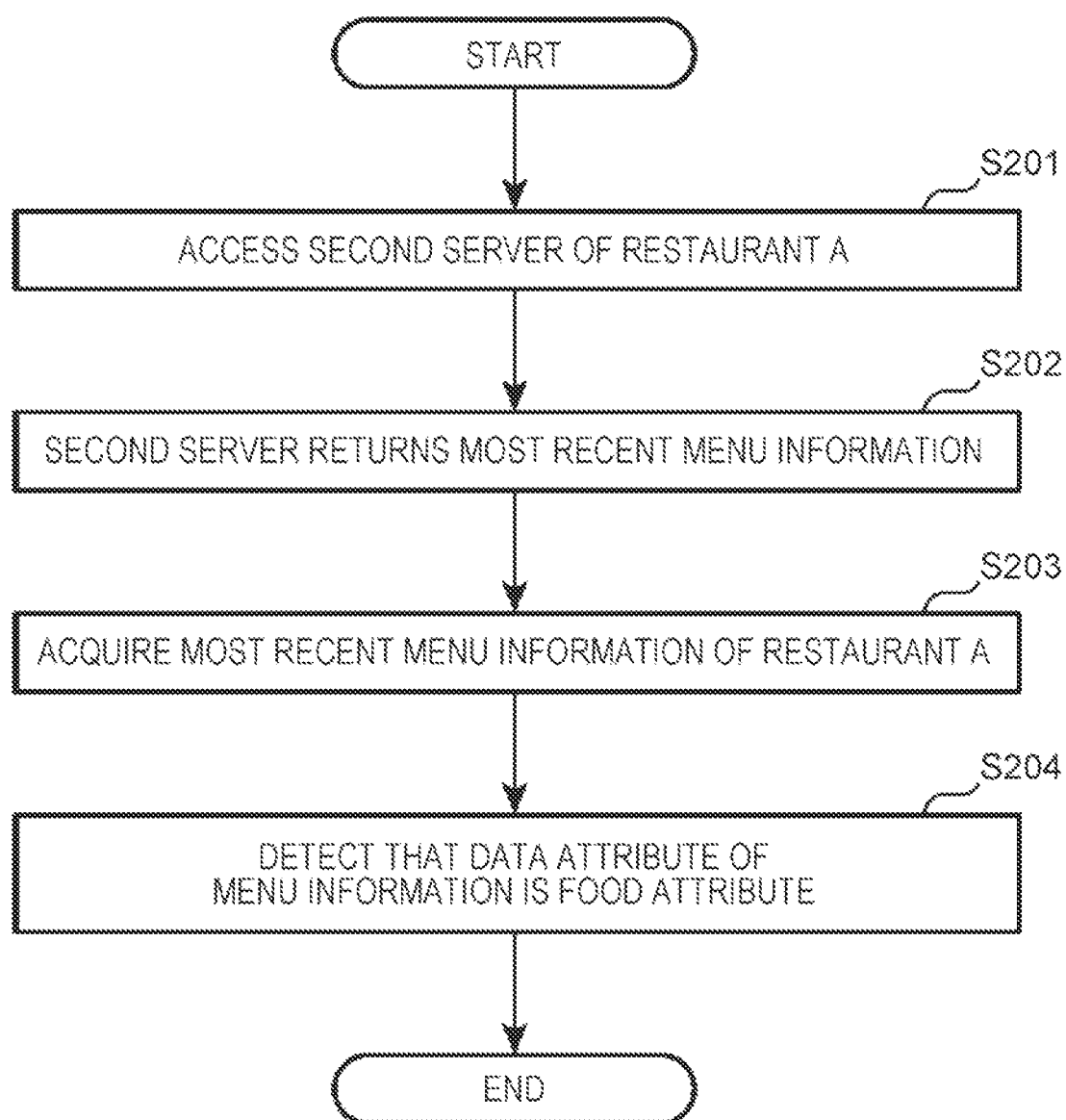
FIG. 30 is a flowchart illustrating details of the process in step S2 of FIG. 28.

FIG. 30 is a flowchart illustrating details of the process in step S2 of FIG. 28. In step S201, the matching app accesses the second server 300 of Restaurant A on the basis of the character string (for example, a URL) expressed by the QR code. This access is performed through an HTTP request, for example.

In step S202, the second server 300 of Restaurant A uses an HTTP server function to reply to the matching app with the most recent menu information. The reply is performed through an HTTP response, for example.

In step S203, the matching app acquires the most recent menu information of Restaurant A.

In step S204, the matching app detects from the acquired menu information that the data attribute of the menu information is the food attribute. This detection is performed on the basis of a data attribute written in an HTML file containing the menu information, for example.

Figure 31:
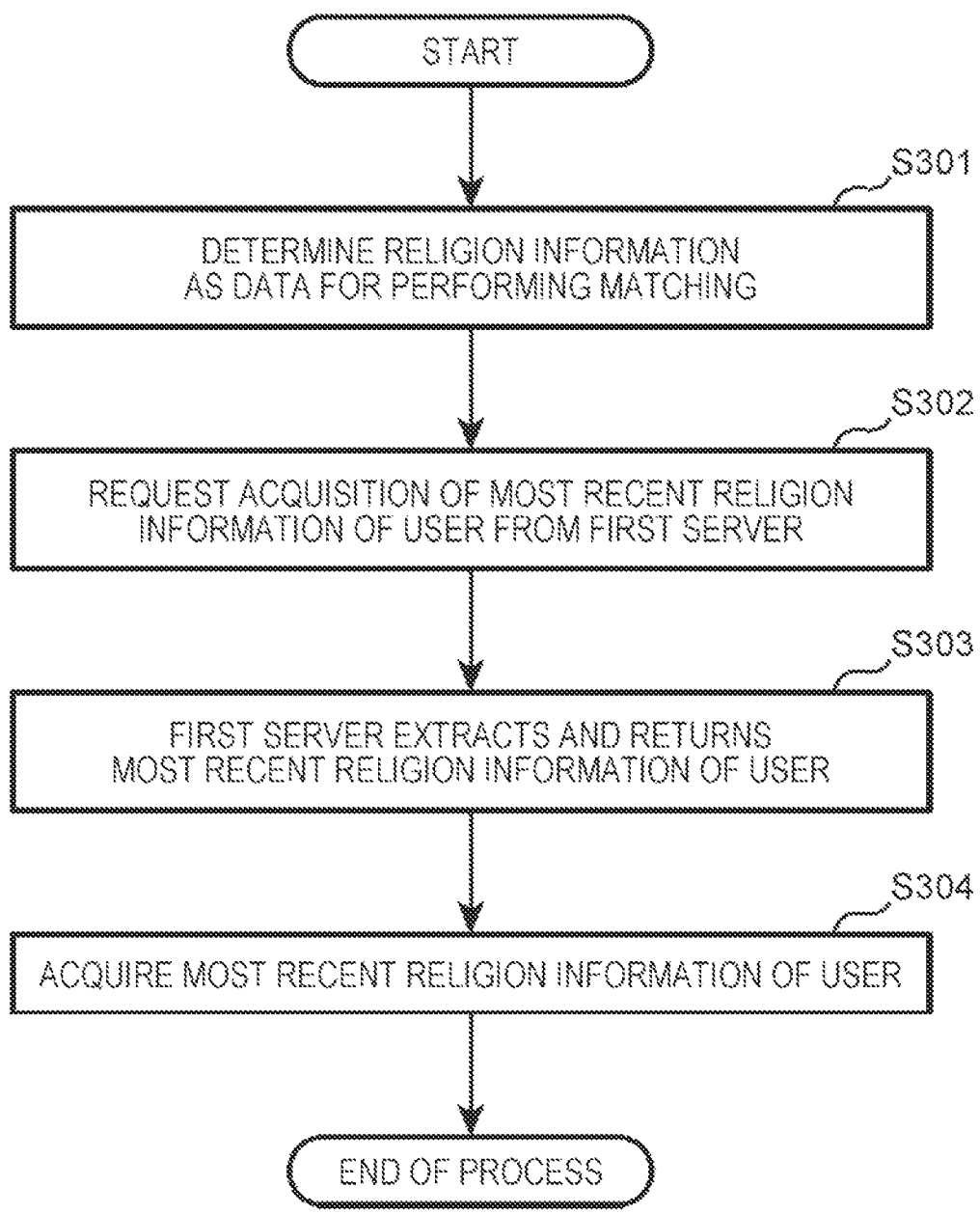
FIG. 31 is a flowchart illustrating details of the process in step S3 of FIG. 28.

FIG. 31 is a flowchart illustrating details of the process in step S3 of FIG. 28. In step S301, because the data attribute of the acquired menu information is the food attribute, the matching app determines the religion information of the user as the data for performing matching.

In step S302, the matching app requests the first server 200 for the acquisition of the most recent religion information of the user treated as the target of matching. In this case, the matching app specifies the user ID and requests a reply containing the religion information in a predetermined encrypted state.

In step S303, the first server 200 extracts the most recent religion information on the basis of the user ID from among an enormous amount of personal information being distributively encrypted and managed, and after converting the religion information to a predetermined format, applies a predetermined encryption and replies to the matching app.

In step S304, the matching app decrypts the acquired most recent religion information. With this arrangement, the most recent religion information of the user is acquired.

Figure 32:
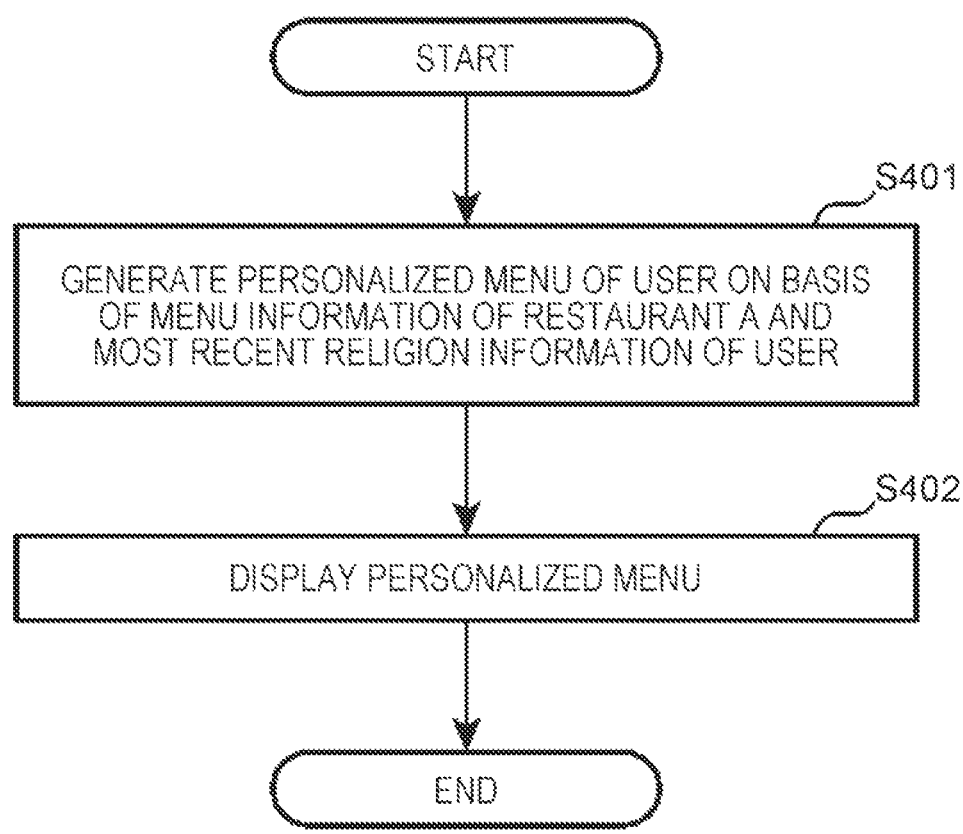
FIG. 32 is a flowchart illustrating details of the process in step S4 of FIG. 28.

FIG. 32 is a flowchart illustrating details of the process in step S4 of FIG. 28. In step S401, the matching app cross-references the menu information of Restaurant A with the most recent religion information of the user, and generates a personalized menu including only foods compatible with the user's religion. As described later, the menu information includes one or more ingredients included in each food, and the quantity of each ingredient. The menu information may also include preparation method information indicating the preparation method of each food. At this point, the personalized menu is generated using one of the methods indicated by the five variations described above.

In step S402, the matching app uses the browser function to generate and display the operation screen G106 including the generated personalized menu on the display 105 of the information terminal 100. In this case, the personalized menu is displayed with style information included in the menu information of Restaurant A applied thereto, for example.

(Example Implementation of Information Processing when Ordering from Personalized Menu)

Next, an example implementation of the information processing in the case of ordering from the personalized menu will be described. In the case where the interface for information communication and data structure to be handled are unique to the restaurant location (that is, store), situations may occur in which the various data handled by the information processing system is usable at the store 40 of Restaurant A but unusable by Restaurant B, or unusable by both at a different store of Restaurant A and Restaurant B. To avoid such situations, a general-purpose solution enabling many users to order foods using personalized menus from many restaurants is described hereinafter.

Figure 33:
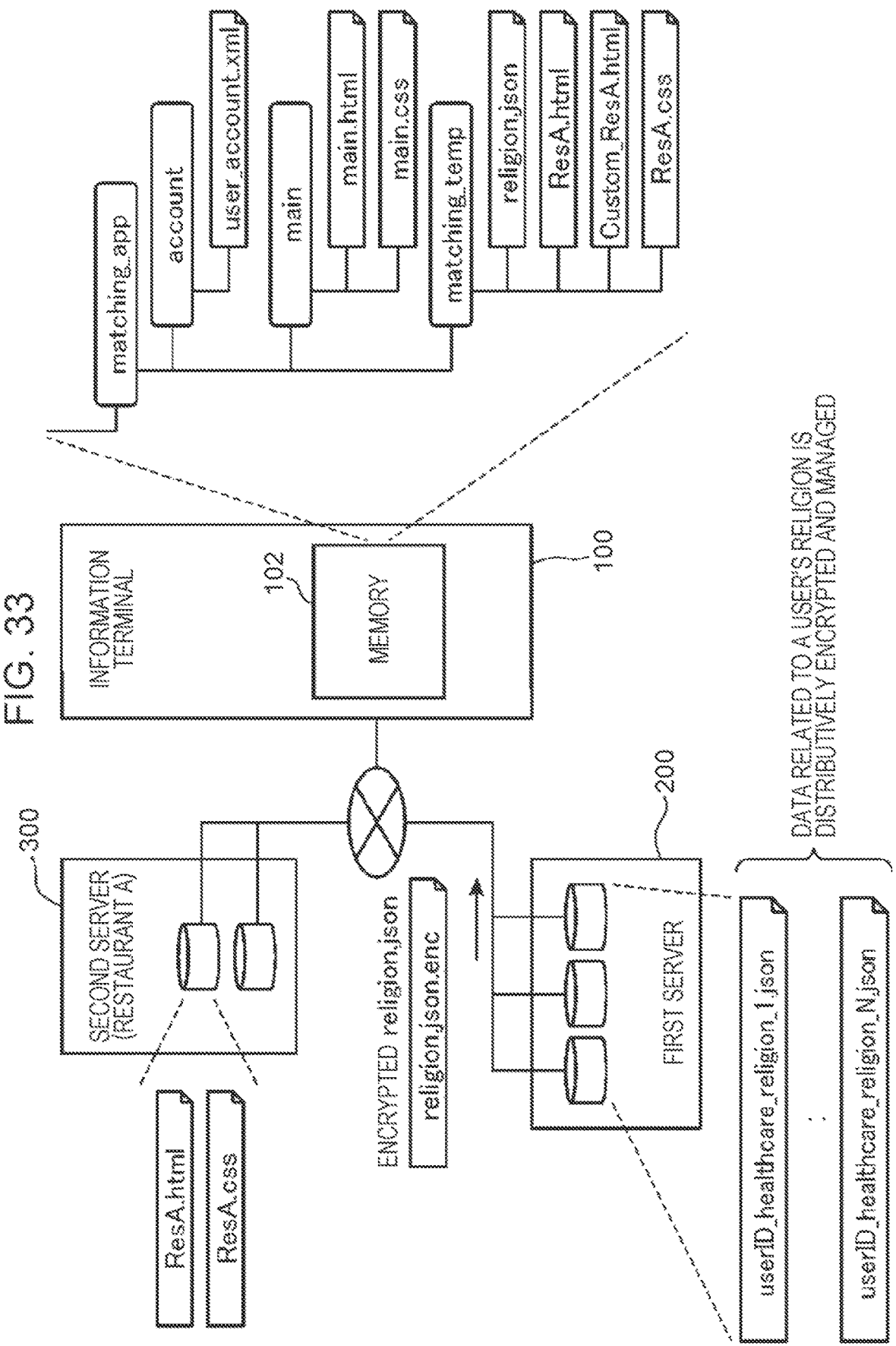
FIG. 33 is a diagram illustrating an example of a specific implementation of the information processing system according to the present embodiment.

FIG. 33 is a diagram illustrating an example of a specific implementation of the information processing system according to the present embodiment. The memory 102 of the information terminal 100 contains a "matching_app" directory, which is a storage location for files necessary to execute the matching app. Under the "matching_app" directory, there are an "account" directory, a "main" directory, and a "matching_temp" directory. In the "account" directory, a user account and/or information necessary for user authentication are stored. In the "main" directory, information necessary for the matching app to achieve basic functions such as drawing the home screen and scanning a QR code is stored. In the "matching_temp" directory, information necessary for matching is stored temporarily.

In the "account" directory, a "user_account.xml" file describing an account and/or information necessary for user authentication is stored. In the "user_account.xml" file, a unique account name (for example, a user ID specified by the user) and corresponding authentication information (for example, a password, fingerprint features, and/or face features) are recorded in an encrypted form as information for specifying the user, for example.

The account name is not limited to a user ID specified by the user, and any information that can be used to individually identify a user who uses the matching app may be adopted. For example, a unique serial code assigned to each instance of the matching app, embedded into the program of the matching app, and distributed together with the matching app may also be adopted. The unique serial code assigned to each instance refers to a serial code uniquely assigned for each information terminal 100 in which the matching app is installed. Alternatively, a unique account name generated by the matching app on the basis of a random number when the matching app is launched for the first time or when registration is performed for the first time may also be adopted as the account name. In this case, it is sufficient for the matching app to generate the account name automatically by checking with the first server 200 to confirm that the account name does not overlap with an existing account name already registered, for example.

Setting character string information that is unintelligible to humans as the account name in this way makes it possible to communicate personal information with increased anonymity. The religion information included in the personal information illustrated in FIG. 33 is managed by being fragmented into a plurality of files as described later. The account name described above may also be adopted for the userID portion of the file name in each fragmented file. Alternatively, different information paired 1:1 with the account name described above may be adopted for a portion of the file name (for example, the userID portion) of each fragmented file.

In the "main" directory, a "main.html" file describing content information necessary for achieving the basic functions of the matching app and a "main.css" file describing the style (for example, UI design) of the screen display are stored.

In the second server 300 of Restaurant A, a group of files to reply with when the URL (for example, http://restaurantA.com/QRorder-18) expressed by a character string obtained as a result of reading a QR code is stored in advance. The group of files includes a "ResA.html" file describing the content information included in the reply and a "ResA.css" file describing the style (for example, UI design) of the screen display of the content information. For example, the ingredient information 2400 illustrated in FIGS. 24 and 25 may be included in "ResA.html", or stored in an external file referenced in the "ResA.html" file.

In the first server 200, a huge variety of personal information about the user is accumulated in a distributively encrypted form. For example, the religion information of the user used in the present disclosure is archived in physically different storage devices in the first server 200 as N files in JSON format named "userID_healthcare_religion_1.json", "userID_healthcare_religion_2.json", . . . , "userID_healthcare_religion_N.json". In the N files, the "userID" at the beginning of the file name is identification information for specifying the target user, the following "healthcare" is identification information for specifying the information category (for example, food) described using FIG. 23, the following "religion" is identification information for specifying the data class (for example, religion information) described using FIG. 23, and the final numeral is an identification number of the divided file.

If a request for the religion information of the user is received together with appropriate permissions (for example, access right information), the first server 200 correctly decrypts data from the N files and converts the data into a predetermined description format (.json) to acquire a "religion.json" file, and replies to the matching app with a "religion.json.enc" file obtained by encrypting the "religion.json" file.

Figure 34:
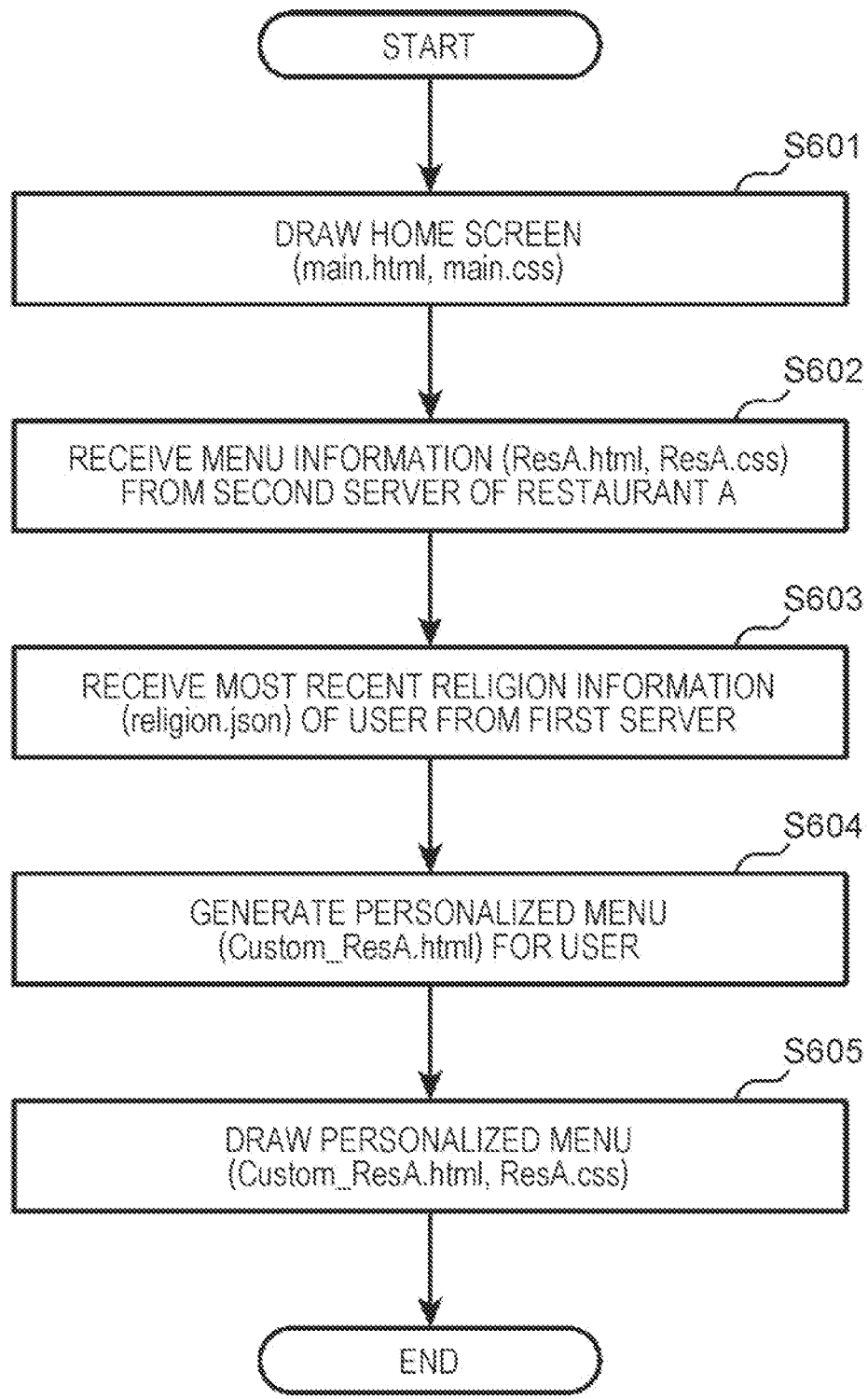
FIG. 34 is a flowchart illustrating an example of a process by the matching app with respect to files from the launching of the matching app until the personalized menu is displayed.

Hereinafter, the handling of files in the case where the matching app performs screen control using HTML will be described according to the flowchart in FIG. 34. FIG. 34 is a flowchart illustrating an example of a process by the matching app with respect to files from the launching of the matching app until the personalized menu is displayed.

In step S601, the matching app launches and draws the home screen. The matching app draws the home screen using the "main.html" file and the "main.css" file in the "main" directory immediately after launching. With this arrangement, the home screen G103 illustrated in FIG. 14 is drawn.

In step S602, the matching app receives menu information from the second server 300 of Restaurant A. The received menu information is recorded as the "ResA.html" file and the "ResA.css" file in the "matching_temp" directory.

In step S603, the matching app receives the encrypted religion information (religion.json.enc) of the user from the first server 200. The received religion information is decrypted by the matching app and recorded as the "religion.json" file in the "matching_temp" directory.

In step S604, the matching app generates a personalized menu compatible with the religion information of the user by editing the ResA.html file. The generated personalized menu is recorded as a new "Custom_ResA.html" file in the "matching_temp" directory. Through the above, as illustrated in FIG. 33, the "religion.json" file, the "ResA.html" file, the "Custom_ResA.html" file, and the "ResA.css" file are recorded in the "matching_temp" directory.

In step S605, the matching app uses the "Custom_ResA.html" file and the "ResA.css" file to draw the generated personalized menu in the style designated by Restaurant A.

In this way, various screens are drawn using HTML/CSS files. For this reason, in the case of presenting a product or service compatible with enormous and diverse personal information about users from among products or services provided by an unspecified large number of businesses from a single matching app, the businesses are able to display expected information in an expected style (for example, UI design).

When the display screen is returned to the home screen of the matching app by the user who has finished ordering a food from the personalized menu, or when a predetermined time has elapsed since the user finished ordering a food from the personalized menu, all of the files temporarily stored in the "matching_temp" directory may be deleted for security.

(Variations of Personalized Menu)

Figure 35:
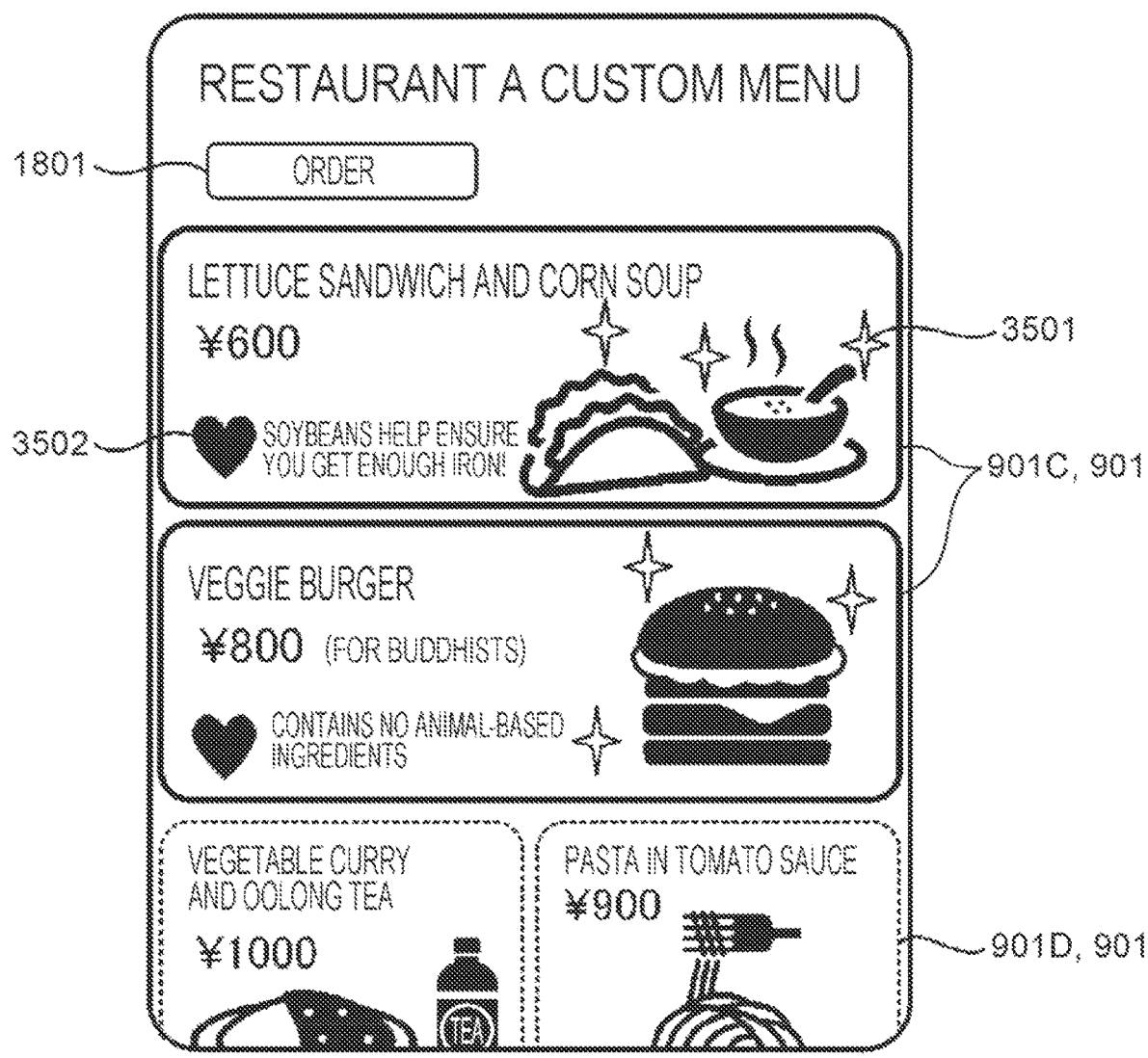
FIG. 35 is a diagram illustrating an example of an operation screen including a first variation of the personalized menu.

The following variations may be adopted instead of the personalized menu illustrated in FIG. 18. FIG. 35 is a diagram illustrating an example of the operation screen G106 including a first variation of the personalized menu. On the personalized menu, for the tile objects 901 indicating each of the foods, the display order, the size, the frame thickness, the frame decoration, the size of an image illustrating the food, a mark 3501 deforming the food around the image illustrating the food, the size of the character string of the food name, a deformation applied to the character string of the food name, and a heart mark 3502 indicating a favorite are set.

The settings for the personalized menu are set according to a priority described later. In the example of FIG. 35, the food of a lettuce sandwich and corn soup has the highest priority, and a veggie burger has the next-highest priority. Consequently, the tile object 901C of the lettuce sandwich is arranged on top, and the tile object 901C of the veggie burger is displayed second from the top. Vegetable curry and oolong tea has the third-highest priority while pasta in tomato sauce has the fourth-highest priority, and consequently the tile objects 901D of these foods are displayed below the tile objects 901C. Note that the tile object 901 for the food having the fifth-highest priority and the foods thereafter are displayable on the display 105 by performing a scrolling operation.

In the tile objects 901C of the two highest-priority foods, the size is increased (for example, doubled) compared to the default size of the tile objects 901D, a decoration that thickens the frame is applied, a decoration that emboldens the character string indicating the food name is applied, the deforming mark 3501 is displayed, the size of the image illustrating the food is increased (for example, doubled) compared to the tile objects 901D, and the heart mark 3502 is displayed. Furthermore, in the tile objects 901C, a message such as "soybeans help ensure you get enough iron" informing the user of the merits of eating the food and a message such as "contains no animal-based ingredients" addressing the user's concerns about eating the food are displayed. A predetermined wording for each food may be adopted in these messages.

Here, only the two highest-priority foods are displayed in the form of the tile objects 901C, but the number of foods displayed in the form of the tile objects 901C is not limited to the two highest-priority foods, and may also be extended to the three or four highest-priority foods, for example.

In the example of FIG. 35, the tile objects 901C are set to nearly the same width as the operation screen G106. On the other hand, the tile objects 901D are set to approximately half the width of the tile objects 901C. Consequently, the tile objects 901D of the third-highest and fourth-highest priority are displayed on the same row. The tile objects of the fifth-highest priority and thereafter are arranged two at a time in the priority order such that two tile objects 901D are positioned on the same row, similarly to the third-highest and fourth-highest tile objects. At this time, the tile objects 901D are arranged on the same row such that the tile object 901D having the higher priority is positioned on the left for example and the tile object 901D having the lower priority is positioned on the right for example. The heights of the two types of tile objects 901C and 901D are set to the same size.

The example of FIG. 35 is a personalized menu for a Buddhist, and therefore the message "for Buddhists" is displayed with respect to the veggie burger.

To achieve the above, the arithmetic unit 104 calculates a priority described later for each food included in the menu information. Additionally, the arithmetic unit 104 generates image data of the operation screen G106 including the personalized menu by arranging the tile objects 901 of the foods in order of highest priority according to predetermined layout information for the personalized menu. As the layout information, information prescribing the placement position of the tile object 901 according to priority and the decoration content described above according to priority for each food may be adopted, for example.

Image data that fits into the display area of the display 105 starting the beginning of the generated image data of the personalized menu is displayed on the display 105 as an initial screen. Subsequently, if an operation of scrolling the display is inputted, the arithmetic unit 104 may cause the display of the personalized menu to scroll by sliding the display area of the personalized menu downward.

In FIG. 35, for the tile objects 901C, the display order, the size, the frame thickness, the frame decoration, the size of the image illustrating the food, the mark 3501 deforming the food around the image illustrating the food, the size of the character string of the food name, the deformation applied to the character string of the food name, and the heart mark 3502 indicating a favorite are set, but at least one of the above settings may be adopted.

Figure 36:
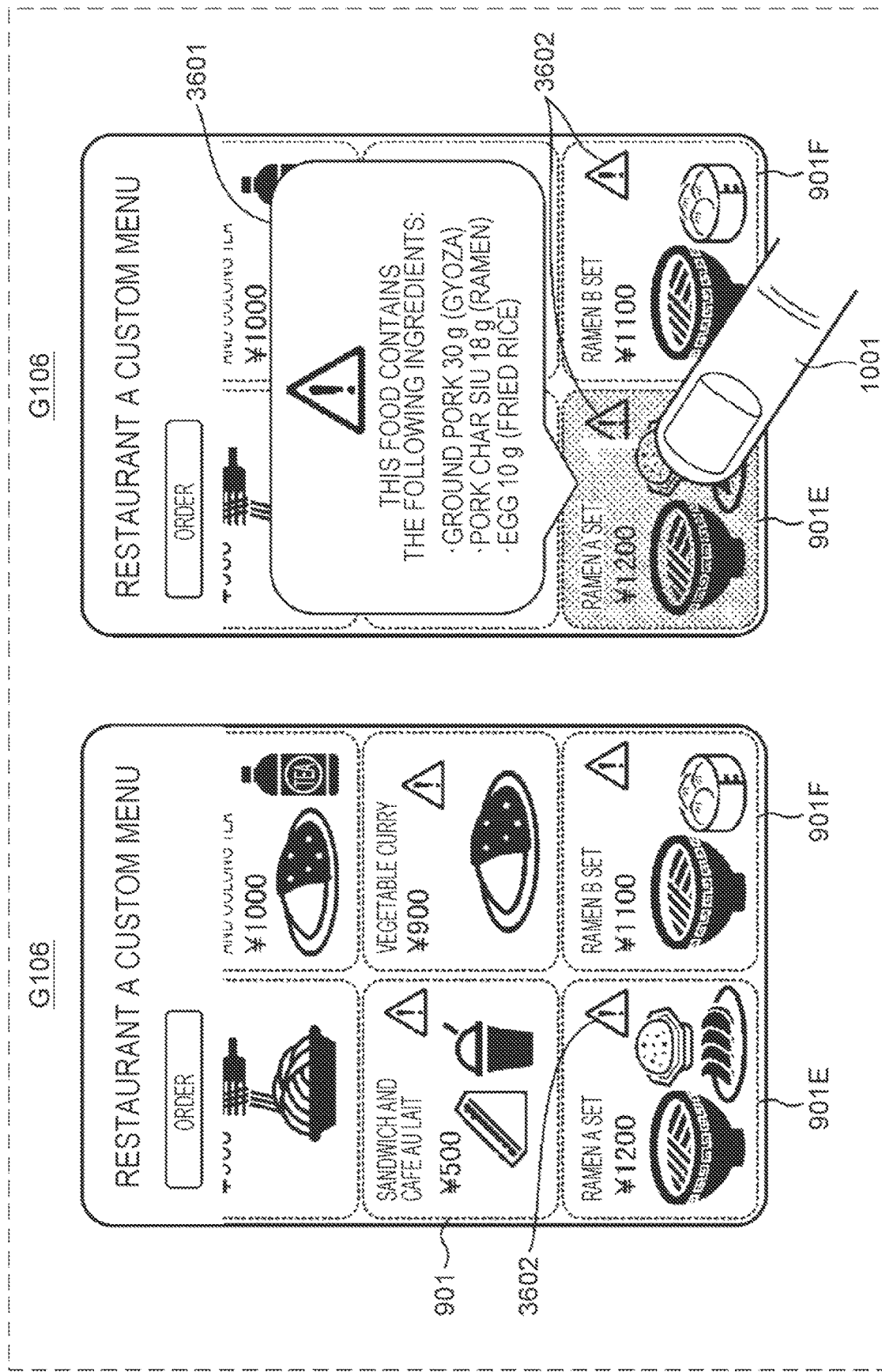
FIG. 36 is a diagram illustrating an example of an operation screen including a second variation of the personalized menu.

FIG. 36 is a diagram illustrating an example of the operation screen G106 including a second variation of the personalized menu. In this example, a display method for a food of lower priority is illustrated. The left side of FIG. 36 illustrates the operation screen G106 before the user selects a tile object 901, while the right side illustrates the operation screen G106 after the user has selected a tile object 901. On the personalized menu, for a food containing an ingredient that should be avoided by the user, a warning mark 3602 is displayed inside the tile object 901 for the food. Additionally, if a tile object 901E including the warning mark 3602 is touched by the pointing object 1001, a pop-up frame 3601 explaining the warning is displayed in association with the touched tile object 901E. Here, the tile object 901E for the Ramen A Set has been selected, and this food contains ground pork, pork char siu, and eggs as ingredients that should be avoided. Consequently, in the pop-up frame 3901, the message "This food contains the following ingredients:" is displayed, and underneath the message, the ingredients that should be avoided and the quantity of each ingredient are displayed in association with each other. With this arrangement, the user is presented with reference information for determining whether or not to order the food. As a result, the user is able to order a food smoothly.

To achieve the above, the arithmetic unit 104 references the ingredient information 2400 and the religion information to determine whether or not each food contains an ingredient that should be avoided, and for the foods that contain an ingredient that should be avoided, the arithmetic unit 104 causes the warning mark 3602 to be displayed in the corresponding tile object 901. Subsequently, if the tile object 901 is touched, the arithmetic unit 104 extracts the ingredient(s) that should be avoided and the quantity of each ingredient from the ingredient information 2400 of the corresponding food, and causes the extracted information to be displayed inside the pop-up frame 3601.

The arithmetic unit 104 may display the warning mark 3602 only on the personalized menu, or also on the standard menu. In the case of displaying the warning mark 3602 on the standard menu, the arithmetic unit 104 may display the warning mark 3602 on the personalized menu with a different appearance than the standard menu. For example, the warning mark 3602 displayed on the personalized menu may be displayed with a larger size, a more conspicuous color, or a more conspicuous pattern compared to the warning mark 3602 displayed on the standard menu.

Figure 37:
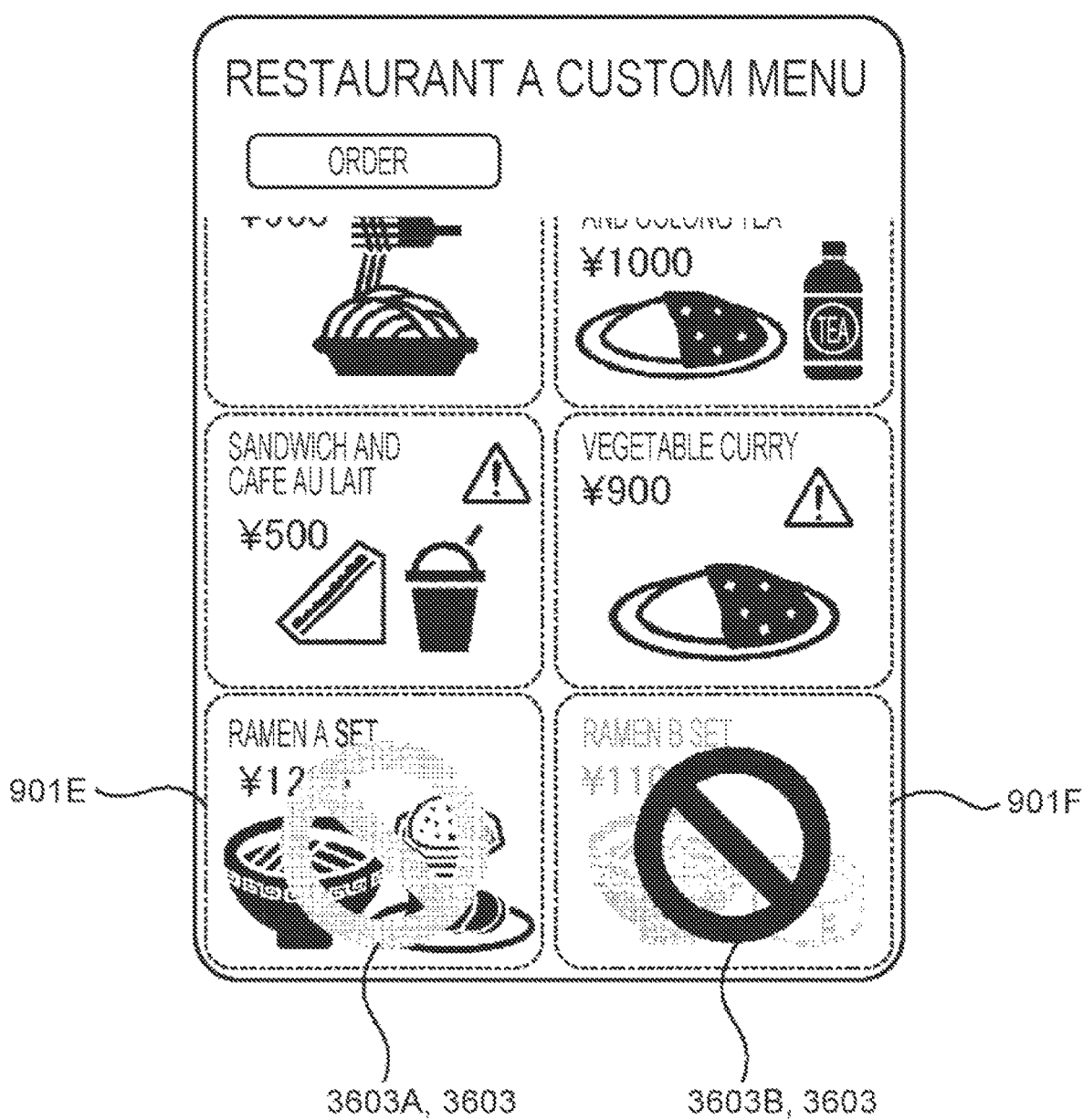
FIG. 37 is a diagram illustrating an example of an operation screen including grayed-out tile objects.

Note that for a food containing an ingredient with a resistance value of 0 that should be avoided absolutely by the user, the arithmetic unit 104 may also display the prohibited mark 3603 illustrated in FIG. 37 instead of the warning mark 3602 on the tile object 901 of the food. Alternatively, for a food containing an ingredient with a resistance value of 0, the arithmetic unit 104 may hide the tile object 901 of the food regardless of religion. Furthermore, the prohibited mark 3603 may also be displayed in the tile object 901 for a food that is not prepared according to a preparation method prescribed by the doctrine of the religion.

Alternatively, for a food containing an ingredient with a resistance value of 0, the arithmetic unit 104 may display the prohibited mark 3603 in the tile object 901 of the food and furthermore prohibit selection by the pointing object 1001. In this case, the tile object 901 of the food may also be grayed out. FIG. 37 is a diagram illustrating an example of the operation screen G106 including grayed-out tile objects 901. Here, a prohibited mark 3603A applied to a tile object 901E indicates a prohibited mark 3603 applied to a tile object 901 that is not grayed out. A prohibited mark 3603B applied to a tile object 901F indicates a prohibited mark 3603 applied to a tile object 901 that is grayed out. The prohibited mark 3603A is displayed in a lighter color than the prohibited mark 3603B. This is to make it easy to distinguish between the image illustrating the food displayed in the tile object 901E and the prohibited mark 3603A. In FIG. 37, the prohibited mark 3603A and the prohibited mark 3603B are both displayed at the same time, but a configuration that displays only one may also be adopted.

A tile object 901F is grayed out by displaying the image illustrating the food semi-transparently. Here, the character string of the food name is not displayed semi-transparently, but the character string may also be displayed semi-transparently.

The arithmetic unit 104 may display the warning mark 3602 in the tile object 901 only for foods containing an ingredient with predetermined resistance values (for example, 1 to 3), and does not have to display the warning mark 3602 for foods containing an ingredient with a resistance value (for example, 4 or 5) other than the predetermined resistance values. Furthermore, in the case where the pointing object 1001 touches a tile object 901 in which the warning mark 3602 or the prohibited mark 3603 is displayed, the arithmetic unit 104 may drive a vibrator provided in the information terminal 100 to cause the information terminal 100 to vibrate. This arrangement makes it possible to inform the user that the food contains an ingredient that should be avoided in an easily understandable way.

The food to which the warning mark 3602 is applied is an example of a food containing an ingredient that the user should avoid as much as possible.

FIG. 38 is a diagram illustrating an example of the operation screen G106 including a third variation of the personalized menu. When the user touches the tile object 901 of a certain food with the pointing object 1001, the personalized menu suggests ordering a food containing a nutrient that the user tends to be deficient in. The left side of FIG. 38 illustrates the operation screen G106 before the user selects a tile object 901, while the right side illustrates the operation screen G106 after the user has selected a tile object 901.

For example, suppose that iron is a nutrient that tends to be deficient in persons who embrace a specific religion. Natto is rich in iron. Accordingly, in this example, when a tile object 901G for "mushroom pasta" is touched by the pointing object 1001, the arithmetic unit 104 displays a pop-up frame 3801 encouraging an additional order of natto in association with the tile object 901G. In the pop-up frame 3801, the message "Add some natto to boost your iron intake?" is displayed, and furthermore, the additional quantity (+1.5 mg) of iron that can be absorbed by adding natto is displayed. This arrangement appeals to the user to supplement iron efficiently by additionally ordering natto.

Moreover, a No button 3804 and a Yes button 3805 are included in the pop-up frame 3801. When the Yes button 3805 is touched by the pointing object 1001, the arithmetic unit 104 determines that an additional order for natto has been placed, and changes the order content from an individual order of "mushroom pasta" to the combination of "mushroom pasta" and "natto". An information mark 3802 is displayed in the tile object 901 of foods which such a pop-up frame 3801 is displayable.

On the other hand, if the No button 3804 is touched by the pointing object 1001, the arithmetic unit 104 does not change the order content.

For example, the arithmetic unit 104 references the ingredient information 2400 of a food to determine whether or not the quantity of a predetermined nutrient (for example, iron) that tends to be deficient in a user who embraces a specific religion falls below a threshold, and applies the information mark 3802 to the food determined to fall below the threshold. In this way, in the case where a food with the information mark 3802 applied is selected, a suggestion for improving nutrient balance and helping to maintain health is provided through the personalized menu.

(Calculation of Priority)

Next, the calculation of priority will be described. In the present embodiment, the arithmetic unit 104 of the information terminal 100 calculates the priority of each food included in the menu information, and generates a personalized menu in which each food is displayed with an appearance corresponding to the priority. Note that foods with a higher priority value are prioritized for display. Hereinafter, a method of calculating the priority will be described. First, the arithmetic unit 104 references the ingredient information 2400 of a certain food and specifies the ingredients contained in the food as well as the quantity of each ingredient. Next, for each ingredient contained in the food that corresponds to an ingredient listed in the classification information illustrated in FIG. 23, the arithmetic unit 104 may perform a process of multiplying the quantity of the ingredient by a coefficient calculated according to (0.2*resistance value−1), and lowering the display priority on the personalized menu for a lower total value of the ingredients contained in the food.

For example, for the Ramen B Set (shoyu ramen and three soup dumplings) illustrated in FIG. 24, the 18 g of pork char siu in the shoyu ramen and the 10 g of ground pork and 10 g of chicken stock in the soup dumplings are calculated as follows with respect to the resistance values of "0" for pork and "0" for chicken in the ingredient list of the classification information illustrated in FIG. 23.

According to $18*(0.2*0-1)+3*(10*(0.2*0-1)+10*(0.2*0-1))=-78$, the priority of the food is calculated as −78. In this way, the arithmetic unit 104 calculates the priority of each food included in the menu information.

(Map Screen)

The present disclosure may also adopt a configuration that causes a personalized menu to be displayed after first causing one or more restaurants compatible with the user's religion to be displayed on a map screen displayed on the information terminal 100.

Figure 39:
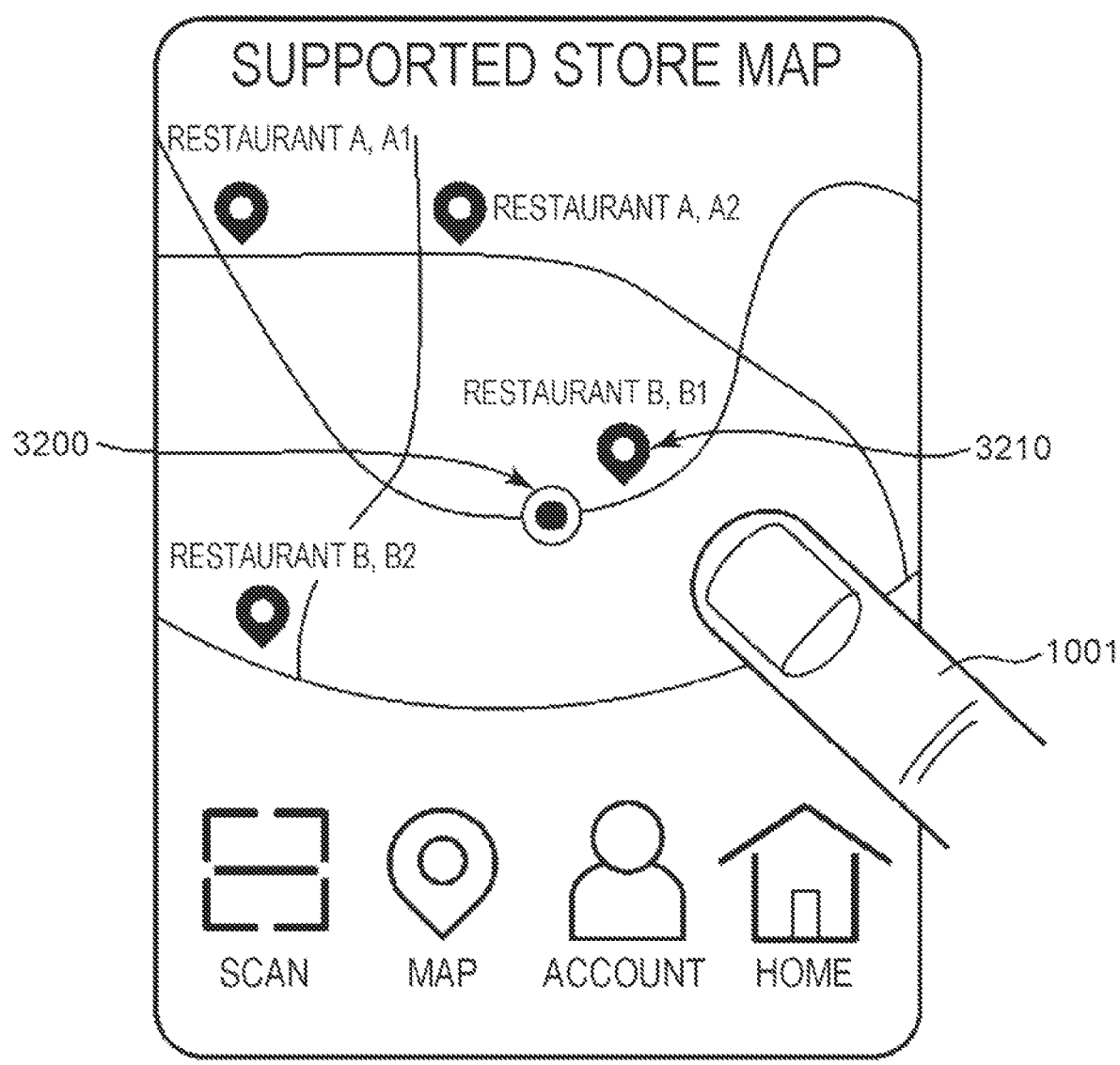
FIG. 39 is a diagram illustrating an example of a map screen displayed on the information terminal.

FIG. 39 is a diagram illustrating an example of a map screen G3900 displayed on the information terminal 100. The map screen G3900 is displayed in the case where an operation of selecting the Map button 1403 on the home screen G103 is inputted. The map screen G3900 includes a map of a geographical region including the current location of the information terminal 100. Additionally, store information about stores supporting the matching app within the geographical region and compatible with the user's religion are displayed on the map screen G3900. Here, in addition to an icon 3200 indicating the current location of the user, a store A1 of Restaurant A, a store A2 of Restaurant A, a store B1 of Restaurant B, and a store B2 of Restaurant B are displayed. A store compatible with a religion refers to a store that is capable of providing foods which contain ingredients allowed to be eaten and which are prepared according to a preparation method prescribed by the doctrine of the religion embraced by the user.

The user selects a desired store to visit while looking at the map screen G3900. In this example, the store B1 of Restaurant B closest to the current location and indicated by an icon 3210 is selected. The user is able to select the store B1 of Restaurant B by touching the icon 3210 with the pointing object 1001, for example. The user selecting the store B1 enters the store B1, and by causing the information terminal 100 to read the restaurant ID and the seat ID described above, the user is able to cause a personalized menu corresponding to the user's religion to be displayed on the information terminal 100.

Figure 40:
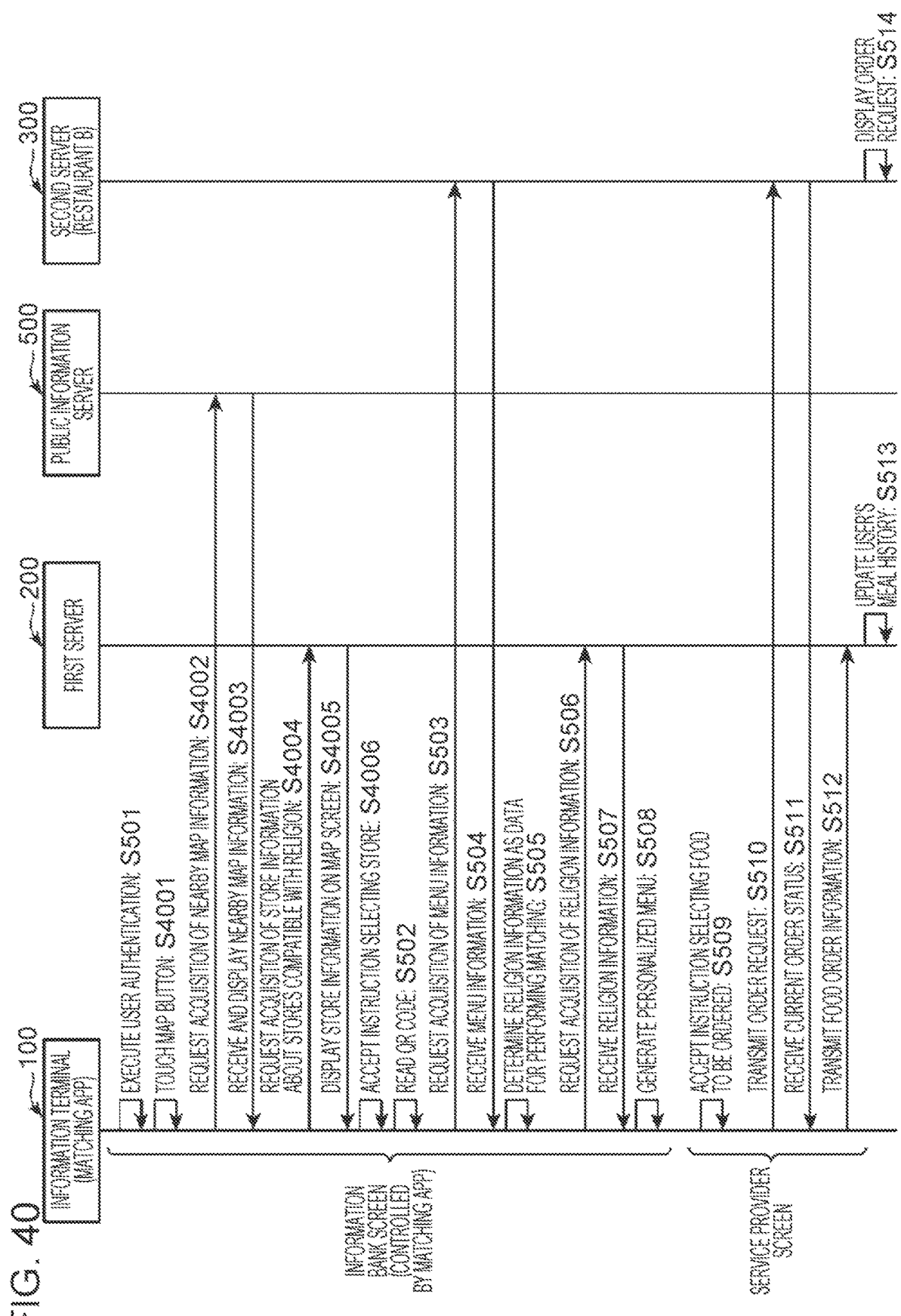
FIG. 40 is a sequence diagram illustrating an example of an overall picture of a process by the information processing system in a case of adopting a configuration in which the user is made to select a restaurant from the map screen.

FIG. 40 is a sequence diagram illustrating an example of an overall picture of a process by the information processing system in a case of adopting a configuration in which the user is made to select a restaurant from the map screen G3900. In FIG. 40, processes which are the same as FIG. 26 are denoted with the same step numbers, and only the differences will be described.

In S4001 following S501, the matching app that has successfully authenticated the user displays the home screen G103, and the Map button 1403 is touched by the user.

In step S4002, the matching app in which the Map button 1403 has been touched acquires position information indicating the current location of the information terminal 100 detected by the GPS sensor 108, and transmits a request to acquire nearby map information, that is, map information about the surrounding region including the current location, to the public information server 500.

The public information server 500 receiving the acquisition request acquires the current location of the information terminal 100 from the position information included in the acquisition request, extracts map information about a region of predetermined range based on the location from a map database as nearby map information, and transmits the extracted nearby map information to the matching app. The matching app receiving the nearby map information displays the map screen G3900 including a map expressed by the nearby map information (step S4003). The predetermined range expressing the region is a range in which the user who is about to eat out can reach a store on foot or by car, such as a range with a radius of 1 km or 2 km from the current location, for example.

The matching app displaying the map screen G3900 transmits a request to acquire store information about stores compatible with the user's religion from among the stores included in the map expressed by the received nearby map information to the first server 200 (step S4004).

The first server 200 receiving the acquisition request extracts store information about stores included in the map and compatible with the user's religion from the memory 203, and transmits the extracted store information to the matching app. A store database including store information about each store is stored in the memory 203, for example. The store information includes the store ID, the store name, position information, and connection information about each store, as well as religion compatibility information. The religion compatibility information is information indicating which of the religions illustrated in FIG. 22 for example can be accommodated by the restaurant. For example, the religion compatibility information is information indicating compatibility with Islam and incompatibility with other religions.

The first server 200 extracts stores included in the region of the map expressed by the store information acquisition request from the position information of each store stored in the store database. Thereafter, the first server 200 cross-references the religion information of the user with the religion compatibility information of each store stored in the store database, extracts stores that are compatible with the user's religion from among the stores included in the region of the specified map, and transmits the store information of the extracted stores to the information terminal 100.

The matching app receiving the extracted store information displays the store information on the map of the map screen G3900 (step S4005). With this arrangement, as illustrated on the map screen G3900 illustrated in FIG. 39, stores which are included in the surrounding region of the user's current location and which are compatible with the user's religion are displayed on the map indicating the surrounding region.

In step S4006, the matching app accepts, from the user, an instruction of selecting a store from among the stores displayed on the map screen G3900. Thereafter, the matching app may use a navigation function to guide the user to the store selected by the user. When the user arrives at the store, the process from step S502 is executed, and a food is ordered.

Note that the map screen G3900 is an example of a 1st first operation screen. Also, in the configuration in which the map screen G3900 is displayed, the operation screen G104 and the operation screen G1011 are examples of a 2nd first operation screen. In this configuration, because stores near the user and compatible with the user's religion are displayed on the map screen G3900, the user is able to check nearby stores which are compatible with the user's religion smoothly.

Note that it is desirable to be able to check what kinds of foods are offered as foods compatible with the user's religion by the store selected by the store selection instruction (step S4006) without actually having to go to the store. In this case, after the store selection instruction (step S4006), the matching app may also provide a button for checking the personalized menu from the selected store. In the above description, the URL "http://restaurantA.com/Store-A/QRorder-18" is acquired by reading the QR code of the seat with the seat number 18, but in this case, a special seat number "00" may be used to access "http://restaurantA.com/Store-A/QRorder-00". In this case, the server of Restaurant A understands that the request is a preliminary request to check the personalized menu from outside the store, and may reply to the matching app with menu information to enable the creation of a personalized menu in which ordering is unavailable and only viewing is possible.

The above description is merely an example, and the present disclosure may be applied in various applications by persons skilled in the art.

In the foregoing embodiment, the user's seat is presumed to be a chair, but the present disclosure is not limited thereto, and the user's seat may correspond to one section of a table where the user eats at a stand-up restaurant, for example.

In the foregoing embodiment, each structural element may be configured by dedicated hardware, or realized by executing a software program suited to each structural element. Each structural element may be realized as a result of a program execution unit such as a CPU or a processor reading out and executing a software program recorded on a recording medium such as a hard disk or semiconductor memory.

The scope of the present disclosure is not limited to the embodiment described above. Embodiments obtained by applying various modifications that may occur to persons skilled in the art or embodiments formed by combining the structural elements in different embodiments may also be included in the scope of the present disclosure insofar as such embodiments do not depart from the gist of the present disclosure.

According to an example of a control method according to the present disclosure, a personalized menu is generated with consideration for ingredients that should be avoided by the user for religious reasons, and therefore the present disclosure is useful in a food ordering system applied to a restaurant.

What is claimed is:

1. A method of controlling an information terminal of a user that communicates over a network with a first server that manages religion information of the user corresponding to identification information that identifies the user, the method comprising:
    acquiring a restaurant ID corresponding to a restaurant and a seat ID indicating a seat of the user through a first operation screen displayed on a display of the information terminal of the user, wherein the first operation screen conforms to a common style designed by a matching app of the first server;
    acquiring, on a basis of the restaurant ID, menu information indicating one or more foods provided by the restaurant over a network from a second server associated with the restaurant corresponding to the restaurant ID;
    transmitting the identification information stored in the information terminal to the first server;
    acquiring, from the first server on a basis of the identification information, the religion information;
    extracting one or more first foods corresponding to the religion information at the information terminal, on a basis of the menu information and the religion information, the religion information including information related to an ingredient that should be avoided according to a religion of the user, the menu information including ingredient information for each food;
    displaying the one or more first foods through a second operation screen for accepting an order of a food to be provided by the restaurant, wherein the second operation screen is customized according to a style designated by the restaurant; and
    transmitting from the information terminal to the second server i) food order information indicating the food selected from among the one or more first foods using the second operation screen and ii) the seat ID.

2. The method according to claim 1, wherein
a second food that is not compatible with the religion information is excluded from the one or more first foods.

3. The method according to claim 1, wherein
the one or more first foods include a food with an added ingredient containing a nutrient that tends to be deficient in correspondence with the religion indicated by the religion information.

4. The method according to claim 1, wherein
the second operation screen includes a display indicating a side dish for supplying a nutrient that tends to be deficient in correspondence with the religion indicated by the religion information.

5. The method according to claim 1, wherein
the one or more first foods include a food with an added ingredient containing a nutrient in which the user has been deficient in past meals consumed by the user over a predetermined period.

6. The method according to claim 1, wherein
the second operation screen includes a display indicating a side dish for supplying a nutrient in which the user has been deficient in past meals consumed by the user over a predetermined period.

7. The method according to claim 1, wherein
the religion information of the user includes the religion of the user and level information indicating a degree to which to avoid an ingredient that should be avoided according to the religion.

8. The method according to claim 1, wherein
the second operation screen includes a food containing an ingredient that the user should avoid as much as possible.

9. The method according to claim 1, wherein
the identification information includes a user ID.

10. The method according to claim 1, wherein
the first server is distinct from the second server.

11. The method according to claim 1, wherein
the restaurant ID and the seat ID are acquired through the first operation screen by reading an identification code prepared at a corresponding position at a table where the user sits.

12. The method according to claim 11, wherein
the identification code includes a QR code.

13. The method according to claim 11, wherein
the identification code is read using Near Field Communication (NFC).

14. The method according to claim 1, wherein
the first server distributively manages the religion information, biometric information, preference information including product purchase history information or food order history information about the user, and activity history information including position information about the user.

15. A method of controlling an information terminal of a user that communicates over a network with a first server that manages religion information of the user corresponding to identification information that identifies the user, the method comprising:

transmitting the identification information stored in the information terminal to the first server;

acquiring, from the first server on a basis of position information and the identification information of the information terminal through a 1st first operation screen displayed on a display of the information terminal of the user, restaurant information expressing one or more restaurants which exist in an area including a point indicated by the position information and which are compatible with a religion indicated by religion information corresponding to the identification information, wherein the 1st first operation screen conforms to a common style designed by a matching app of the first server;

acquiring a restaurant ID corresponding to one restaurant from among the one or more restaurants and a seat ID indicating a seat of the user through a 2nd first operation screen displayed on the display of the information terminal of the user, wherein the 2nd first operation screen conforms to the common style designed by the matching app of the first server;

acquiring, on a basis of the restaurant ID, menu information indicating one or more foods provided by the one restaurant over a network from a second server associated with the one restaurant corresponding to the restaurant ID;

acquiring, from the first server on a basis of the identification information, the religion information;

extracting one or more first foods corresponding to the religion information at the information terminal, on a basis of the menu information and the religion information, the religion information including information related to an ingredient that should be avoided according to the religion of the user, the menu information including ingredient information for each food;

displaying the one or more first foods through a second operation screen for accepting an order of a food to be provided by the restaurant, wherein the second operation screen customized according to a style designated by the one restaurant; and transmitting from the information terminal to the second server i) food order information indicating the food selected from among the one or more first foods using the second operation screen and ii) the seat ID.

16. The method according to claim 15, wherein the position information about the user's information terminal is acquired in the first server by using a GPS system.

17. An information terminal that executes the method according to claim 1.

18. A non-transitory computer-readable recording medium storing a program for causing a computer of the information terminal to execute the method according to claim 1.

19. The non-transitory computer-readable recording medium according to claim 18, wherein the identification information that identifies the user includes a serial code for each information terminal assigned to the program.

* * * * *